United States Patent
Machatha et al.

(10) Patent No.: US 12,098,132 B2
(45) Date of Patent: Sep. 24, 2024

(54) PROCESS FOR PREPARATION OF ALDEHYDE SCAVENGER AND INTERMEDIATES

(71) Applicant: Aldeyra Therapeutics, Inc., Lexington, MA (US)

(72) Inventors: Stephen Gitu Machatha, Wilmington, MA (US); Charles Montgomery, Bolton, MA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 546 days.

(21) Appl. No.: 17/310,104

(22) PCT Filed: May 2, 2020

(86) PCT No.: PCT/US2020/031219
§ 371 (c)(1),
(2) Date: Jul. 16, 2021

(87) PCT Pub. No.: WO2020/223717
PCT Pub. Date: Nov. 5, 2020

(65) Prior Publication Data
US 2022/0089542 A1    Mar. 24, 2022

Related U.S. Application Data

(60) Provisional application No. 62/841,919, filed on May 2, 2019.

(51) Int. Cl.
*C07D 215/38*    (2006.01)
*C07D 215/48*    (2006.01)

(52) U.S. Cl.
CPC ......... *C07D 215/38* (2013.01); *C07D 215/48* (2013.01)

(58) Field of Classification Search
CPC .................................................. C07D 215/38
See application file for complete search history.

(56) References Cited

U.S. PATENT DOCUMENTS

| | | |
|---|---|---|
| 2,086,186 A | 7/1937 | Messer |
| 3,912,748 A | 10/1975 | Evans et al. |
| 4,668,626 A | 5/1987 | Kobayashi et al. |
| 4,956,351 A | 9/1990 | Mesens et al. |
| 5,024,998 A | 6/1991 | Bodor |
| 5,032,392 A | 7/1991 | Varma |
| 5,364,637 A | 11/1994 | De et al. |
| 5,376,645 A | 12/1994 | Stella et al. |
| 5,419,898 A | 5/1995 | Ikejiri et al. |
| 5,472,954 A | 12/1995 | Loftsson |
| 5,493,027 A | 2/1996 | Nichols et al. |
| 5,576,311 A | 11/1996 | Guy |
| 5,668,117 A | 9/1997 | Shapiro |
| 5,767,109 A | 6/1998 | Sanchez et al. |
| 5,998,488 A | 12/1999 | Shinohara et al. |
| 6,107,300 A | 8/2000 | Bakthavatchalam et al. |
| 6,191,127 B1 | 2/2001 | Holscher et al. |
| 6,358,948 B1 | 3/2002 | Zhang et al. |
| 6,444,221 B1 | 9/2002 | Shapiro |
| 6,492,520 B1 | 12/2002 | Chen |
| 6,498,154 B1 | 12/2002 | Grubb et al. |
| 6,515,010 B1 | 2/2003 | Franchini et al. |
| 6,525,056 B2 | 2/2003 | Arvanitis et al. |
| 6,569,879 B2 | 5/2003 | Liu et al. |
| 7,083,803 B2 | 8/2006 | Peyman |
| 7,297,709 B2 | 11/2007 | Dai et al. |
| 7,531,564 B2 | 5/2009 | Malamas et al. |
| 7,563,906 B2 | 7/2009 | Hagihara et al. |
| 7,842,312 B2 | 11/2010 | Burgermeister et al. |
| 7,956,189 B2 | 6/2011 | Chen et al. |
| 7,973,025 B2 | 7/2011 | Jordan et al. |
| 7,982,071 B2 | 7/2011 | Scott et al. |
| 8,158,609 B1 | 4/2012 | Marsh et al. |
| 8,435,965 B2 | 5/2013 | Tabuchi et al. |
| 8,490,764 B2 | 7/2013 | Simester |
| 8,575,221 B2 | 11/2013 | Masse et al. |
| 8,722,669 B2 | 5/2014 | Palczewski et al. |
| 8,791,154 B2 | 7/2014 | Gamache et al. |
| 8,940,721 B2 | 1/2015 | Jordan et al. |
| 8,940,764 B2 | 1/2015 | Jordan et al. |
| 9,067,963 B2 | 6/2015 | Thompson et al. |
| 9,084,730 B2 | 7/2015 | Bedos et al. |
| 9,259,427 B2 | 2/2016 | Tierney et al. |
| 9,265,759 B2 | 2/2016 | Jordan et al. |
| 9,364,430 B2 | 6/2016 | Babul |
| 9,364,471 B2 | 6/2016 | Jordan et al. |
| 9,375,408 B2 | 6/2016 | Singh |
| 9,562,039 B2 | 2/2017 | Julia Jane et al. |

(Continued)

FOREIGN PATENT DOCUMENTS

| | | |
|---|---|---|
| CA | 3032609 A1 | 3/2018 |
| CN | 1830964 A | 9/2006 |

(Continued)

OTHER PUBLICATIONS

Wang, Tetrahedron (2004), 60(13), 2937-2942.*
"Shin iyakuhin no kikaku oyobi shaken houhou no settei nituite nituite (Regarding the setting of the standard and test method of a new medical product" PMSB/ELD Notification No. 568, May 2001, 46 pages (Only Official).
Aldeyra Therapeutics, "Positive Results from Phase IIa Clinical Trials in Subjects with Allergic Conjunctivitis", Press Release, Feb. 29, 2016, 3 pages.
Caira, "Crystalline Polymorphism of Organic Compounds", Topics in Current Chemistry, Jan. 1999, 198:163-208.

(Continued)

*Primary Examiner* — Nizal S Chandrakumar
(74) *Attorney, Agent, or Firm* — Dechert LLP; Andrea L. C. Reid; Joseph W. Arico

(57) ABSTRACT

The present invention relates to methods for synthesizing compounds, and to intermediates thereto, useful for treating various conditions in which aldehyde toxicity is implicated in the pathogenesis.

9 Claims, No Drawings

(56) References Cited

U.S. PATENT DOCUMENTS

| | | |
|---|---|---|
| 9,604,997 B2 | 3/2017 | Jordan et al. |
| 9,650,342 B2 | 5/2017 | Jordan et al. |
| 9,663,526 B2 | 5/2017 | Fensome et al. |
| 9,687,481 B2 | 6/2017 | Brady et al. |
| 9,814,701 B2 | 11/2017 | Jordan et al. |
| 9,817,701 B2 | 11/2017 | Baptist et al. |
| 9,896,419 B2 | 2/2018 | Jordan et al. |
| 10,058,095 B2 | 8/2018 | Czarnik |
| 10,098,894 B2 | 10/2018 | Persicaner et al. |
| 10,111,862 B2 | 10/2018 | Chabala et al. |
| 10,202,348 B2 | 2/2019 | Jordan et al. |
| 10,213,395 B2 | 2/2019 | Brady et al. |
| 10,414,732 B2 | 9/2019 | Buist et al. |
| 10,426,790 B2 | 10/2019 | Young et al. |
| 10,463,687 B2 | 11/2019 | Rodriguez-Boulan et al. |
| 10,543,181 B2 | 1/2020 | Brady et al. |
| 10,550,085 B2 | 2/2020 | Brady et al. |
| 10,588,874 B2 | 3/2020 | Brady et al. |
| 10,736,842 B2 | 8/2020 | Misra |
| 10,744,144 B2 | 8/2020 | Shah |
| 10,781,158 B2 | 9/2020 | Singh |
| 10,864,166 B2 | 12/2020 | Venkatesh et al. |
| 10,913,722 B2 | 2/2021 | Jordan et al. |
| 11,007,157 B2 | 5/2021 | Brady et al. |
| 11,040,039 B2 | 6/2021 | Macdonald et al. |
| 11,046,650 B2 | 6/2021 | Brady et al. |
| 11,129,823 B2 | 9/2021 | Brady et al. |
| 11,197,821 B2 | 12/2021 | Clark et al. |
| 11,312,692 B1 | 4/2022 | Machatha et al. |
| 11,459,300 B2 | 10/2022 | Brady et al. |
| 11,583,529 B2 | 2/2023 | Macdonald et al. |
| 11,701,331 B2 | 7/2023 | Brady et al. |
| 11,724,987 B2 | 8/2023 | Jordan et al. |
| 11,771,664 B2 | 10/2023 | Brady et al. |
| 11,786,518 B2 | 10/2023 | Clark et al. |
| 11,845,722 B2 | 12/2023 | Brady et al. |
| 2004/0132636 A1 | 7/2004 | Dooley et al. |
| 2004/0198828 A1 | 10/2004 | Abelson et al. |
| 2004/0235892 A1 | 11/2004 | Dai et al. |
| 2005/0020603 A1 | 1/2005 | Dai et al. |
| 2005/0090553 A1 | 4/2005 | Shapiro |
| 2005/0130906 A1 | 6/2005 | Matier et al. |
| 2005/0197292 A1 | 9/2005 | Smithson et al. |
| 2005/0234018 A1 | 10/2005 | Lyons et al. |
| 2006/0014786 A1 | 1/2006 | Raut |
| 2006/0111318 A1 | 5/2006 | Okamoto |
| 2006/0183909 A1 | 8/2006 | Schmitt et al. |
| 2006/0189608 A1 | 8/2006 | Bingaman |
| 2006/0257488 A1 | 11/2006 | Hubbard |
| 2007/0129404 A1 | 6/2007 | Hagihara et al. |
| 2007/0135481 A1 | 6/2007 | Jordan et al. |
| 2007/0243257 A1 | 10/2007 | Bedos et al. |
| 2007/0297981 A1 | 12/2007 | Ousler et al. |
| 2008/0108818 A1 | 5/2008 | Chen et al. |
| 2008/0241256 A1 | 10/2008 | Kuhn |
| 2009/0118503 A1 | 5/2009 | Sprott et al. |
| 2009/0182009 A1 | 7/2009 | Jordan et al. |
| 2010/0160304 A1 | 6/2010 | Katayama |
| 2010/0240624 A1 | 9/2010 | Chapin et al. |
| 2010/0331315 A1 | 12/2010 | Haddach et al. |
| 2011/0071091 A1 | 3/2011 | Chowhan et al. |
| 2011/0105450 A1 | 5/2011 | Chapin et al. |
| 2011/0257271 A1 | 10/2011 | Masse et al. |
| 2011/0263645 A1 | 10/2011 | Jordan et al. |
| 2012/0108585 A1 | 5/2012 | Vu |
| 2012/0295967 A1 | 11/2012 | Gamache et al. |
| 2012/0302601 A1 | 11/2012 | Jordan et al. |
| 2013/0165419 A1 | 6/2013 | Lindstrom et al. |
| 2013/0190500 A1* | 7/2013 | Greiner ............... C07D 215/38 564/417 |
| 2014/0038918 A1 | 2/2014 | Rodriguez-Boulan et al. |
| 2014/0050797 A1 | 2/2014 | Venkatesh et al. |
| 2014/0235604 A1 | 8/2014 | Palczewski et al. |
| 2014/0235722 A1 | 8/2014 | Jordine et al. |
| 2015/0209333 A1 | 7/2015 | Jordan et al. |
| 2015/0209345 A1 | 7/2015 | Jordan et al. |
| 2015/0258120 A1 | 9/2015 | Zarnitsyn et al. |
| 2015/0335632 A1 | 11/2015 | Brady et al. |
| 2015/0344432 A1 | 12/2015 | Jordan et al. |
| 2015/0344447 A1 | 12/2015 | Chabala et al. |
| 2016/0009698 A1 | 1/2016 | Julia Jane et al. |
| 2016/0030449 A1 | 2/2016 | Persicaner et al. |
| 2016/0052930 A1 | 2/2016 | Fensome et al. |
| 2016/0136231 A1 | 5/2016 | Gadek |
| 2016/0151381 A1 | 6/2016 | Blackburn et al. |
| 2016/0168098 A1 | 6/2016 | Jordan et al. |
| 2017/0029354 A1 | 2/2017 | Singh |
| 2017/0095449 A1 | 4/2017 | Winters et al. |
| 2017/0143627 A1 | 5/2017 | Misra |
| 2017/0239196 A1 | 8/2017 | Brady et al. |
| 2017/0266220 A1 | 9/2017 | Young et al. |
| 2017/0320829 A1 | 11/2017 | Jordan et al. |
| 2017/0354655 A1 | 12/2017 | Beaupre et al. |
| 2018/0050989 A1 | 2/2018 | Machatha et al. |
| 2018/0092882 A1 | 4/2018 | Jordan et al. |
| 2018/0194733 A1 | 7/2018 | Jordan et al. |
| 2018/0235980 A1 | 8/2018 | Shah |
| 2018/0250306 A1 | 9/2018 | Brady et al. |
| 2018/0265474 A1 | 9/2018 | Buist et al. |
| 2018/0354905 A1 | 12/2018 | Brady et al. |
| 2019/0054023 A1 | 2/2019 | Seaman et al. |
| 2019/0087646 A1 | 3/2019 | Goulden et al. |
| 2019/0105322 A1 | 4/2019 | Macdonald et al. |
| 2019/0125729 A1 | 5/2019 | Chabala et al. |
| 2019/0183878 A1 | 6/2019 | Brady et al. |
| 2019/0210971 A1 | 7/2019 | Jordan et al. |
| 2019/0231715 A1 | 8/2019 | Brady et al. |
| 2019/0247334 A1 | 8/2019 | Brady et al. |
| 2020/0038392 A1 | 2/2020 | Brady et al. |
| 2020/0062712 A1 | 2/2020 | Machatha et al. |
| 2020/0121591 A1 | 4/2020 | Clark et al. |
| 2020/0199075 A1 | 6/2020 | Brady et al. |
| 2020/0246345 A1 | 8/2020 | Brady et al. |
| 2020/0323841 A1 | 10/2020 | Clark et al. |
| 2020/0368182 A1 | 11/2020 | Brady et al. |
| 2021/0269402 A1 | 9/2021 | Jordan et al. |
| 2021/0275469 A1 | 9/2021 | Brady et al. |
| 2021/0317385 A1 | 10/2021 | MacDonald et al. |
| 2021/0347735 A1 | 11/2021 | Brady et al. |
| 2021/0353628 A1 | 11/2021 | Macdonald et al. |
| 2021/0393527 A1 | 12/2021 | Brady et al. |
| 2021/0393612 A1 | 12/2021 | Machatha et al. |
| 2022/0017475 A1 | 1/2022 | Machatha et al. |
| 2022/0089542 A1 | 3/2022 | Machatha et al. |
| 2022/0133629 A1 | 5/2022 | Clark et al. |
| 2022/0133697 A1 | 5/2022 | Machatha et al. |
| 2022/0184057 A1 | 6/2022 | Brady et al. |
| 2022/0202745 A1 | 6/2022 | Brady et al. |
| 2022/0211691 A1 | 7/2022 | Brady et al. |
| 2022/0354857 A1 | 11/2022 | Brady et al. |
| 2023/0041335 A1 | 2/2023 | Jordan et al. |
| 2023/0131929 A1 | 4/2023 | Brady et al. |
| 2023/0149383 A1 | 5/2023 | Brady et al. |
| 2023/0174491 A1 | 6/2023 | Brady et al. |
| 2023/0228744 A1 | 7/2023 | Brady et al. |
| 2023/0248727 A1 | 8/2023 | Macdonald et al. |
| 2023/0293527 A1 | 9/2023 | Macdonald et al. |

FOREIGN PATENT DOCUMENTS

| | | |
|---|---|---|
| CN | 1882339 A | 12/2006 |
| CN | 101048384 A | 10/2007 |
| CN | 101321742 A | 12/2008 |
| CN | 101534826 A | 9/2009 |
| CN | 101611009 A | 12/2009 |
| CN | 104884049 A | 9/2015 |
| CN | 105120866 A | 12/2015 |
| CN | 105704440 A | 6/2016 |
| CN | 108135867 A | 6/2018 |
| CN | 109640983 A | 4/2019 |
| CN | 111527530 A | 8/2020 |
| CN | 112541870 A | 3/2021 |
| CN | 112800947 A | 5/2021 |
| CN | 113168511 A | 7/2021 |

(56) References Cited

FOREIGN PATENT DOCUMENTS

| | | |
|---|---|---|
| EP | 0186367 A2 | 7/1986 |
| EP | 0245054 A1 | 11/1987 |
| EP | 0483881 A1 | 5/1992 |
| EP | 1621199 A1 | 2/2006 |
| EP | 1679308 A1 | 7/2006 |
| EP | 1888548 A1 | 2/2008 |
| EP | 2301549 A1 | 3/2011 |
| GB | 2327672 A | 2/1999 |
| JP | H04264422 A | 9/1992 |
| JP | H06239748 A | 8/1994 |
| JP | H07025758 A | 1/1995 |
| JP | H08175985 A | 7/1996 |
| JP | H09169647 A | 6/1997 |
| JP | H09285529 A | 11/1997 |
| JP | H10306022 A | 11/1998 |
| JP | 2001041757 A | 2/2001 |
| JP | 2001318350 A | 11/2001 |
| JP | 2002003364 A | 1/2002 |
| JP | 2003519698 A | 6/2003 |
| JP | 2005132834 A | 5/2005 |
| JP | 2005187407 A | 7/2005 |
| JP | 3736916 B2 | 1/2006 |
| JP | 2006008568 A | 1/2006 |
| JP | 2007532648 A | 11/2007 |
| JP | 2008542291 A | 11/2008 |
| JP | 4466875 B2 | 5/2010 |
| JP | 4748289 B2 | 8/2011 |
| JP | 2011203665 A | 10/2011 |
| JP | 2012506449 A | 3/2012 |
| JP | 5194218 B2 | 5/2013 |
| JP | 2014515355 A | 6/2014 |
| JP | 2015057437 A | 3/2015 |
| JP | 2015535293 A | 12/2015 |
| JP | 2016508994 A | 3/2016 |
| JP | 2018523700 A | 8/2018 |
| JP | 2018530524 A | 10/2018 |
| JP | 2019507756 A | 3/2019 |
| KR | 20180073554 A | 7/2018 |
| RU | 2010137842 A | 3/2012 |
| RU | 2565448 C2 | 10/2015 |
| SU | 50906 A1 | 11/1936 |
| SU | 509046 A1 | 6/1984 |
| WO | WO-199507274 A1 | 3/1995 |
| WO | WO-1996022992 A1 | 8/1996 |
| WO | WO-1998005645 A1 | 2/1998 |
| WO | WO-1999046237 A1 | 9/1999 |
| WO | WO-2001041757 A1 | 6/2001 |
| WO | WO0151919 A2 | 7/2001 |
| WO | WO-2004082622 A2 | 9/2004 |
| WO | WO-2004091630 A1 | 10/2004 |
| WO | WO-2005035506 A1 | 4/2005 |
| WO | WO-2005040151 A1 | 5/2005 |
| WO | WO-2005051328 A2 | 6/2005 |
| WO | WO-2005079774 A2 | 9/2005 |
| WO | WO-2005105067 A2 | 11/2005 |
| WO | WO-2006000421 A2 | 1/2006 |
| WO | WO-2006002473 A1 | 1/2006 |
| WO | WO-2006049968 A1 | 5/2006 |
| WO | WO-2006077821 A1 | 7/2006 |
| WO | WO-2006127945 A1 | 11/2006 |
| WO | WO-2007118276 A1 | 10/2007 |
| WO | WO-2008014602 A1 | 2/2008 |
| WO | WO2008052086 A1 | 5/2008 |
| WO | WO-2009045479 A1 | 4/2009 |
| WO | WO-2009102418 A1 | 8/2009 |
| WO | WO-2010048332 A2 | 4/2010 |
| WO | WO-2010133672 A1 | 11/2010 |
| WO | WO-2011008202 A1 | 1/2011 |
| WO | WO-2011071995 A2 | 6/2011 |
| WO | WO-2011072141 A1 | 6/2011 |
| WO | WO-2011078204 A1 | 6/2011 |
| WO | WO-2012097173 A2 | 7/2012 |
| WO | WO-2012105887 A1 | 8/2012 |
| WO | WO-2014100425 A1 | 6/2014 |
| WO | WO-2014116593 A1 | 7/2014 |
| WO | WO-2014116836 A2 | 7/2014 |
| WO | WO-2015002893 A1 | 1/2015 |
| WO | WO-2015187942 A1 | 12/2015 |
| WO | WO-2016085939 A2 | 6/2016 |
| WO | WO-2016165626 A1 | 10/2016 |
| WO | WO-2017035077 A1 | 3/2017 |
| WO | WO-2017035082 A1 | 3/2017 |
| WO | WO-2017147617 A1 | 8/2017 |
| WO | WO-2017196881 A1 | 11/2017 |
| WO | WO-2017214201 A1 | 12/2017 |
| WO | WO-2018039192 A1 | 3/2018 |
| WO | WO-2018039197 A1 | 3/2018 |
| WO | WO-2018064354 A1 | 4/2018 |
| WO | WO-2018067860 A1 | 4/2018 |
| WO | WO2018071619 A1 | 4/2018 |
| WO | WO2018091859 A1 | 5/2018 |
| WO | WO-2018170476 A1 | 9/2018 |
| WO | WO-2019075136 A1 | 4/2019 |
| WO | WO-2020018498 A1 | 1/2020 |
| WO | WO-2020028820 A1 | 2/2020 |
| WO | WO-2020033344 A1 | 2/2020 |
| WO | WO-2020068986 A1 | 4/2020 |
| WO | WO-2020072621 A1 | 4/2020 |
| WO | WO-2020118045 A1 | 6/2020 |
| WO | WO-2020198064 A1 | 10/2020 |
| WO | WO-2020223685 A1 | 11/2020 |
| WO | WO-2020223717 A1 | 11/2020 |
| WO | WO-2021051003 A1 | 3/2021 |
| WO | WO-2021195211 A1 | 9/2021 |
| WO | WO-2021211625 A1 | 10/2021 |
| WO | WO-2021231792 A1 | 11/2021 |
| WO | WO-2021248031 A1 | 12/2021 |
| WO | WO-2022150580 A1 | 7/2022 |
| WO | WO-2023278816 A1 | 1/2023 |

OTHER PUBLICATIONS

Kawaguchi et al., "Drug and crystal polymorphism," Journal of human environmental engineering, 2002, 4(2):310-317.

Maghsoodi et al., "Physicomechanical Properties of Naproxen-Loaded Microparticles Prepared from Eudragit L100", AAPS Pharm SciTech., Mar. 2009, 10(1):120-128.

*Neptune Generics, LLC v. Auspex Pharmaceuticals, Inc.*, IPR2015-01313, Paper No. 25, Dec. 9, 2015, 23 pages.

Noriyuki Takada "Souyaku dankai ni okeru genyaku Form sukuri ningu to sentaku (Bulk drug screening and selection in a drug development phase," Pharm Stage, Jan. 2007, 6(10):20-25.

Ono, "Analysis of Salt Selection of Current Active Pharmaceutical Ingredients (API)," Journal of Pharmaceutical Science and Technology, 2013, 73(3):176-182.

Pearl et al., "Inherited disorders of gamma-aminobutyric acid metabolism and advances in ALDH5A1 mutation identification," Dev Med Child Neurol., 2015, 57(7):611-617.

Peralta et al., "Distinct primary structures, ligand-binding properties and tissue-specific expression of four human muscarinic acetylcholine receptors," EMBO. J., 1987, 6(13):3923-3929.

Pickering, D.S., "Pharmacological characterization of melatonin binding sites in Syrian hamster hypothalamus," Eur. J. Pharmacol., 1990, 175(1):71-77.

Pubchem CID 149143404, Aug. 12, 2020, 2 pages.

Pubchem CID 4391047, Sep. 14, 2005, 2 pages.

Pufahl et al., "Development of a Fluorescence-based Enzyme Assay of Human 5-lipoxygenase," Anal. Biochem., 2007, 364:204-212.

Quinlan et al., "4-Hydroxy-2-Nonenal Levels Increase in the Plasma of Patients with Adult Respiratory Distress Syndrome as Linoleic Acid Appears to Fall," Free Radic Res. 1994, 21(2):95-106.

Radu et al., "Isotretinoin treatment inhibits lipofuscin accumulation in a mouse model of recessive Stargardt's macular degeneration," Novartis Foundation Symposium 2004, 25(51-63):177-178(Abstract Only).

Radu et al., "Treatment with isoretinin inhibits lipofusion accumulation in a mouse model of recessive Stargardt's macular degeneration," Proc Natl Acad Sci. USA, 2003, 100(8):4742-4747.

Rajewski et al., "Pharmaceutical applications of cyclodextrins. 2. In vivo drug delivery," J Pharm Sci., 1996; 85(11):1142-1169.

(56) References Cited

OTHER PUBLICATIONS

Rapp et al., "The effects of local anesthetics on retinal function," Vision Research, 1982, 22(9):1097-1103.
Rauli et al., "Validation of Malondialdehyde and 4-Hydroxy-2-trans-Nonenal Measurement in Plasma by NICI-GC-MS1," J Biochem, 1998, 123:918-923.
Reed, "Lipid peroxidation and neurodegenerative disease", Free Radical Biology and Medicine, 2011, 51(7):1302-1319.
Rees et al., "Cloning and characterisation of the human 5-HT5A serotonin receptor," FEBS Lett., 1994, 355:242-246.
Reproxalap (Medchem Express), 2013, 3 pages.
Reynolds et al., "(−)-[3H] desmethoxyverapamil labels multiple calcium channel modulator receptors in brain and skeletal muscle membranes: differentiation by temperature and dihydropyridines," J. Pharmacol. Exp. Ther., 1986, 237:731-738.
Ricca et al., "Amphetamine derivatives and obesity," Appetite, Apr. 2009, 52(2):405-409.
Rinaldi-Carmona et al., "Characterization of two cloned human CB1 cannabinoid receptor isoforms," J. Pharmacol. Exp. Ther., 1996, 278:871-878.
Rivkees et al., "Identification of domains of the human A 1 adenosine receptor that are important for binding receptor subtype-selective ligands using chimeric A1/A2a adenosine receptors," J. Biol. Chem., 1995, 270:20485-20490.
Rizzo et al., "Aldehyde Trapping Agent NS2 Blocks Formation of Fatty Aldehyde Adducts with Phosphatidylethanolamine and Suggests Potential Therapeutic Approach for Sjogren-Larsson Syndrome," Mol Genet and Metab., Mar. 2015, 114(3):362A [Abstract Only].
Rizzo et al., "Endogenous antioxidants and radical scavengers," Advances in Experimental Medicine and Biology, 2010, 698:52-56.
Rizzo et al., "Ichthyosis in Sjogren-Larsson syndrome reflects defective barrier function due to abnormal lamellar body structure and secretion," Arch Dermatol Res, 2010, 302(6):443-451.
Rizzo et al., "Sjogren-Larsson syndrome: molecular genetics and biochemical pathogenesis of fatty aldehyde dehydrogenase deficiency," Mol Genet Metab., 2007, 90(1):1-9.
Rizzo, Fatty aldehyde and fatty alcohol metabolism: review and importance for epidermal structure and function, Biochim Biophys Acta, Mar. 2014, 1841(3):377-389.
Rizzo, "Genetics and prospective therapeutic targets for Sjogren-Larsson Syndrome," Expert Opin Orphan Drugs., 2016, 4(4):395-406.
Rizzo, "The role of fatty aldehyde dehydrogenase in epidermal structure and function" Dermato-Endocrinol, 2011, 3(2):91-99.
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Keratoconjunctivitis Sicca," Merck Manual Professional Version, 5 pages (2016), Available at: https://www.merckmanuals.com/professional/eye-disorders/corneal-disorders/keratoconjunctivitis-sicca.
Roat, "Ocular Mucous Membrane Pemphigoid," Merck Manual Professional Version, Available at: https://www.merckmanuals.com/professional/eye-disorders/conjunctival-and-scleral-disorders/ocular-mucous-membrane-pemphigoid, 2016, 3 pages.
Roat, "Scleritis," Merck Manual Professional Version, 3 pages (2016), Available at: https://www.merckmanuals.com/professional/eye-disorders/conjunctival-and-scleral-disorders/scleritis.
Roberts et al., "Basic Principles of Organic Chemistry," 2nd edition, copyright 1977 W. A. Benjamin, Inc., pp. 580-582.
Saal, et al. "Pharmaceutical salts: A summary on doses of salt formers from the Orange Book", European Journal of Pharmaceutical Sciences, Jul. 16, 2013, 49(4):614-623.
Serajuddin, "Salt formation to improve drug solubility," Adv Drug Deliv Rev., 2007, 59(7):603-616.
Smalley, Science of Synthesis, 2002, 11:289.
Tanna et al., "Stargardt disease: clinical features, molecular genetics, animal models and therapeutic options," Br J Ophthalmol., 2017; 101 (1):25-30.
Tripathi et al., "Monoamine oxidase-B inhibitors as potential neurotherapeutic agents: An overview and update", Med Res Rev., Sep. 2019, 39(5):1603-1706.
Wermuth, "The Practice of Medicinal Chemistry," Elsevier, Second Volume, 1999, pp. 347-365.
Yamano, "Approach to Crystal Polymorph in Process Research of New Drug," Journal of Synthetic Organic Chemistry, 2007, 65:907-913.
Yoko et al., "Drug and Crystal Polymorphism", Journal of Human Environmental Engineering, 2002, 4(2):310-317.
Young et al., "NS2, a novel aldehyde trap, decreases aldehyde levels in dry skin and eye models," Aldeyra therapeutics, 2014, 1 page.
PCT International Preliminary Report on Patentability received for PCT/US2019/054263, dated Apr. 15, 2021, 11 pages.
Extended European Search Report received for European Patent Application No. 13865015.5 dated Mar. 31, 2016, 9 pages.
Extended European Search Report received for European Patent Application No. 19891719.7 dated Jul. 27, 2022, 9 pages.
Partial Supplementary European Search Report received for European Patent Application No. 14743711.5 dated Jul. 20, 2016, 14 pages.
PCT International Preliminary Report on Patentability received for PCT/US2006/020320, dated Nov. 30, 2007, 8 pages.
PCT International Preliminary Report on Patentability received for PCT/US2010/059719, dated Jun. 21, 2012, 7 pages.
PCT International Preliminary Report on Patentability received for PCT/US2013/076592, dated Jul. 2, 2015, 7 pages.
PCT International Preliminary Report on Patentability received for PCT/US2014/012356, dated Jul. 28, 2015, 7 pages.
PCT International Preliminary Report on Patentability received for PCT/US2017/020020, dated Sep. 7, 2018, 10 pages.
PCT International Preliminary Report on Patentability received for PCT/US2017/047945, dated Mar. 7, 2019, 7 pages.
PCT International Preliminary Report on Patentability received for PCT/US2017/047958, dated Mar. 7, 2019, 08 pages.
PCT International Preliminary Report on Patentability received for PCT/US2018/023000, dated Sep. 26, 2019, 7 pages.
PCT International Preliminary Report on Patentability received for PCT/US2018/055310, dated Apr. 23, 2020, 6 pages.
PCT International Preliminary Report on Patentability received for PCT/US2019/052961, dated Apr. 8, 2021, 9 pages.
PCT International Preliminary Report on Patentability received for PCT/US2019/064669, dated Jun. 17, 2021, 10 pages.
PCT International Preliminary Report on Patentability received for PCT/US2020/024022, dated Oct. 7, 2021, 9 pages.
PCT International Preliminary Report on Patentability received for PCT/US2020/031138, dated Nov. 11, 2021, 6 pages.
PCT International Preliminary Report on Patentability received for PCT/US2021/023884, dated Oct. 6, 2022, 8 pages.
PCT International Preliminary Report on Patentability received for PCT/US2021/027148, dated Oct. 27, 2022, 7 pages.
PCT International Preliminary Report on Patentability received for PCT/US2021/032335, dated Nov. 24, 2022, 9 pages.
PCT International Preliminary Report on Patentability received for PCT/US2021/035948, dated Dec. 15, 2022, 8 pages.
PCT International Search Report and Written Opinion received for PCT/CN2022/113284, dated Oct. 18, 2022, 6 pages.
PCT International Search Report and Written Opinion received for PCT/US2006/020320, dated Sep. 26, 2006, 10 pages.
PCT International Search Report and Written Opinion received for PCT/US2013/076592, dated Apr. 30, 2014, 10 pages.
PCT International Search Report and Written Opinion received for PCT/US2014/012356, dated May 30, 2014, 11 pages.
PCT International Search Report and Written Opinion received for PCT/US2014/012762, dated Jul. 18, 2014, 12 pages.
PCT International Search Report and Written Opinion received for PCT/US2016/040064, dated Nov. 15, 2016, 8 pages.
PCT International Search Report and Written Opinion received for PCT/US2016/048054, dated Nov. 4, 2016, 8 pages.

(56) References Cited

OTHER PUBLICATIONS

PCT International Search Report and Written Opinion received for PCT/US2016/048064, dated Nov. 15, 2016, 8 pages.
PCT International Search Report and Written Opinion received for PCT/US2017/047945, dated Oct. 20, 2017, 9 pages.
PCT International Search Report and Written Opinion received for PCT/US2018/055310, dated Jan. 29, 2019, 9 pages.
PCT International Search Report and Written Opinion received for PCT/US2019/044929, dated Nov. 20, 2019, 15 pages.
PCT International Search Report and Written Opinion received for PCT/US2019/052961, dated Dec. 10, 2019, 11 pages.
PCT International Search Report and Written Opinion received for PCT/US2019/069097 dated Dec. 10, 2019, 11 pages.
PCT International Search Report and Written Opinion received for PCT/US2020/050565, dated Dec. 22, 2020, 9 pages.
PCT International Search Report and Written Opinion received for PCT/US2021/035948, dated Oct. 26, 2021, 12 pages.
PCT International Search Report and Written Opinion received for PCT/US2022/011604, dated Mar. 25, 2022, 12 pages.
Search Report and Written Opinion received by the Intellectual Property Office of Singapore for Singapore Patent Application No. 11201505587Y, dated Jul. 12, 2016 (12 pages).
Search Report and Written Opinion received by the Intellectual Property Office of Singapore for Singapore Patent Application No. 11201505599Y dated Sep. 14, 2016 (5 pages).
U.S. Appl. No. 15/437,699 of Jordan et al., filed Feb. 21, 2017.
U.S. Appl. No. 16/547,930 of Buist et al., filed Aug. 22, 2019.
U.S. Appl. No. 17/305,915 of Machatha et al., filed Jul. 16, 2021.
PCT International Preliminary Report on Patentability received for PCT/US2020/031219, dated Nov. 11, 2021, 11 pages.
Abelson and Loeffler, "Conjunctival allergen challenge: models in the investigation of ocular allergy," Curr Allergy Asthma Rep. 2003;3(4):363-8.
Abelson and Spitalny, "Combined analysis of two studies using the conjunctival allergen challenge model to evaluate olopatadine hydrochloride, a new ophthalmic antiallergic agent with dual activity," Am J Ophthalmol. 1998; 125(6):797-804.
Abelson et al., "Conjunctival allergen challenge. A clinical approach to studying allergic conjunctivitis," Arch Ophthalmol. 1990;108(1):84-8.
Abelson et al., "The conjunctival provocation test model of ocular allergy: utility for assessment of an ocular corticosteroid, loteprednol etabonate," J Ocul Pharmacol Ther. 1998;14(6):533-42.
Abramovitz et al., "The utilization of recombinant prostanoid receptors to determine the affinities and selectivities of prostaglandins and related analogs," Biochim Biophys Acta. 2000;1483(2):285-93.
Ackerman et al., "Ocular itch associated with allergic conjunctivitis: latest evidence and clinical management," Ther Adv Chronic Dis. 2016;7(1):52-67.
Acland et al., "Gene therapy restores vision in a canine model of childhood blindness," Nat Genet. 2001;28(1):92-5.
Aharony et al., "Pharmacological characterization of cloned human NK-2 (neurokinin A) receptor expressed in a baculovirus/Sf-21 insect cell system," Mol Pharmacol. 1993;44(2):356-63.
Aktürk et al., "Nitric oxide and malondialdehyde levels in plasma and tissue of psoriasis patients," J Eur Acad Dermatol Venereol. 2012;26(7):833-7.
Al-Bari, "Chloroquine analogues in drug discovery: new directions of uses, mechanisms of actions and toxic manifestations from malaria to multifarious diseases," J Antimicrob Chemother. 2015;70(6):1608-21.
Al-Essa et al., "Clinical, fluorine-18 labeled 2-fluoro-2-deoxyglucose positron emission tomography (FDG PET), MRI of the brain and biochemical observations in a patient with 4-hydroxybutyric aciduria; a progressive neurometabolic disease," Brain Dev. 2000;22(2):127-31.
Al-Hasani et al., "Phosphoryl exchange is involved in the mechanism of the insulin receptor kinase," FEBS Lett. 1994;349(1):17-22.
Albano et al., "Immune response towards lipid peroxidation products as a predictor of progression of non-alcoholic fatty liver disease to advanced fibrosis," Gut. 2005;54(7):987-93.
Aldeyra Therapeutics, "Aldeyra Therapeutics Abstract Accepted at 2015 American Academy of Allergy Asthma & Immunology Annual Meeting: Novel Anti-Inflammatory Data Selected for Late-Breaking Poster Presentation," Press Release. 2014.
Aldeyra Therapeutics, "Aldeyra Therapeutics Abstract Accepted for Presentation at the 2015 Multinational Association of Supportive Care in Cancer-International Society of Oral Oncology (MASCCISOO) Annual Meeting," Press Release. 2015.
Aldeyra Therapeutics, "Aldeyra Therapeutics Abstracts Accepted for Presentation at the 2015 Annual Meeting of the Association for Research in Vision and Ophthalmology," Press Release. 2015.
Aldeyra Therapeutics, "Aldeyra Therapeutics Announces Agreement with Johnson & Johnson Innovation to Advance Novel Immune-Modulating Drugs for Systemic Inflammatory Diseases," Press Release. 2018.
Aldeyra Therapeutics, "Aldeyra Therapeutics Announces Clinical Development Update for Phase 3 Programs," Press Release. 2017.
Aldeyra Therapeutics, "Aldeyra Therapeutics Announces Collaboration With the National Organization for Rare Disorders to Enhance Awareness for Sjogren-Larsson Syndrome Patients," Press Release. 2014.
Aldeyra Therapeutics, "Aldeyra Therapeutics Announces Development Programs at 2018 Research Day," Press Release. 2018.
Aldeyra Therapeutics, "Aldeyra Therapeutics Announces First Patient Enrolled in Allergic Conjunctivitis Phase 2b Clinical Trial," Press Release. 2017.
Aldeyra Therapeutics, "Aldeyra Therapeutics Announces First Patient Enrolled in Allergic Conjunctivitis Phase 3 Clinical Trial," Press Release. 2018.
Aldeyra Therapeutics, "Aldeyra Therapeutics Announces First Patient Enrolled in Allergic Conjunctivitis Phase IIa Clinical Trial," Press Release. 2015.
Aldeyra Therapeutics, "Aldeyra Therapeutics Announces First Patient Enrolled in Dry Eye Disease Phase 2a Clinical Trial," Press Release. 2017.
Aldeyra Therapeutics, "Aldeyra Therapeutics Announces First Patient Enrolled in Dry Eye Disease Phase 2b Clinical Trial," Press Release. 2018.
Aldeyra Therapeutics, "Aldeyra Therapeutics Announces First Patient Enrolled in Noninfectious Anterior Uveitis Phase 3 Clinical Trial," Press Release. 2017.
Aldeyra Therapeutics, "Aldeyra Therapeutics Announces First Patient Enrolled in Noninfectious Anterior Uveitis Phase II Clinical Trial," Press Release. 2015.
Aldeyra Therapeutics, "Aldeyra Therapeutics Announces First Patient Enrolled in Sjogren-Larsson Syndrome Phase II Clinical Trial," Press Release. 2015.
Aldeyra Therapeutics, "Aldeyra Therapeutics Announces First Patient Enrolled in Sjögren-Larsson Syndrome Pivotal Phase 3 Clinical Trial," Press Release. 2018.
Aldeyra Therapeutics, "Aldeyra Therapeutics Announces Last Patient Dosed in Dry Eye Disease Phase 2a Clinical Trial," Press Release. 2017.
Aldeyra Therapeutics, "Aldeyra Therapeutics Announces Last Patient Dosed in Dry Eye Disease Phase 2b Clinical Trial," Press Release. 2018.
Aldeyra Therapeutics, "Aldeyra Therapeutics Announces Last Patient Dosed in Phase II Trial of NS2 in Patients with Allergic Conjunctivitis," Press Release. 2015.
Aldeyra Therapeutics, "Aldeyra Therapeutics Announces Last Patient Dosed in the Alleviate Phase 3 Clinical Trial," Press Release. 2018.
Aldeyra Therapeutics, "Aldeyra Therapeutics Announces Positive Mesothelioma Investigator-Sponsored Clinical Trial Results Presented at The International Association for The Study of Lung Cancer 19th World Conference on Lung Cancer," Press Release. 2018.
Aldeyra Therapeutics, "Aldeyra Therapeutics Announces Positive Results from Dry Eye Disease Phase 2a Clinical Trial," Press Release. 2017.

(56) References Cited

OTHER PUBLICATIONS

Aldeyra Therapeutics, "Aldeyra Therapeutics Announces Positive Results from Phase 2b Dry Eye Disease Clinical Trial," Press Release. 2018.
Aldeyra Therapeutics, "Aldeyra Therapeutics Announces Positive Top-Line Results from the Phase 3 Alleviate Trial in Patients with Allergic Conjunctivitis," Press Release. 2019.
Aldeyra Therapeutics, "Aldeyra Therapeutics Announces Positive Top-Line Symptom and Sign Results from Run-In Cohort of Phase 3 Tranquility Trial in Dry Eye Disease," Jan. 7, 2021.
Aldeyra Therapeutics, "Aldeyra Therapeutics Announces Presentation of Novel Data on the Efficacy of ADX-102 in a Model of Succinic Semialdehyde Dehydrogenase Activity at the 2017 American Society of Human Genetics Annual Meeting," Press Release. 2017.
Aldeyra Therapeutics, "Aldeyra Therapeutics Announces Presentation of Phase 2 Allergic Conjunctivitis Results at the 2016 American College of Allergy, Asthma and Immunology Annual Scientific Meeting," Press Release. 2016.
Aldeyra Therapeutics, "Aldeyra Therapeutics Announces Presentation of Results on the Efficacy of ADX-102 in Noninfectious Anterior Uveitis at the American Uveitis Society Held at the American Academy of Ophthalmology 2017 Annual Meeting," Press Release. 2017.
Aldeyra Therapeutics, "Aldeyra Therapeutics Announces Results from Allergic Conjunctivitis Phase 2b Clinical Trial and Plans for Phase 3 Clinical Testing," Press Release. 2017.
Aldeyra Therapeutics, "Aldeyra Therapeutics Announces Third Quarter 2017 Financial Results," Press Release. 2017.
Aldeyra Therapeutics, "Aldeyra Therapeutics Launches the Aldeyra Registry for Patients with Sjögren-Larsson Syndrome," Press Release. 2017.
Aldeyra Therapeutics, "Aldeyra Therapeutics Opens Enrollment in Noninfectious Anterior Uveitis Phase II Clinical Trial," Press Release. 2015.
Aldeyra Therapeutics, "Aldeyra Therapeutics Opens Enrollment in Sjogren-Larsson Syndrome Clinical Trial and Finalizes Noninfectious Anterior Uveitis Clinical Trial Protocol," Press Release. 2015.
Aldeyra Therapeutics, "Aldeyra Therapeutics Presents Dry Eye Disease Phase 2a Clinical Trial Results at the Association for Research in Vision and Ophthalmology 2018 Annual Meeting," Press Release. 2018.
Aldeyra Therapeutics, "Aldeyra Therapeutics Presents Evidence for Aldehyde Sequestration as a Potential Therapeutic Approach in Succinic Semialdehyde Dehydrogenase Deficiency at the American Society of Human Genetics 2017 Annual Meeting," Press Release. 2017.
Aldeyra Therapeutics, "Aldeyra Therapeutics Presents Noninfectious Anterior Uveitis Phase 2 Clinical Trial Data at the Association for Research in Vision and Ophthalmology 2017 Annual Meeting," Press Release. 2017.
Aldeyra Therapeutics, "Aldeyra Therapeutics Presents Noninfectious Anterior Uveitis Phase 2 Clinical Trial Data to the American Uveitis Society Held at the American Academy of Ophthalmology 2017 Annual Meeting," Press Release. 2017.
Aldeyra Therapeutics, "Aldeyra Therapeutics Provides Update on Late-Stage Clinical Trials at 2016 Research and Development Day," Press Release. 2016.
Aldeyra Therapeutics, "Aldeyra Therapeutics Provides Update on NS2 Clinical Program," Press Release. 2015.
Aldeyra Therapeutics, "Aldeyra Therapeutics Provides Update on Ophthalmic Programs at 2019 Research & Development Day," Press Release. 2019.
Aldeyra Therapeutics, "Aldeyra Therapeutics Reaches Agreement with the US Food and Drug Administration for the Use of RASP as an Objective Sign for the Treatment of Dry Eye Disease," Press Release. 2020.
Aldeyra Therapeutics, "Aldeyra Therapeutics Schedules Conference Call and Webcast to Announce Results from Allergic Conjunctivitis Phase 2b Clinical Trial," Press Release. 2017.
Aldeyra Therapeutics, "Aldeyra Therapeutics Schedules Conference Call to Present Results of a Randomized, Double-Blind, Vehicle-Controlled Clinical Trial in Sjogren-Larsson Syndrome," Press Release. 2016.
Aldeyra Therapeutics, "Aldeyra Therapeutics Schedules Webcast and Conference Call to Announce Results from Dry Eye Disease Phase 2a Clinical Trial," Press Release. 2017.
Aldeyra Therapeutics, "Aldeyra Therapeutics Selected for Podium Presentation of Phase 2a Dry Eye Disease Results at the 2018 Association for Research in Vision and Ophthalmology (ARVO) Annual Meeting," Press Release. 2018.
Aldeyra Therapeutics, "Aldeyra Therapeutics Submits FDA IND Filing for Noninfectious Anterior Uveitis," Press Release. 2014.
Aldeyra Therapeutics, "Aldeyra Therapeutics Submits IND Filing to FDA for Clinical Testing of NS2 in Patients With Sjogren-Larsson Syndrome," Press Release. 2015.
Aldeyra Therapeutics, "Aldeyra Therapeutics to Host 2019 Research & Development Day," Press Release. 2019.
Aldeyra Therapeutics, "Aldeyra Therapeutics to Present at the 2016 SSADH Symposium," Press Release. 2016.
Aldeyra Therapeutics, "Aldeyra Therapeutics to Present Novel Data on a Potential Treatment for Sjogren-Larsson Syndrome at the 2015 Society for Inherited Metabolic Disorders Annual Meeting," Press Release. 2015.
Aldeyra Therapeutics, "Aldeyra Therapeutics to Present Novel Data on a Potential Treatment for Succinic Semi-Aldehyde Dehydrogenase Deficiency at the 2015 American Society of Human Genetics (ASHG) Annual Meeting," Press Release. 2015.
Aldeyra Therapeutics, "Aldeyra Therapeutics' Data on Lead Candidate NS2 to be Presented at Society for Investigative Dermatology 2014 Annual Meeting," Press Release. 2014.
Aldeyra Therapeutics, "Aldeyra Therapeutics, Inc. Announces Last Patient Dosed in Allergic Conjunctivitis Phase 2b Clinical Trial," Press Release. 2017.
Aldeyra Therapeutics, "Aldeyra Therapeutics, Inc. Announces Last Patient Dosed in Phase II Clinical Trial of Topical Dermatologic NS2 in Patients With Sjogren-Larsson Syndrome," Press Release. 2016.
Aldeyra Therapeutics, "Aldeyra Therapeutics, Inc. Receives Orphan Drug Designation from the U.S. Food and Drug Administration for ADX-102 in Sjogren-Larsson Syndrome," Press Release. 2017.
Aldeyra Therapeutics, "Phase II Allergic Conjunctivitis," Press Release. 2016.
Aldeyra Therapeutics, "Positive Results From Phase II Clinical Trial in Subjects With Noninfectious Anterior Uveitis," Press Release. 2016.
Aldeyra Therapeutics, Inc., "A Randomized, Double Masked, Clinical Study of Subjects with Dry Eye Syndrome," ClinicalTrials.gov identifier NCT03162783. First Posted May 22, 2017; https://clinicaltrials.gov/ct2/show/NCT03162783.
Aldeyra Therapeutics, Inc., "A Safety and Activity Study of NS2 in Subjects with Allergic Conjunctivitis," ClinicalTrials.gov identifier NCT02578914. First Posted Oct. 19, 2015; https://clinicaltrials.gov/ct2/show/NCT02578914.
Aldeyra Therapeutics, Inc., "A Safety and Efficacy Study of NS2 in Patients with Anterior Uveitis," ClinicalTrials.gov identifier NCT02406209. First Posted Apr. 2, 2015; https://clinicaltrials.gov/ct2/show/NCT02406209.
Aldeyra Therapeutics, Inc., "A Study of Topical NS2 Cream to Treat Ichthyosis in Sjogren-Larsson Syndrome (SLS)," ClinicalTrials.gov Identifier NCT02402309. First Posted Mar. 30, 2015; https://clinicaltrials.gov/ct2/show/NCT02402309.
Aldini et al., "Lipoxidation-derived reactive *carbonyl* species as potential drug targets in preventing protein carbonylation and related cellular dysfunction," ChemMedChem. 2006;1(10):1045-58.
Aldini et al., "The carbonyl scavenger carnosine ameliorates dyslipidaemia and renal function in Zucker obese rats," J Cell Mol Med. 2011;15(6):1339-54.
Allergan, "Restasis® Prescribing Information," copyright 2016, revised 2017.

(56) References Cited

OTHER PUBLICATIONS

Amara et al., "Autoantibodies to malondialdehyde-modified epitope in connective tissue diseases and vasculitides," Clin Exp Immunol. 1995;101(2):233-8.
Ao et al., "Methyl-(beta)-Cyclodextrin Impairs the Monocyte-Adhering Ability of Endothelial Cells by Down-Regulating Adhesion Molecules and Caveolae and Reorganizing the Actin Cytoskeleton," Biol Pharm Bull. 2016;39(6):1029-34.
Apparsundaram et al., "Molecular cloning of a human, hemicholinium-3-sensitive choline transporter," Biochem Biophys Res Commun. 2000;276(3):862-7.
Ardati et al., "Interaction of [3H]orphanin FQ and 125I-Tyr14-orphanin FQ with the orphanin FQ receptor: kinetics and modulation by cations and guanine nucleotides," Mol Pharmacol. 1997;51(5):816-24.
Ashton et al., "Location of penetration and metabolic barriers to levobunolol in the corneal epithelium of the pigmented rabbit," J Pharmacol Exp Ther. 1991;259(2):719-24.
Atkinson et al., "Triazaphenanthrenes. Part VI. Further Observations on the Widman-Stoermer and Brosche Reactions," J Chem Soc C. 1966;2053-60.
Augustin et al., "Oxidative reactions in the tear fluid of patients suffering from dry eyes," Graefes Arch Clin Exp Ophthalmol. 1995;233(11):694-8.
Axelsson et al., "Experimental colitis induced by dextran sulphate sodium in mice: beneficial effects of sulphasalazine and olsalazine," Aliment Pharmacol Ther. 1998;12(9):925-34.
Bachman and Welton, "Quinoline derivatives from 3-nitro-4-hydroxyquinoline," J Am Chem Soc. 1947;69(2):365-71.
Bacsi et al., "Effect of pollen-mediated oxidative stress on immediate hypersensitivity reactions and late-phase inflammation in allergic conjunctivitis," J Allergy Clin Immunol. 2005;116(4):836-43.
Badii, "Allergic Conjunctivitis," Healthline. 2016; Retrieved 2019: https://www.healthline.com/health/allergic-conjunctivitis.
Balci et al., "Effects of computer monitor-emitted radiation on oxidant/antioxidant balance in cornea and lens from rats," Mol Vis. 2009;15:2521-5.
Balci et al., "Investigation of oxidative stress in pterygium tissue," Mol Vis. 2011;17:443-447.
Ballard et al., "Effects of sildenafil on the relaxation of human corpus cavernosum tissue in vitro and on the activities of cyclic nucleotide phosphodiesterase isozymes," J Urol. 1998;159(6):2164-71.
Baltatzis et al., "Mycophenolate mofetil as an immunomodulatory agent in the treatment of chronic ocular inflammatory disorders," Ophthalmology. 2003;110(5):1061-5.
Bardwell et al., "Docking sites on mitogen-activated protein kinase (MAPK) kinases, MAPK phosphatases and the Elk-1 transcription factor compete for MAPK binding and are crucial for enzymic activity," Biochem J. 2003;370(Pt 3):1077-1085.
Baron et al., "[3H]MDL 105,519, a high-affinity radioligand for the N-methyl-D-aspartate receptor-associated glycine recognition site," J Pharmacol Exp Ther. 1996;279(1):62-8.
Bartoli et al., "Malondialdehyde in exhaled breath condensate as a marker of oxidative stress in different pulmonary diseases," Mediators Inflamm. 2011;2011:891752.
Bastin et al., "Salt Selection and Optimisation Procedures for Pharmaceutical New Chemical Entities," Org Proc Res Dev. 2000;4(5):427-35.
Batista et al., "Age-dependent changes in rat lacrimal gland antioxidant and vesicular related protein expression profiles," Mol Vis. 2012;18:194-202.
Batista et al., "Short-term treatment with bisphenol—A leads to metabolic abnormalities in adult male mice," PLoS One. 2012;7(3):e33814.
Baum et al., "Omega 3 fatty acid inhibition of inflammatory cytokine-mediated Connexin43 regulation in the heart," Front Physiol. 2012;3:272.
Baz et al., "Plasma reactive oxygen species activity and antioxidant potential levels in rosacea patients: correlation with seropositivity to Helicobacter pylori," Int J Dermatol. 2004;43(7):494-7.
Berge et al., "Pharmaceutical salts," J Pharm Sci. 1977; 66(1); 1-19.
Berkhout et al., "Cloning, in vitro expression, and functional characterization of a novel human CC chemokine of the monocyte chemotactic protein (MCP) family (MCP-4) that binds and signals through the CC chemokine receptor 2B," J Biol Chem. 1997;272(26):16404-13.
Bermudez and Grau, "Thermosensitive poloxamer-based injectables as controlled drug release platforms for veterinary use: Development and in-vitro evaluation," Int Res J Pharm Pharmacol. 2011;1(6):109-118.
Bernstein and Rando, "The specific inhibition of 11-cis-retinyl palmitate formation in the frog eye by diaminophenoxypentane, an inhibitor of rhodopsin regeneration," Vision Res. 1985;25(6):741-8.
Bernstein et al., "Mechanism of action of aromatic amines that short-circuit the visual cycle," Biochemistry. 1986;25(11):3370-7.
Bernstein et al., "Retinal toxicity associated with occupational exposure to the fish anesthetic MS-222," Am J Ophthalmol. 1997;124(6):843-4.
Bernstein et al., "Short-circuiting the visual cycle with retinotoxic aromatic amines," Proc Natl Acad Sci U S A. 1986;83(6):1632-5.
Bickett et al., "A high throughput fluorogenic substrate for interstitial collagenase (MMP-1) and gelatinase (MMP-9)," Anal Biochem. 1993;212(1):58-64.
Bignon et al., "SR146131: a new potent, orally active, and selective nonpeptide cholecystokinin subtype 1 receptor agonist. I. In vitro studies," J Pharmacol Exp Ther. 1999;289(2):742-51.
Blindauer et al., "A randomized controlled trial of etilevodopa in patients with Parkinson disease who have motor fluctuations," Arch Neurol. 2006;63(2):210-6.
Boldogh et al., "ROS generated by pollen NADPH oxidase provide a signal that augments antigen-induced allergic airway inflammation," J Clin Invest. 2005;115(8):2169-79.
Boner et al., "Bronchodilating activity of oral clenbuterol in asthmatic children after single administration of different dosages," Pediatr Pulmonol. 1987;3(1):34-7.
Bousquet et al., "How to design and evaluate randomized controlled trials in immunotherapy for allergic rhinitis: an ARIA-GA(2) LEN statement," Allergy. 2011;66(6):765-74.
Boyer et al., "Lipofuscin and N-retinylidene-N-retinylethanolamine (A2E) accumulate in retinal pigment epithelium in absence of light exposure: their origin is 11-cis-retinal," J Biol Chem. 2012;287(26):22276-86.
Bozkir et al., "Effect of hydroxypropyl-beta-cyclodextrin on the solubility, stability and in-vitro release of ciprofloxacin for ocular drug delivery," Acta Pol Pharm. 2012;69(4):719-24.
Bragagni et al., "Cyclodextrin complexation highly enhances efficacy of arylsulfonylureido benzenesulfonamide carbonic anhydrase inhibitors as a topical antiglaucoma agents," Bioorg Med Chem. 2015;23(18):6223-7.
Brandt et al., "The Prevalence of Non-Alcoholic Fatty Liver Disease in Patients With Inflammatory Bowel Disease," American Journal of Gastroenterology 2017;112:S542,S544.
Brenneman et al., "Cannabidiol Provides Protection from Ethanol and Ammonium toxicity in a Hippocampal Model of Hepatic Encephalopathy," 24th Annual Symposium of the International Cannabinoid Research Society, Baveno, Italy. 2014;73.
Brenneman et al., "Small molecule anticonvulsant agents with potent in vitro neuroprotection," J Mol Neurosci. 2012;47(2):368-79.
Brewitt and Sistani, "Dry eye disease: the scale of the problem," Surv Ophthalmol. 2001;45 Suppl 2:S199-202.
BRIDION® (sugammadex) Injection, for intravenous use, Highlights of Prescribing Information. 2015.
Brockhaus et al., "Identification of two types of tumor necrosis factor receptors on human cell lines by monoclonal antibodies," Proc Natl Acad Sci U S A. 1990;87(8):3127-31.
Brown, "3H-batrachotoxinin-A benzoate binding to voltage-sensitive sodium channels: inhibition by the channel blockers tetrodotoxin and saxitoxin," J Neurosci. 1986;6(7):2064-70.

(56) References Cited

OTHER PUBLICATIONS

Brozek et al., "Grading quality of evidence and strength of recommendations in clinical practice guidelines: Part 2 of 3. The Grade approach to grading quality of evidence about diagnostic tests and strategies," Allergy. 2009;64(8):1109-16.
Bryant et al., "A novel class of 5-HT2A receptor antagonists: aryl aminoguanidines," Life Sci. 1996;59(15):1259-68.
Bucciantini et al., "Inherent toxicity of aggregates implies a common mechanism for protein misfolding diseases," Nature. 2002;416(6880):507-11.
Buchan et al., "Characterization of three non-peptide endothelin receptor ligands using human cloned ETA and ETB receptors," Br J Pharmacol. 1994; 112(4):1251-7.
Buddi et al., "Evidence of oxidative stress in human corneal diseases," J Histochem Cytochem. 2002;50(3):341-51.
Bundgaard, "(C) Means to Enhance Penetration: (1) Prodrugs as a means to improve the delivery of peptide drugs," Adv Drug Deliv Rev. 1992;8:1-38.
Burcham et al., "Aldehyde-sequestering drugs: tools for studying protein damage by lipid peroxidation products," Toxicology. 2002;181-182:229-36.
Burstein, "Preservative cytotoxic threshold for benzalkonium chloride and chlorhexidine digluconate in cat and rabbit corneas," Invest Ophthalmol Vis Sci. 1980;19(3):308-13.
Burstein, "The effects of topical drugs and preservatives on the tears and corneal epithelium in dry eye," Trans Ophthalmol Soc U K (1962). 1985;104(Pt 4):402-9.
Canonica et al., "Recommendations for standardization of clinical trials with Allergen Specific Immunotherapy for respiratory allergy. A statement of a World Allergy Organization (WAO) taskforce," Allergy. 2007;62(3):317-24.
Canonica et al., "Sub-lingual immunotherapy: World Allergy Organization Position Paper 2009," Allergy. 2009;64 Suppl 91:1-59.
Casanaro et al., "A convenient solvent system for cellulose dissolution and derivatization: Mechanistic aspects of the acylation of the biopolymer in tetraallylammonium fluoride/dimethyl sulfoxide," Carbohydr Polym. 2011;8(3):1395-402.
Casanaro et al., "Efficacy of vigabatrin intervention in a mild phenotypic expression of succinic semialdehyde dehydrogenase deficiency," JIMD Rep. 2012;2:119-23.
Cejková et al., "The role of conjunctival epithelial cell xanthine oxidoreductase/xanthine oxidase in oxidative reactions on the ocular surface of dry eye patients with Sjögren's syndrome," Histol Histopathol. 2007;22(9):997-1003.
Cesura et al., "Characterization of the binding of [3H]Ro 41-1049 to the active site of human monoamine oxidase-A," Mol Pharmacol. 1990;37(3):358-66.
Chao et al., "Co-existence of non-alcoholic fatty liver disease and inflammatory bowel disease: A review article," World J Gastroenterol. 2016;22(34): 7727-7734.
Chapple et al., "Unfolding retinal dystrophies: a role for molecular chaperones?" Trends Mol Med. 2001;7(9):414-21.
Chen et al., "Methazolamide Calcium Phosphate Nanoparticles in an Ocular Delivery System," Pharm Soc Japan, 2010; 130(3):419-24.
Cheng et al., "A synthetic peptide derived from p34cdc2 is a specific and efficient substrate of src-family tyrosine kinases," J Biol Chem. May 5, 1992;267(13):9248-56.
Chiarpotto et al., "Role of 4-hydroxy-2,3-nonenal in the pathogenesis of fibrosis," Biofactors. 2005;24(1-4):229-36.
Chicchi et al., "Alterations in receptor activation and divalent cation activation of agonist binding by deletion of intracellular domains of the glucagon receptor," J Biol Chem. 1997;272(12):7765-9.
Choi et al., "Expression of Lipid Peroxidation Markers in the Tear Film and Ocular Surface of Patients with Non-Sjogren Syndrome: Potential Biomarkers for Dry Eye Disease," Curr Eye Res. 2016;41(9):1143-9.
Choi et al., "The human serotonin 5-HT2B receptor: pharmacological link between 5-HT2 and 5-HT1D receptors," FEBS Lett. 1994;352(3):393-9.

Ciolino et al., "Effect of alcaftadine 0.25% on ocular itch associated with seasonal or perennial allergic conjunctivitis: a pooled analysis of two multicenter randomized clinical trials," Clin Ophthalmol. 2015;9:765-72.
Clark et al., "Inhibition of dexamethasone-induced cytoskeletal changes in cultured human trabecular meshwork cells by tetrahydrocortisol," Invest Ophthalmol Vis Sci. 1996;37(5):805-13.
Clinical Trials Results for Outcome Measures of Ocular Itching and Ocular Tearing (1 page) (2016).
Clinical Trials Results of Treatment with Aldehyde Trapping Compound NS2 (1 page) (2015).
Clinical Trials Results of Treatment with NS2 Topical Formulation (1 page) (2015).
Conover et al., "Thiazole Analogs of Pyridoxine," Journal of the American Chemical Society, 72(11):5221-5225 (1950).
Cooper et al., "Clinicopathologic study of dextran sulfate sodium experimental murine colitis," Lab Invest, 69(2):238-49 (Aug. 1993).
Couvineau et al., "Molecular identification and structural requirement of vasoactive intestinal peptide (VIP) receptors in the human colon adenocarcinoma cell line, HT-29," Biochem. J., 231:139-143 (1985).
Cullen et al., "Administration of the small molecule aldehyde trap NS2 in a hamster model of radiation-induced oral mucositis," ISOO 2015 Annual Meeting Abstract, Support Care Cancer, 23 (Suppl 1):S107 (Jun. 2015).
Cullen et al., "The small molecule aldehyde trap NS2 exhibits potent anti-inflammatory activity in three murine models of inflammation," AAAAI Annual Meeting Abstract, 1 page (Feb. 2015).
Davies, "Biopharmaceutical considerations in topical ocular drug delivery," Clin Exp Pharmacol Physiol, 2000; 27(7):558-62.
De Jong, "Age-Related Macular Degeneration," N Engl J Med, 355(14):1474-1485 (2006).
Del Valle, "Cyclodextrins and their uses: a review," Process Biochemistry, 2004; 39(9):1033-1046.
Demir et al., "Oxidative stress of intracameral lidocaine and levobupivacaine on ocular tissues," Br J Ophthalmol, 2010; 94(8):1083-7.
Demir et al., "The protective effect of alpha-lipoic acid against oxidative damage in rabbit conjunctiva and cornea exposed to ultraviolet radiation," Ophthalmologica, 2005; 219(1):49-53.
Dente et al., "Modified phage peptide libraries as a tool to study specificity of phosphorylation and recognition of tyrosine containing peptides," J. Mol. Biol., 269:694-703 (1997).
Devedjian et al., "Further characterization of human alpha 2-adrenoceptor subtypes: [31-1]RX821002 binding and definition of additional selective drugs," Eur. J. Pharmacol., 252:43-49 (1994).
Devillier et al., "The allergen challenge chamber: A valuable tool for optimizing the clinical development of pollen immunotherapy," Allergy, 2011; 66(2):163-9.
Division of AIDS, National Institute of Allergy and Infectious Diseases, National Institutes of Health, US Department of Health and Human Services, Division of AIDS (DAIDS) Table for Grading the Severity of Adult and Pediatric Adverse Events, V2.0, 33 pages. (Nov. 2014).
Dolmotova et al., "Cardiomyocyte ATP release through pannexin 1 aids in early fibroblast activation," Am. J. Physiol Heart Circ Physiol 303(10):H1208-1218 (2012).
Dorje et al., "Antagonist binding profiles of five cloned human muscarinic receptor subtypes," J. Pharmacol. Exp. Ther., 256:727-733 (1991).
Dowling, "Neural and Photochemical Mechanisms of Visual Adaptation in the Rat," Journal of General Physiology, 46(6):1287-1291 (1963).
Drysdale et al., "Complex Promoter and Coding Region Beta 2-adrenergic Receptor Haplotypes Alter Receptor Expression and Predict in vivo Responsiveness," Proc Natl Acad Sci USA, 97(19):10483-10488 (2000).
Egger, et al., "Keratinocyte growth factor ameliorates dextran sodium sulfate colitis in mice," Dig Dis Sci, 44(4): 836-44 (Apr. 1999).
Ellis et al., "Multiple Doses of Trodusquemine Improve Glucose Tolerance in Type 2 Diabetic Subjects," 69th Scientific Sessions of the American Diabetes Association, Abstract No. 2071-PO (2009).

(56) References Cited

OTHER PUBLICATIONS

Ellman et al., "A new and rapid colorimetric determination of acetylcholinesterase activity," Biochem. Pharmacol., 7: 88-95 (1961).
Erdos et al., "Neutral endopeptidase 24.11 (enkephalinase) and related regulators of peptide hormones," FASEB J. 3:145 (1989).
Ermolieff et al., "Proteolytic activation of recombinant pro-memapsin 2 (pro-beta-secretase) studied with new fluorogenic substrates," Biochemistry, 39:12450-12456 (2000).
Escalera et al., "Succinic semialdehyde dehydrogenase deficiency: decrease in 4-OH-butyric acid levels with low doses of vigabatrin," An Pediatr (Barc). 72(2):128-32 (2010).
Esterbauer et al., "Chemistry and Biochemistry of 4-Hydroxynonenal, Malonaldehyde and Related Aldehydes," Free Radic Biol Med, 1991; 11:81-128.
Everest-Todd, "Topical Application of Cyclodextrin Ethers in the Control of Pain," Proceedings of the Eighth International Symposium on Cyclodextrins, pp. 495-498 (1998).
Farid et al., "Detection of corneal fibrosis by imaging second harmonic-generated signals in rabbit corneas treated with mitomycin C after excimer laser surface ablation," Invest Ophthalmol Vis Sci. 2008;49(10):4377-83.
FDA, "Bam R59: Phosphate-Buffered Saline (PBS), pH 7.4," Jan. 2001, retrieved online at <http://www.fda.gov/Food/FoodScienceR.esearch/LaboratoxyMethods/ucm062268.htm> on Apr. 18, 2015 (1 page).
Feighner et al., "Receptor for motilin identified in the human gastrointestinal system," Science, 284:2184-2188 (1999).
Fernandes et al., "Characterization of angiotensin-converting enzymes 1 and 2 in the soleus and plantaris muscles of rats," Braz J Med Biol Res., 43:837-842 (2010).
Ferry et al., "Binding of prostaglandins to human PPAR?: Tool assessment and new natural ligands," Eur. J. Pharmacol., 417:77-89 (2001).
Feve et al., "Transcriptional down-regulation by insulin of the beta 3-adrenergic receptor expression in 3T3-F442A adipocytes: a mechanism for repressing the cAMP signaling pathway," Proc Natl Acad Sci USA. 91:5677 (1994).
Fiske et al., "The Colormetric Determination of Phosphorus," J. Biol. Chem., 66:375-400 (1925).
Fitzmaurice et al., "Aldehyde dehydrogenase inhibition as a pathogenic mechanism in Parkinson disease," Proc. Natl Acad Sci U.S.A, 110(2):636-641 (2013).
Ford et al., "Pharmacological pleiotropism of the human recombinant alpha1A-adrenoceptor: implications for alpha1-adrenoceptor classification," Brit. J. Pharmacol., 121:1127-1135 (1997).
Fowler et al., "Coloured Complexes of all-trans-retinal with Benzocaine and Other Local Anesthetics," J Photochem Photobiol B, 8(2):183-188 (1991).
Frantz et al., "The Activation State of p38 Mitogen-Activated Protein Kinase Determines the Efficiency of ATP Competition for Pyridinylimidazole Inhibitor Binding," Biochemistry, 37:13846-13853 (1998).
Friesen et al., "Optimization of a Tertiary Alcohol Series of Phosphodiesterase-4 (PDE4) Inhibitors: Structure-Activity Relationship Related to PDE4 Inhibition and Human Ether-a-go-go Related Gene Potassium Channel Binding Affinity," J. Med. Chem., 46(12):2413-2426 (2003).
Fuchs et al., "Functional characterization of three mutations of the endothelin B receptor gene in patients with Hirschsprung's disease: evidence for selective loss of Gi coupling," Mol. Med., 7:115-124 (2001).
Fukunaga et al., "Single nucleotide polymorphism of human platelet-activating factor receptor impairs G-protein activation," J. Biol. Chem., 276:43025-43030 (2001).
Full 1H NMR assignment for RAL-NS2 in CDCIJ, submitted to Japanese Patent Office Mar. 1, 2012.
Ganapathy et al., "Molecular and ligand-binding characterization of the sigma-receptor in the Jurkat human T lymphocyte cell line," JPET, 289:251-260 (1999).
Gasper et al., "2-Hydroxypropyl-beta-cyclodextrin (HPßCD) reduces age-related lipofuscin accumulation through a cholesterol-associated pathway," Scientific Reports, 2017; 7(2197):1-7.
Gibson et al., "Stable isotope dilution analysis of 4-hydroxybutyric acid: an accurate method for quantification in physiological fluids and the prenatal diagnosis of 4-hydroxybutyric aciduria," Biomed Environ Mass Spectrom., 19(2):89-93 (1990).
Gibson et al., "Stable-isotope dilution analysis of D- and L-2-hydroxyglutaric acid: application to the detection and prenatal diagnosis of D- and L-2-hydroxyglutaric acidemias," Pediatr Res., 34(3):277-80 (1993).
Gibson et al., "The Aldehyde Trap NS2 Mitigates Dense Haze in a Rabbit Model of Photorefractive Keratectomy" ARVO Annual Meeting Abstract, 1 page (Jun. 2015).
Godard et al., "Sur les orthoamino formyl quinoleines, nouveaux synthons heterocycliques," J Heterocyclic Chem, 17(3):465-473 (1980).
Goldstein et al., "A Phase 2 Exploratory Study of a Novel Interleukin-1 Receptor Inhibitor (EBI-005) in the Treatment of Moderate-to-Severe Allergic Conjunctivitis," Eye Contact Lens, 2015; 41(3):145-55.
Gole et al., "Plasma Proteins Modified by Tyrosine Nitration in Acute Respiratory Distress Syndrome," Am J Physiol Lung Cell Mol Physiol, 2000, vol. 278, pp. L961-L967.
Gomez, "Dimethyltin(IV) 2,6-disubstituted pyridine complexes," J. Organometallic Chemistry, 672(2):115-122 (2003).
Good, "Measuring field loss in children administered vigabatrin: a problem in search of a solution," JAAPOS. 15(5):411-2 (2011).
Gopalakrishnan et al., "Stable expression, pharmacologic properties and regulation of the human neuronal nicotinic acetylcholine alpha 4 beta 2 receptor," J. Pharmacol. Exp. Ther., 276:289-297 (1996).
Gould et al., "[3H]nitrendipine-labeled calcium channels discriminate inorganic calcium agonists and antagonists," Proc. Natl. Acad. Sci. U.S.A., 79:3656-3660 (1982).
Grandy et al., "Cloning of the cDNA and gene for a human D2 dopamine receptor," Proc. Natl. Acad. Sci. U.S.A., 86:9762-9766 (1989).
Green et al., "Characterization of [(3)H]-CGP54626A binding to heterodimeric GABA(B) receptors stably expressed in mammalian cells," Brit. J. Pharmacol., 131:1766-1774 (2000).
Green et al., "Influence of Various Agents on Corneal Permeability," American Journal of Ophthalmology, 1971; 72(5):897-905.
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950).
Gromachevskaya et al., "4H-3,1-benzoxazines. 2. Synthesis of 2,4-substituted 1 2-dihydro-4H-3,1-benzoxazines," Chemistry of Heterocyclic Compounds, 24(6):692-697 (Jun. 1988).
Grotto et al., "Importance of the lipid peroxidation biomarkers and methodological aspects for malondialdehyde quantification," Quim Nova, 2009; 32(1):169-174.
Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, 2 pages (Jul. 2018).
Hampson et al., "Cannabidiol and (−)Delta9-tetrahydrocannabinol are neuroprotective antioxidants," Proc. Nat. Acad. Sci 95:8268-8273 (1998).
Hassan et al., "Oxidative stress in systemic lupus erythematosus and rheumatoid arthritis patients: relationship to disease manifestations and activity," International Journal of Rheumatic Diseases, 14(1):325-331 (2011).
Herbort et al., "Endotoxin-induced uveitis in the rat," Graefe's Arch Clin Exp Ophthalmol, 1988; 226:553-8.
Hessen et al., "Dry Eye: an Inflammatory Ocular Disease," J Ophthalmic Vis Res, 2014; 9(2):240-250.
Heuillet et al., "Characterization of a Human NK1 Tachykinin Receptor in the Astrocytoma Cell Line U 373 MG," J. Neurochem., 60:868-876 (1993).
Highlights of Prescribing Information, Bridion® (sugammadex) Injection, for intravenous use, Initial U.S. Approval: 2015, Last Revised Dec. 2015 (19 pages).

(56) References Cited

OTHER PUBLICATIONS

Hogema et al., "Pharmacologic rescue of lethal seizures in mice deficient in succinate semialdehyde dehydrogenase," Nat Genet. 29:212-16 (2001).
Hom et al., "Allergic conjunctivitis and dry eye syndrome," Ann Allergy Asthma Immunol, 2012; 108(3):163-6.
Hong et al., "Laboratory Scale Production of Injectable Liposomes By Using Cell Disruptor . . . ," Journal of Pharmaceutical Investigation, 2015, vol. 45, pp. 73-78.
Hope et al., "Characterization of a human 5-hydroxytryptamine3 receptor type A (h5-HT3R-AS) subunit stably expressed in HEK 293 cells," Brit. J. Pharmacol., 118:1237-1245 (1996).
Horner et al., "Analogs of 3-Amino-7-chloro-1,2,4-benzotriazine 1-Oxide as Antimalarial Agents," J. Med. Chem., 11(5):946-949 (1968).
Hoyer et al., "Characterization of the 5-HT1B recognition site in rat brain: binding studies with (-)[125]iodocyanopindolol," Eur. J. Pharmacol., 118:1-12 (1985).
Huang et al., "Characterization of Calcium Phosphate Nanoparticles Based on a PEGylated Chelator for Gene Delivery," ACS Appl Mater Interfaces, 9:10435?10445 (Mar. 2017).
Huang et al., "Identification of human Ether-a-go-go related gene modulators by three screening platforms in an academic drug-discovery setting," Assay Drug Dev Technol., 8(6):727-42 (2010).
Huang et al., "Novel peptide inhibitors of angiotensin-converting enzyme 2," J. Biol. Chem., 278:15532-15540 (2003).
Hubbard, "Geometrical Isomerization of Vitamin A, Retinene and Retinene Oxime," Journal of the American Chemical Society, 78(18):4662-4667 (1956).
Hugues et al., "Preparation of a pure monoiodo derivative of the bee venom neurotoxin apamin and its binding properties to rat brain synaptosomes," J. Biol. Chem., 257:2762-2769 (1982).
Hurd et al., "Reaction of Propiolactone with Aniline Derivatives," Journal of the American Chemical Society, 74(23):5889-5893 (1952).
Inoue et al., "Filter-binding assay procedure for thyroid hormone receptors," Anal Biochem. 134(1):176 (1983).
Iriyama et al., "A2E, a pigment of the lipofuscin of retinal pigment epithelial cells, is an endogenous ligand for retinoic acid receptor," J Biol Chem., 283(18):11947-53 (2008) Epub Mar. 6, 2008.
Irons, "Fluvoxamine in the treatment of anxiety disorders," Neuropsychiatr Dis Treat. 2005;1(4):289-99.
Ishida et al., "Stabilization of calmodulin-dependent protein kinase II through the autoinhibitory domain," J. Biol. Chem., 270:2163-2170 (1995).
Ito et al., "A Medium-Term Rat Liver Bioassay for Rapid in vivo Detection of Carcinogenic Potential of Chemicals," Cancer Science, 94(1):3-8 (2003).
Itokawa et al., "Antiangiogenic effect by SU5416 is partly attributable to inhibition of Flt-1 receptor signaling," Mol. Cancer Ther., 1:295-302 (2002).
Jacobs et al., "Responses to ragweed pollen in a pollen challenge chamber versus seasonal exposure identify allergic rhinoconjunctivitis endotypes," J. Allergy Clin. Immunol., 2012; 130(1):122-7.
Jafari et al., "Evaluation of plasma, erythrocytes, and bronchoalveolar lavage fluid antioxidant defense system in sulfur mustard-injured patients," Clin Toxicol (Phila)., 48(3):184-92 (2010).
Janowski et al., "Structural requirements of ligands for the oxysterol liver X receptors LXRalpha and LXRbeta," Proc. Natl. Acad. Sci. USA, 96:266-271 (1999).
Jarrett et al., "Mitochondrial DNA damage and impaired base excision repair during epileptogenesis," Neurobiology of Disease, 30(1):130-138 (2008).
Jellinger et al., "American Association of Clinical Endocrinologists and American College of Endocrinology Guidelines for Management of Dyslipidemia and Prevention of Cardiovascular Disease," Endocr Pract. 2017;23(Suppl 2):1-87.
Ji et al., "Exploration of diverse hinge-binding scaffolds for selective Aurora kinase inhibitors," Bioorg. & Med. Chem. Let. 22:4528 (2012).
Johannsdottir et al., "Development of a Cyclodextrin-Based Aqueous Cyclosporin A Eye Drop Formulations," International Journal of Pharmaceutics, 2015; 493(1-2):86-95.
Johnson et al., "2-Hydroxypropyl-ß-Cyclodextrin Removes All-Trans Retinol from Frog Rod Photoreceptors in a Concentration-Dependent Manner," Journal of Ocular Pharmacology and Therapeutics, 2010; 26(3):245-248.
Joseph et al., "Binding of (-)-[3H]-CGP12177 at two sites in recombinant human beta 1-adrenoceptors and interaction with beta-blockers," Naun.-Sch. Arch. Pharm., 369:525-532 (2004).
Kam et al., "Topical Cyclodextrin Reduces Amyloid Beta and Inflammation Improving Retinal Function in Ageing Mice," Experimental Eye Research, 2015; 135:59-66.
Kamino et al., "Deficiency in mitochondrial aldehyde dehydrogenase increases the risk for late-onset Alzheimer's disease in the Japanese population," Biochemical and Biophysical Research Communications, 273(1):192-196 (2000).
Karahashi et al., "Changes of caspase activities involved in apoptosis of a macrophage-like cell line J774.1/JA-4 treated with lipopolysaccharide (LPS) and cycloheximide," Biol. Pharm. Bull., 23:140-144 (2000).
Karan et al., Lipofuscin Accumulation, Abnormal Electrophysiology, and Photoreceptor Degeneration in Mutant ELOVL4 Transgenic Mice: A Model for Macular Degeneration, Proc Natl Acad Sci USA, 102(11):4164-4169 (2005).
Katugampola et al., "[(125)I]-(Pyr(1))Apelin-13 is a novel radioligand for localizing the APJ orphan receptor in human and rat tissues with evidence for a vasoconstrictor role in man," Brit. J. Pharmacol., 132:1255-1260 (2001).
Keister et al., "Inflammatory Bowel Disease and Irritable Bowel Syndrome Similarities and Differences," Crohn's & Colitis Foundation of America 2014.
Kenney et al., "The Cascade Hypothesis of Keratoconus," Contact Lens & Ant Eye, 26:139-146 (2003).
Keri, "Rosacea," Merck Manual, Professional Version, https://www.merckmanuals.com/professional/dermatologic-disorders/acne-and-related-disorders/rosacea, 7 pages (2017).
Knapp et al., "Intraocular Availability of Topically Applied Mycophenolate Mofetil in Rabbits," J. Ocul. Pharmacol. Ther., 2003; 19(2):181-192.
La Rosa et al., "Allergic conjunctivitis: a comprehensive review of the literature," Ital J Pediatr, 2013; 39:18.
Landor et al., "Allenes. Part 49, 4-Amino-2-(1-hydroxyalkyl)quinolones from Phenylhydroxylamine and Allenic Nitrites," J Chem Soc Perkin Trans 1, pp. 251-254 (1989).
Langin et al., "[3H]RX821002: a new tool for the identification of alpha 2A-adrenoceptors," Eur. J. Pharmacol., 167: 95-104 (1989).
Lankin et al., "Role of Oxidative Stress in the Genesis of Atherosclerosis and Diabetes Mellitus: A Personal Look Back on 50 Years of Research," Curr. Aging Sci. 10:18 (2017).
Le et al., "Ligand binding and functional properties of human angiotensin AT1 receptors in transiently and stably expressed CHO-K1 cells," Eur. J. Pharmacol., 513:35-45 (2005).
Lee et al., "Human recombinant soluble guanylyl cyclase: expression, purification, and regulation," Proc. Natl. Acad. Sci. USA, 97(20):10763-10768 (2000).
Lee et al., "The human brain cholecystokinin-B/gastrin receptor. Cloning and characterization," J. Biol. Chem., 268: 8164-8169 (1993).
Leibundgut et al., "Oxidation-specific epitopes and immunological responses: Translational biotheranostic implications for atherosclerosis," Current Opinion in Pharmacology, 13(2):168-179 (2013).
Leonardi et al., "Correlation Between Conjunctival Provocation Test (CPT) and Systemic Allergometric Tests in Allergic Conjunctivitis," Eye, 1990; 4:760-764.
Leonardi, "Allergy and allergic mediators in tears," Exp. Eye Res., 2013; 117:106-17.
Leurs et al., "Pharmacological characterization of the human histamine H2 receptor stably expressed in Chinese hamster ovary cells," Brit. J. Pharmacol., 112: 847-854 (1994).
Levey et al., "A new equation to estimate glomerular filtration rate," Ann Intern Med. 2009;150(9):604-12.

(56) References Cited

OTHER PUBLICATIONS

Levin et al., "The myocardium-protective Gly-49 variant of the beta 1-adrenergic receptor exhibits constitutive activity and increased desensitization and down-regulation," J. Biol.Chem., 277:30429-30435 (2002).

Lewin et al., "meta- and para-isothiocyanato-t-butylbicycloorthobenzoate: irreversible ligands of the gamma-aminobutyric acid-regulated chloride ionophore," Mol. Pharmacol., 35:189-194 (1989).

Li et al., "Effect of Vitamin A Supplementation on Rhodopsin Mutants Threonine-17 -> Methionine and Proline-347 -> Serine in Transgenic Mice and in Cell Cultures," Proc Natl Acad Sci USA, 95(20):11933-11938 (1998).

Liang et al., "Ocular safety of cationic emulsion of cyclosporine in an in vitro corneal wound-healing model and an acute in vivo rabbit model," Mol Vis, 2012; 18:2195-204.

Liu et al., "Comparison of human, mouse, rat, and guinea pig histamine H4 receptors reveals substantial pharmacological species variation," J. Pharmacol. Exp. Ther., 299:121-130 (2001).

Loftsson et al., "Cyclodextrin Microparticles for Drug Delivery to the Posterior Segment of the Eye: Aqueous Dexamethasone Eye Drops," Journal of Pharmacy and Pharmacology, 2007; 59(5):629-635.

Loftsson et al., "Cyclodextrins in Eye Drop Formulations: Enhanced Topical Delivery of Corticosteroids to the Eye," Acta Ophthalmologica Scandinavica, 2002; 80(2):144-150.

Lopachin et al., "Molecular mechanisms of aldehyde toxicity: a chemical perspective," Chem Res Toxicol, 2014; 27(7):1081-91.

Lovenberg et al., "Cloning and functional expression of the human histamine H3 receptor," Mol. Pharmacol., 55:1101-1107 (1999).

Lukas, R.J., "Characterization of curaremimetic neurotoxin binding sites on membrane fractions derived from the human medulloblastoma clonal line, T15671," J. Neurochem., 46:1936-1941 (1986).

Luthin et al., "Characterization of two affinity states of adenosine A2a receptors with a new radioligand, 2-[2-(4-amino-3-[125I]iodophenyl)ethylamino]adenosine," Mol. Pharmacol., 47:307-313 (1995).

MacDonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).

MacDonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).

MacDonald et al., "Molecular characterization of the melanin-concentrating hormone/receptor complex: identification of critical residues involved in binding and activation," Mol. Pharmacol., 58:217-225 (2000).

MacDonald et al., "Novel Small Molecule Aldehyde Sequestering Agents Demonstrate Broad Therapeutic Potential for Ocular Inflammation," ARVO Annual Meeting Abstract, 2 pages (Jul. 2018).

MacDonald et al., "The novel aldehyde trap, ADX-102, reduces inflammation-mediated lung infilrate in a mouse model of LPS-induced acute lung injury," 13th World Congress on Inflammation Abstract, p. 192 (Jul. 2017).

MacKenzie et al., "Characterization of the human dopamine D3 receptor expressed in transfected cell lines," Eur. J. Pharmacol., 266:79-85 (1994).

Maeda et al., "Involvement of All-trans-retinal in Acute Light-induced Retinopathy of Mice," J Biol Chem, 284(22):15173-83 (May 2009).

Maeda et al., "Primary amines protect against retinal degeneration in mouse models of retinopathies," Nat Chem Biol, 2011; 8(2):170-178.

Maguire et al., "Orphan-receptor ligand human urotensin II: receptor localization in human tissues and comparison of vasoconstrictor responses with endothelin-1," Brit. J. Pharmacol., 131:441-446 (2000).

Malondialdehyde, Wikipedia, 2008, retrieved from the internet on Aug. 4, 2021 at https://en.wikipedia.org/wiki/Malondialdehyde.

Malondialdehyde, Wikipedia. Edited 2020; Accessed 2021: https://en.wikipedia.org/w/index.php?title=Malondialdehyde&oldid=993228459.

Mandell et al., "The Aldehyde Trap NS2 Reduces Ocular Inflammation in an Endotoxin-Induced Model in Rats," ARVO Annual Meeting Abstract, 2 pages (Jun. 2015).

Mandell et al., "The Aldehyde Trap NS2 Reduces Ocular Inflammation in an Endotoxin-Induced Model in Rats," Investigative ophthalmology & visual science. 2015; 56(7):3095.

Mantey et al., "Discovery of a high affinity radioligand for the human orphan receptor, bombesin receptor subtype 3, which demonstrates that it has a unique pharmacology compared with other mammalian bombesin receptors," J. Biol. Chem., 272:26062-26071 (1997).

Marnett, "Oxy radicals, lipid peroxidation and DNA damage," Toxicology, 181-182:219-222 (2002).

Martin et al., "Molecular cloning and functional characterization of murine cysteinyl-leukotriene 1 (CysLT(1)) receptors.," Biochem. Pharmacol., 62:1193-1200 (2001).

Matern et al., "Seizures in a boy with succinic semialdehyde dehydrogenase deficiency treated with vigabatrin (gamma-vinyl-GABA)," J Inherit Metab Dis., 19(3):313-8 (1996).

Mathew et al., "Updates in the management of diabetic macular edema," J Diabetes Res. 2015; 2015:794036.

Maurice et al., "Advances in targeting cyclic nucleotide phosphodiesterases," Nat Rev Drug Discov., 2014; 13:290-314.

McCord et al., "Superoxide dismutase. An enzymic function for erythrocuprein (hemocuprein).," J. Biol. Chem., 1969; 244: 6049-6055.

McGinnity et al., "Evaluation of fresh and cryopreserved hepatocytes as in vitro drug metabolism tools for the prediction of metabolic clearance." Drug Metab. Dispos., 32(11):1247-1253 (2004).

McLaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," Clinical Science, 2015; 34(10):1245-1251.

Medline Plus. Macular Degeneration—age-related. (6 pages) (2013).

Meijer et al., "Biochemical and cellular effects of roscovitine, a potent and selective inhibitor of the cyclin-dependent kinases cdc2, cdk2 and cdk5," Eur. J. Biochem., 243:527-536 (1997).

Meng et al., "Cloning and pharmacological characterization of a rat kappa opioid receptor," Proc. Natl. Acad. Sci. U.S.A., 90:9954-9958 (1993).

Merck Sharp & Dohme Corp., "Bridion® (sugammadex) Injection Prescribing Information, for intravenous use," Highlights of Prescribing Information. 2015.

Mialet et al., "Isolation of the serotoninergic 5-HT4(e) receptor from human heart and comparative analysis of its pharmacological profile in C6-glial and CHO cell lines," Brit. J. Pharmacol., 129:771-781 (2000).

Miceli et al., "Efficacy of keratinocyte growth factor-2 in dextran sulfate sodium-induced murine colitis," J Pharmacol Exp Ther, 290(1):464-71 (Jul. 1999).

Mishra et al., "Recent Patents and Emerging Therapeutics in the Treatment of Allergic Conjunctivitis," Recent Pat. Inflamm. Allergy Drug Discov.; 2011; 5(1):26-36.

Mittl et al., "Structure of recombinant human CPP32 in complex with the tetrapeptide acetyl-Asp-Val-Ala-Asp fluoromethyl ketone," J. Biol. Chem., 272:6539-6547 (1997).

Monaghan et el., "The distribution of [3H]kainic acid binding sites in rat CNS as determined by autoradiography," Brain Res., 252:91-100 (1982).

Monsma et al., "Cloning and expression of a novel serotonin receptor with high affinity for tricyclic psychotropic drugs," Mol. Pharmacol., 43:320-327 (1993).

Mulheron et al., "Human 5-HT1A receptor expressed in insect cells activates endogenous G(o)-like G protein(s)," J. Biol. Chem., 269:12954-12962 (1994).

Muller-Enoch et al., "[6.7-Dihydroxycoumarin (Aesculetin) as a substrate for catechol-o-methyltransferase (author's transl)]," Z. Naturforsch., 31:280-284 (1976).

(56) References Cited

OTHER PUBLICATIONS

Munro et al., "Molecular characterization of a peripheral receptor for cannabinoids," Nature, 365:61-65 (1993).
Murphy et al., "Characterization of quisqualate recognition sites in rat brain tissue using DL-[3H]alpha-amino-3-hydroxy-5-methylisoxazole-4-propionic acid (AMPA) and a filtration assay," Neurochem. Res., 12:775-781 (1987).
Na et al., "Molecular profiling of a 6-hydroxydopamine model of Parkinson's disease," Neurochem Res. 2010;35(5):761-72.
Nagai et al., Improved corneal toxicity and permeability of tranilast by the preparation of ophthalmic formulations containing its nanoparticles, J Oleo Sci, 2014; 63(2):177-86.
Nagase et al., "Design and characterization of a fluorogenic substrate selectively hydrolyzed by stromelysin 1 (matrix metalloproteinase-3)," J. Biol. Chem., 269:20952-20957 (1994).
Nakamura et al., "Involvement of Oxidative Stress on Corneal Epithelial Alterations in a Blink-Suppressed Dry Eye," Investigative Ophthalmology and Visual Science, 2007; 48(4):1552-1558.
Negre-Salvayre et al., "Advanced Lipid Peroxidation End Products in Oxidative Damage to Proteins. Potential Role in Diseases and Therapeutic Prospects for the Inhibitors," Br J Pharmacol, 2008; 153(1):6-20.
Nema et al., "Excipients and Their Use in injectable Products," PDA J Pharm Sci Technol, 51(4):166-171 (1997).
Nerurkar et al., "13-Aryl-Glutaconic Acids. II. Imides of Certain 13-aryl-Glutaconic and Glutaric Acids," J Org Chem, 24(12):2055-2056 (1959).
Nerurkar et al., "Beta-Arylglutaconic Acids. II. Imides of Certain Beta-Arylglutaconic and Glutaric Acids," J Org Chem, 24(12):2055-2056 (1959).
Nielsen and Bundgaard, "Glycolamide esters as biolabile prodrugs of carboxylic acid agents: synthesis, stability, bioconversion, and physicochemical properties," J Pharm Sci. 1988;77(4):285-98.
Niwa et al., "Protein oxidative damage in the stratum corneum: Evidence for a link between environmental oxidants and the changing prevalence and nature of atopic dermatitis in Japan," Br J Dermatol., 2003; 149:248.
Nociari et al., "Beta cyclodextrins bind, stabilize, and remove lipofuscin bisretinoids from retinal pigment epithelium," Proc Natl Acad Sci U.S.A., 2014; E1402-E1408.
Noorwez et al., "Pharmacological Chaperone-mediated in Vivo Folding and Stablization of the P23H-Opsin Mutant Associated with Autosomal Dominant Retinitis Pigmentosa," J Biol Chem, 278:14442-14450 (2003).
O'Brien et al., "Aldehyde Sources, Metabolism, Molecular Toxicity Mechanisms, and Possible Effects on Human Health," Crit Rev Toxicol, 2005; 35:609-662.
O'Regan et al., "Filaggrin in atopic dermatitis," J Allergy Clin Immunol. 2009;124(3 Suppl 2):R2-6.
Obourn et al., "Hormone- and DNA-binding mechanisms of the recombinant human estrogen receptor," Biochemistry 32(24):6229 (1993).
Okayasu et al., "A novel method in the induction of reliable experimental acute and chronic ulcerative colitis in mice," Gastroenterology. 1990;98(3):694-702.
Organisciak et al., "Susceptibility to Retinal Light Damage in Transgenic Rats with Rhodopsin Mutations," Invest Ophthalmol Vis Sci, 44(2):486-492 (2003).
Ousler et al., "Use of the Controlled Adverse Environment (CAE) in Clinical Research: A Review," Opthalmology and Therapy, Sep. 27, 2017, vol. 6, pp. 263-276.
Pacholczyk et al., "Expression cloning of a cocaine- and antidepressant-sensitive human noradrenaline transporter," Nature, 350:350-354 (1991).
Pal et al., "Sulfur mustard analog induces oxidative stress and activates signaling cascades in the skin of SKH-1 hairless mice," Free Radic Biol Med., 47(11):1640-51 (2009).
Palchaudhuri et al., "Corticotropin-releasing factor receptor type 1 from Tupaia belangeri-cloning, functional expression and tissue distribution," Eur. J. Biochem., 258:78-84 (1998).
Parish et al., "Isolation and One-Step Preparation of A2E and iso-A2E, Fluorophores from Human Retinal Pigment Epithelium," Proc Natl Acad Sci USA, 95(25):14609-14613 (1998).
Park et al., "Modulation of Acute Inflammation and Keratocyte Death by Suturing, Blood, and Amniotic Membrane in PRK," Invest. Opthalmol Vis Sci. 2000;41(10):2906-14.
Park et al., "Homogeneous proximity tyrosine kinase assays: scintillation proximity assay versus homogeneous time-resolved fluorescence," Anal. Biochem., 269:94-104 (1999).
Parracho et al., "Differences between the gut microflora of children with autistic spectrum disorders and that of healthy children," Journal of Medical Microbiology, 54:987-991 (2005).
Patel C.Y., "Subtype selectivity of peptide analogs for all five cloned human somatostatin receptors (hsstr 1-5)," Endocrinology, 135:2814-2817 (1994).
PCT International Search Report from PCT/US2010/059719, Feb. 8, 2011.
PCT International Search Report from PCT/US2014/012762, Jul. 18, 2014.
PCT International Search Report from PCT/US2016/048054, Nov. 4, 2016.
PCT International Search Report from PCT/US2016/048064, Nov. 15, 2016.
PCT International Search Report from PCT/US2017/020020, May 24, 2017.
PCT International Search Report from PCT/US2017/031808, Aug. 11, 2017.
PCT International Search Report from PCT/US2017/047958, Oct. 31, 2017.
PCT International Search Report from PCT/US2018/023000, Jun. 1, 2018.
PCT International Search Report from PCT/US2019/041942, Sep. 30, 2019.
PCT International Search Report from PCT/US2019/045206, Oct. 17, 2019.
PCT International Search Report from PCT/US2019/054263, Jan. 6, 2020.
PCT International Search Report from PCT/US2019/064669, Feb. 27, 2020.
PCT International Search Report from PCT/US2020/024022, Jun. 17, 2020.
PCT International Search Report from PCT/US2020/031138, Jul. 13, 2020.
PCT International Search Report from PCT/US2020/031219, Aug. 31, 2020.
PCT International Search Report from PCT/US2021/023884, Jul. 28, 2021.
PCT International Search Report from PCT/US2021/032335, Jul. 27, 2021.
PCT International Search Report from PCT/US2021027148, Jun. 28, 2021.
PCT International Search Report from PCT/US2022/035898, Nov. 16, 2022.
Pellock, "Balancing clinical benefits of vigabatrin with its associated risk of vision loss," Acta Neurologica. Scandinavica. Supplementum., 124(s192):83-91 (2011).
Petroski et al., "Selective labeling of embryonic neurons cultured on astrocyte monolayers with 5(6)-carboxyfluorescein diacetate (CFDA)," Journal of Neuroscience Methods, 52(1):23-32 (1994).
Pfaar et al., "Perspectives in allergen immunotherapy: 2017 and beyond," Allergy, 2018; 73(Suppl 104):5-23.
Pontikis et al., "Cyclodextrin alleviates neuronal storage of cholesterol in Niemann-Pick C disease without evidence of detectable blood-brain barrier permeability," Journal of Inherited Metabolic Disease, 2013; 36(3):491-498.
Pozzi et al., "Modification of Collagen IV by Glucose or Methylglyoxal Alters Distinct Mesangial Cell Function," Journal of the American Society of Nephrology, 20:2119-2125 (2009).
Pred Forte Prescribing Information, Allergan, 5 pages (2017).
Pristupa et al., "Pharmacological heterogeneity of the cloned and native human dopamine transporter: disassociation of [3H]WIN 35,428 and [3H]GBR 12,935 binding.," Mol. Pharmacol., 45:125-135 (1994).

(56) References Cited

OTHER PUBLICATIONS

Pruneau et al., "LF 16.0335, a novel potent and selective nonpeptide antagonist of the human bradykinin B2 receptor," Brit. J. Pharmacol., 125:365-372 (1998).
Pubchem, 1824609-67-7, SID 333824451, Apr. 24, 2017 (6 pages).
Pubchem, 2-(3-Aminoquinolin-2-yl)propan-2-ol, CID 117758222, Feb. 23, 2016, modified Jun. 13, 2020 (11 pages).
Pubchem, SCHEMBL16316728, CID 117758222, Feb. 23, 2016, modified Sep. 30, 2017 (13 pages).
Roberts et al., "Experimental Organic Chemistry—A Miniscale Approach," copyright 1994 by Saunders College Publishing, pp. 580-581 and 584-586.
Roche, "Tween 20," Sigma-Aldrich Datasheet. Retrieved Nov. 19, 2020: https://www.sigmaaldrich.com/catalog/product/roche/11332465001?lang=en&region=US#:~:text=Tween%2020%>.
Rohrer et al., "Cloning and characterization of a fourth human somatostatin receptor," Proc. Natl. Acad. Sci. U.S.A., 90:4196-4200 (1993).
Roumen et al., "Serum Lipofuscin as a Prognostic Indicator of Adult Respiratory Distress Syndrome and Multiple Organ Failure," British Journal of Surgery, 1994, vol. 81, pp. 1300-1305.
Rønborg et al., "Exposure chamber for allergen challenge. The development and validation of a new concept," Allergy, 1996; 51(2):82-8.
Sahi et al., "Hepatocytes as a tool in drug metabolism, transport and safety evaluations in drug discovery." Current Drug Discov. Technol., 7(3):188-198 (2010).
Salvatore et al., "Molecular cloning and characterization of the human A3 adenosine receptor," Proc. Natl. Acad. Sci. U.S.A., 90:10365-10369 (1993).
Samsonov et al., "Impact of Atherosclerosis- and Diabetes-Related Dicarbonyls on Vascular Endothelial Permeability: A Comparative Assessment," Oxid. Med. Cell Longev. Article 1625130 (2017).
Sanchez et al., "Allergic Conjunctivitis," J Investig Allergol Clin Immunol., 2011; 21(2):1-19.
Sandikci et al., "Lipid Peroxidation and Antioxidant Defence System in Patients with Active or Inactive Behcet's Disease," Acta Derm Venereol, 2003; 83:342-346.
Sarafian et al., "Synergistic cytotoxicity of Delta(9)-tetrahydrocannabinol and butylated hydroxyanisole," Toxicology Letters, 133(2-3):171-179 (2002).
Sarfare et al., "Biocompatibility of a Synthetic Biopolymer for the Treatment of Rhegmatogenous Retinal Detachment," J Clin Exp Ophthalmol. 2015;6(5):475.
Sarup et al., "Resolution of high and low affinity progesterone receptors from human breast carcinoma T47D cells," J. Biol. Chem., 263:5624-5633 (1988).
Sasaki et al., "Retinal drug delivery using eyedrop preparations of poly-L-lysine-modified liposomes," Eur J Pharm Biopharm, 2013; 83(3):364-9.
Satici et al., "Malondialdehyde and antioxidant enzyme levels in the aqueous humor of rabbits in endotoxin-induced uveitis," Eur J Ophthalmol, 2003; 13(9-10):779-83.
Sayed et al., "Metabolic Activation of R,S-1-(Tetrahydro-2-furanyl)-5-fluorouracil (Ftorafur) to 5-fluorouracil by Soluble Enzymes," Cancer Research, 43:4039-4044 (1983).
Schaumberg et al., "Prevalence of dry eye syndrome among US women," Am J Ophthalmol. 2003;136(2):318-26.
Schaumberg et al., "Epidemiology of dry eye syndrome," Lacrimal Gland, Tear Film, and Dry Eye Syndromes 3, Kluwer Academic/Plenum Publishers, pp. 989-998 (2002).
Schaumberg et al., "Prevalence of Dry Eye Disease among US Men: Estimates from the Physicians' Health Studies," Arch Ophthalmol, 2009; 127(6):763-768.
Schioth et al., "Characterization of the binding of MSH-B, HB-228, GHRP-6 and 153N-6 to the human melanocortin receptor subtypes," Neuropeptides, 31:565-571 (1997).
Schramm et al., "The Cross-linked Biopolymer Hyaluronic Acid as an Artificial Vitreous Substitute," Invest Ophthalmol Vis Sci, 53(2):613-621 (Feb. 2012).

Schwartz and Work, "Measurement and estimation of GFR in children and adolescents," Clin J Am Soc Nephrol. 2009;4(11):1832-43.
Schwartz et al., "Tamponade in surgery for retinal detachment associated with proliferative vitreoretinopathy," Cochrane Database Syst Rev. 2020;5(5):CD006126.
Schwinn et al., "Molecular cloning and expression of the cDNA for a novel alpha 1-adrenergic receptor subtype," J. Biol. Chem., 265:8183-8189 (1990).
Sciuto et al., "Therapeutic Treatments of Phosgene-Induced Lung Injury," Inhal Toxicol, 16(8):565-580 (2004).
Search Report and Written Opinion issued by the Intellectual Property Office of Singapore for Singapore Patent Application No. 11201504859Y dated Aug. 1, 2016 (12 pages).
Serbecic et al., "Anti-oxidative vitamins prevent lipid-peroxidation and apoptosis in corneal endothelial cells," Cell Tissue Res, 320(3):465-75 (Jun. 2005).
Shank et al., "Ion and temperature effects on the binding of gamma-aminobutyrate to its receptors and the high-affinity transport system," J. Neurochem., 54:2007-2015 (1990).
Shen et al., "Molecular cloning and expression of a 5-hydroxytryptamine7 serotonin receptor subtype," J. Biol. Chem., 268:18200-18204 (1993).
Sheppard et al., "Targeting Anterior Uveitis: A Focus on Iontophoresis and Other Advanced Technologies," 2018.
Sheppard et al., "Targeting Anterior Uveitis: A Focus on Iontophoresis . . . ", Sep. 1, 2018, Retrieved from Internet URL: https://www.nyee.edu/files/NYEE/Health%20Professionals/Continuing%20Medical%20Education/Enduring%20CME%20Activities/158_supplement.small_v1_FINAL%20082818.pdf.
Sheppard et al., "A Randomized, Comparator-Controlled Phase 2 Clinical Trial of ADX-102 Ophthalmic Solution in Noninfectious Anterior Uveitis," ARVO Annual Meeting Abstract, Invest Ophth Vis Sci. 2017; 58(8):1231.
Sherman et al., "Cellular Defenses Against Unfolded Proteins: A Cell Biologist Thinks about Neurodegenerative Diseases," Neuron, 29(1):15-32 (2001).
Shipp et al., "Common acute lymphoblastic leukemia antigen (CALLA) is active neutral endopeptidase 24.11 ("enkephalinase"): direct evidence by cDNA transfection analysis," Proc Natl Acad Sci USA. 86:297 (1989).
Shoemaker et al., "[3H]diltiazem binding to calcium channel antagonists recognition sites in rat cerebral cortex," Eur. J. Pharmacol., 111:273-277 (1985).
Siegrist et al., "Radioreceptor assay for alpha-MSH using mouse B16 melanoma cells+.," J. Recep. Res., 8:323-343 (1988).
Sieving et al., "Inhibition of the Visual Cycle in vivo by 13-cis Retinoic Acid Protects from Light Damage and Provides a Mechanism for Night Blindness in Isotretinoin Therapy," Proc Natl Acad Sci USA, 98(4):1835-1840 (2001).
Sills et al., "[3H]CGP 39653: a new N-methyl-D-aspartate antagonist radioligand with low nanomolar affinity in rat brain," Eur. J. Pharmacol., 192:19-24 (1991).
Simeone et al., "Modification of the Pyridine Moiety of Non-peptidyl Indole GnRH Receptor Antagonists," Bioorganic & Medicinal Chemistry Letters, 12(22):3329-3332 (2002).
Simonin et al., "The human delta-opioid receptor: genomic organization, cDNA cloning, functional expression, and distribution in human brain," Mol. Pharmacol., 46:1015-1021 (1994).
Singh et al., "The epidemiology of ocular and nasal allergy in the United States, 1988-1994," J. Allergy Clin. Immunol., 2010; 126(4):778-783.
Smit et al., "Regulation of the human histamine H1 receptor stably expressed in Chinese hamster ovary cells," Brit. J. Pharmacol., 117:1071-1080 (1996).
Smith and Cass, "Oxidative stress and dopamine depletion in an intrastriatal 6-hydroxydopamine model of Parkinson's disease," Neuroscience. 2007;144(3):1057-66.
Smith et al., "Basic pathogenic mechanisms operating in experimental models of acute anterior uveitis," Immunol Cell Biol, 1998; 76:497-512.
Snead et al., "Gamma-hydroxybutyric acid," New England Journal of Medicine, 352(26):2721-2732 (2005).

(56) References Cited

OTHER PUBLICATIONS

Snell et al., "Novel structure having antagonist actions at both the glycine site of the N-Methyl-D-Aspartate receptor and neuronal voltage-sensitive sodium channels. Biochemical, electrophysiological, and behavioral characterization," J Pharmacol Exp Ther, 292(1):215-227 (2000).
Spadea et al., "Corneal wound healing after laser vision correction," Br J Ophthalmol. 2016; 100:28-33.
Spagnol et al., "Efficient synthesis of tricyclic benzobisoxazines by silica gel catalysis," J Org Chem, 2;72(5):1867-1869 (Mar. 2007).
Sparrow et al. "Phospholipid meets all-trans-retinal: the making of RPE bisretmoids," Journal of Lipid Research, 51: 247-261 (2010).
Speth et al., "Benzodiazepine receptors: temperature dependence of [3H]flunitrazepam binding," Life Sci., 24:351-358 (1979).
Stefansson and Loftsson, "Cyclodextrins in Eye Drop Formulations," J Incl Phenom Macrocycl Chem. 2002;44:23-27(abstract).
Stehle et al., "Molecular cloning and expression of the cDNA for a novel A2-adenosine receptor subtype," Mol. Endocrinol., 6:384-393 (1992).
Stevenson et al., "Dry eye disease: an immune-mediated ocular surface disorder," Arch Ophthalmol. 2012; 130(1): 90-100.
Struys et al., "Determination of the GABA analogue succinic semialdehyde in urine and cerebrospinal fluid by dinitrophenylhydrazine derivatization and liquid chromatography-tandem mass spectrometry: application to SSADH deficiency," J Inherit Metab Dis., 28(6):913-20 (2005).
Struys et al., "Metabolism of gamma-hydroxybutyrate to d-2-hydroxyglutarate in mammals: further evidence for d-2-hydroxyglutarate transhydrogenase," Metabolism, 55(3):353-8 (2006).
Study showing effect of ADX-102 on Fibrotic Changes in Cardiac Fibroblasts Following Cell Stress, American Society for Cell Biology Annual Meeting, Dec. 3-7, 2016 (2 pages).
Sus et al., "Uber die Lichtreaktion der o-Chinondiazide V Mitteilungl) Ubergange heterocyclischer 6-Ringe in heterocyclische 5-Ringe," Liebigs Ann. Chem. 583:150 (1953).
Tahara et al., "Pharmacological characterization of the human vasopressin receptor subtypes stably expressed in Chinese hamster ovary cells," Brit. J. Pharmacol., 125:1463-1470 (1998).
Tang-Liu et al., "Effects of four penetration enhancers on corneal permeability of drugs in vitro," Journal of Pharmaceutical Sciences, 1994; 83(1):85-90.
Tatsumi et al., "Pharmacological profile of neuroleptics at human monoamine transporters," Eur. J. Pharmacol., 368: 277-283 (1999).
Tayeh et al., "Macrophage oxidation of L-arginine to nitric oxide, nitrite, and nitrate. Tetrahydrobiopterin is required as a cofactor," J. Biol. Chem., 264:19654-19658 (1989).
Tempest-Roe et al., "Local therapies for inflammatory eye disease in translation: past, present and future," BMC Ophthalmol., 2013; 13(1):39.
Tewari-Singh et al., "Silibinin attenuates sulfur mustard analog-induced skin injury by targeting multiple pathways connecting oxidative stress and inflammation," PLoS One 7(9):e46149 (2012).
Tian et al., "First total synthesis and determination of the absolute configuration of 1-N-methy1-3-methylamino-[N-butanoicacid-3-(9-methyl-8-propen-7-one)-amide]-benzo [f][1,7]naphthyridine-2-one, a novel benzonaphthyridine alkaloid," Tetrahedron Letters, 53:4892-4895 (2012).
Tikly et al., "Lipid peroxidation and trace elements in systemic sclerosis," Clinical Rheumatology, 25(3):320-324 (2006).
Torkildsen et al., "Efficacy and safety of olopatadine hydrochloride 0.77% in patients with allergic conjunctivitis using a conjunctival allergen-challenge model," Clinical Ophthalmology, 9:1703-1713 (2015).
Toth et al., "A simple, continuous fluorometric assay for HIV protease," Int. J. Pept. Protein Res., 36:544-550 (1990).
Tsugeno et al., "Regions of the molecule responsible for substrate specificity of monoamine oxidase A and B: a chimeric enzyme analysis," J. Biochem., 118 (5) 974-80 (1995).

Tsuzuki et al., "Molecular cloning and expression of the gene encoding human angiotensin II type 2 receptor.," Biochem. Biophys. Res. Commun., 200:1449-1454 (1994).
Tukozkan et al., "Measurement of Total Malondialdehyde in Plasma and tissues by High-Performance Liquid Chromatography and Thiobarbituric Acid Assay," Firat Tip Dergisi, 11 (2):88-92 (2006).
Turk et al., "Serum anti-carbonic anhydrase antibodies and oxidant-antioxidant balance in patients with acute anterior uveitis," Ocul Immunol Inflamm, 22(2):127-32 (Apr. 2014).
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Upadhyaya et al., "The sphingolipid degradation product trans-2-hexadecenal forms adducts with DNA," Biochem Biophy Res Comm., 424(1):18-21 (2012).
Vanachayangkul et al., "Inhibition of heme peroxidases by melamine," Enzyme Research, 2012:416062 (2012).
Vignon et al., "[3H]thienyl-phencyclidine ([3H]TCP) binds to two different sites in rat brain. Localization by autoradiographic and biochemical techniques," Brain Res., 378:133-141 (1986).
Vlaskina et al., "Novel Synthesis of Substituted Benzimidazoles by Reduction of Esters of 4-Alkylamino-3,5-dinitrobenzoic Acids by Tin Chloride," Chemistry of Heterocyclic Compounds, vol. 40(4):523-524 (2004).
Vogel et al., "Thirty years beyond discovery-clinical trials in succinic semialdehyde dehydrogenase deficiency, a disorder of GABA metabolism," J Inherit Metab Dis., 36(3):401-10 (2013).
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 277(5):3397-3403 (2002).
Wagner et al., "Omega-conotoxin GVIA binding to a high-affinity receptor in brain: characterization, calcium sensitivity, and solubilization," J. Neurosci., 8:3354-3359 (1988).
Wakamatsu et al., "Evaluation of lipid oxidative stress status and inflammation in atopic ocular surface disease," Mol Vis, 16:2465-75 (Nov. 2010).
Wall et al., "Plant Antitumor Agents. 30. Synthesis and Structure Activity of Novel Camptothecin Analogs," J. Med. Chem., 36(18):2689-2700 (1993).
Walter et al., "Novel Complex N-Heterocycles via Intramolecular 1,5-Electrocyclizations: 1,2,3,4,4a,5,5a,10-Octahydropyrido-[4",3":2',3']cyclobuta[1',2':4,5]pyrrolo[2,3-b]pyridines," Heterocycles, 48(8):1581-1591 (1998).
Wang et al., "A facile one-pot synthesis of 2-substituted-3-aminoquinolines: Preparation of benzo[b]naphthyridine-3-carbonitriles," Tetrahedron, 60(13):2937-2942 (2004).
Wang et al., "Human mu opiate receptor. cDNA and genomic clones, pharmacologic characterization and chromosomal assignment," FEBS Lett., 338:217-222 (1994).
Wang et al., "Markers of oxidative and nitrosative stress in systemic lupus erythematosus: correlation with disease activity," Arthritis and Rheumatism, 62(7):2064-2072 (2010).
Wang, X.K., "Pharmacological study on recombinant human GABA-A receptor complex containing alphas (leucine 155 to valine) combined with beta3gamma2s subunits," Acta. Pharmacol. Sin., 22:521-523 (2001).
Waslidge et al., "A colorimetric method for the determination of lipoxygenase activity suitable for use in a high throughput assay format," Anal. Biochem., 231:354-358 (1995).
Weaver et al., "The Th17 pathway and inflammatory diseases of the intestines, lungs, and skin," Annu. Rev. Pathol., 8:477-512 (2013).
Webb et al., "Intralesional cytokines in chronic oxazolone-induced contact sensitivity suggest roles for tumor necrosis factor alpha and interleukin-4," J Invest Dermatol, 111(1):86-92 (Jul. 1998).
Weishaar et al., "Multiple molecular forms of cyclic nucleotide phosphodiesterase in cardiac and smooth muscle and in platelets. Isolation, characterization, and effects of various reference phosphodiesterase inhibitors and cardiotonic agents," Biochem. Pharmacol., 35:787-800 (1986).
Weng et al., "Insights into the Function of Rim Protein in Photoreceptors and Etiology of Stargardt's Disease from the Phenotype in abcr Knockout Mice," Cell, 98(1):13-23 (1999).

(56) References Cited

OTHER PUBLICATIONS

Westphal et al., "Reactions with Pyridinium Pyruvic Acid Esters," Pharmazie 1976;31(11)770-773.

Westphal et al., "Reactions with Pryridinium Pyruvic Acid Esters," Pharmazie, 31(11)770-773 (1976) [English Translation].

Wieland et al., "Subtype selectivity and antagonistic profile of the nonpeptide Y1 receptor antagonist BIBP 3226," J. Pharmacol. Exp. Ther., 275:143-149 (1995).

Winfield and Richards, "Ophthalmic products," Pharmaceutical Practice, Churchill Livingstone. 2004;265-268.

Witt-Enderby et al., "Characterization and regulation of the human ML1A melatonin receptor stably expressed in Chinese hamster ovary cells," Mol. Pharmacol., 50:166-174 (1996).

Wolkenberg et al., "Design, synthesis, and evaluation of novel 3,6-diaryl-4-aminoalkoxyquinolines as selective agonists of somatostatin receptor subtype 2," J Med Chem, 54(7):2351-2358 (2011).

Wood et al., "Aldehyde Load in Ischemia-Reperfusion Brain Injury: Neuroprotection by Neutralization of reactive Aldehydes with Phenelzine," Brain Res, 1122(1):184-190 (2006).

Wood et al., "The concept of "aldehyde load" in neurodegenerative mechanisms: cytotoxicity of the polyamine degradation products hydrogen peroxide, acrolein, 3-aminopropanal, 3-acetamidiorioanal and 4-aminobutanal in a retinal ganglion cell line," Brain Research, 1145:150-156 (2007).

Wurch et al., "Sequence and functional analysis of cloned guinea pig and rat serotonin 5-HT1D receptors: common pharmacological features within the 5-HT1D receptor subfamily," J. Neurochem., 68:410-418 (1997).

Wynn, "Cellular and molecular mechanisms of fibrosis," J Pathol. 2008;214(2):199-210.

Yadav et al., "Regulation of NF-κB-Induced Inflammatory Signaling by Lipid Peroxidation-Derived Aldehydes," Oxidative Med & Cell Longev, 2013, Art ID 690545, 11 pages (2013).

Yarnell, "Light Flips the Lipid Switch: Palmitoylation-the reversible attachment of palmitate to proteins—gets a new role in vision," C&EN, 82(29):22-23 (2004).

Yokomizo et al., "Hydroxyeicosanoids bind to and activate the low affinity leukotriene B4 receptor, BLT2," J. Biol. Chem., 276:12454-12459 (2001).

Yu et al., "Injectable Chemically Crosslinked Hydrogel for the Controlled Release of Bevacizumab in Vitreous: A 6-Month In Vivo Study," Transl Vis Sci Technol, 4(2,5):1-11 (2015).

Zagol-Ikapitte et al., "Characterization of scavengers of γ-ketoaldehydes that do not inhibit prostaglandin biosynthesis," Chem Res Toxicol, 23(1):240-250 (2010).

Zarkovic "4-hydroxynonenal and neurodegenerative diseases," Molecular Aspects of Medicine, 2003; 24(4-5):293-303.

Zava et al., "Androgen receptor assay with [3H]methyltrienolone (R1881) in the presence of progesterone receptors," Endocrinology, 104:1007-1012 (1979).

Zhang et al., "Potent nonsteroidal progesterone receptor agonists: synthesis and SAR study of 6-aryl benzoxazines," Bioorg Med Chem Lett, 12(5):787-90 (Mar. 2002).

Zhang et al., "Practical ophthalmic pharmacology," People's Military Medical Press, 2015; p. 590.

Zhou et al., "Chemical and biological evidence for base propenals as the major source of the endogenous M1dG adduct in cellular DNA," J Biol Chem., 280(27):25377-82 (2005).

Zhou et al., "Cloning and expression of human and rat D1 dopamine receptors," Nature, 347:76-80 (1990).

Zhou et al., "Mechanisms for the induction of HNE- MDA- and AGE-adducts, RAGE and VEGF in retinal pigment epithelial cells," Exp Eye Res., 80(4):567-80 (2005).

\* cited by examiner

PROCESS FOR PREPARATION OF ALDEHYDE SCAVENGER AND INTERMEDIATES

CROSS-REFERENCE TO RELATED APPLICATIONS

This application is a 35 U.S.C. § 371 National Stage of International Patent Application PCT/US2020/031219, filed May 2, 2020, which claims the benefit under 35 U.S.C. § 119(e) of U.S. Provisional Application No. 62/841,919, filed May 2, 2019, the contents of all of which are incorporated herein by reference in their entireties.

FIELD OF THE INVENTION

The present invention relates to methods for synthesizing compounds, and intermediates thereto, useful for treating diseases, disorders, or conditions in which aldehyde toxicity is implicated in their pathogenesis.

BACKGROUND OF THE INVENTION

Metabolic and inflammatory processes in cells generate toxic aldehydes, such as malondialdehyde (MDA), 4-hydroxyl-2-nonenal (4-HNE), glyoxal, and methylglyoxal. These aldehydes are highly reactive with proteins, carbohydrates, lipids and DNA, leading to chemically modified biological molecules, activation of inflammatory mediators such as NF-kappa B, and damage in diverse organs. For example, retinaldehyde can react with phosphatidylethanolamine (PE) to form a highly toxic compound called A2E, which is a component of lipofuscin that is believed to be involved in the development and progression of Age-Related Macular Degeneration (AMD). Many bodily defense mechanisms function to remove or lower the levels of toxic aldehydes, including metabolism by aldehyde dehydrogenases, buffering by molecules such as glutathione (GSH) and removal from sites of potential toxicity by transporters such as ABCA4. Novel small molecule therapeutics can be used to scavenge "escaped" retinaldehyde in the retina, thus reducing A2E formation and lessening the risk of AMD (see, e.g., WO2006127945 by Jordan et al.).

Aldehydes are implicated in diverse pathological conditions such as dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., systemic lupus erythematosus (SLE) and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents (Negre-Salvayre et al., British J Pharmacol., 2008; 153:6-20; Nakamura et al., Investigative Ophthalmology & Visual Sci., 2007; 48(4):1552-1558; Batista et al., PLoS ONE, 2022 7(3):e33814; Kenney et al., Contact Lens & Anterior Eye, 2003, 26:139-146; Baz et al., Int J Dermatol., 2004; 43(7): 494-7; Nakamura et al., Invest Ophthalmol Vis Sci., 2007; 48(4):1552-8; Augustiin et al., Graefe's Arch Clin Exp Ophthalmol., 1994; 233:694-698; Batista et al., Molecular Vision., 2012; 18:194-202). Decreasing or eliminating aldehydes should thus ameliorate the symptoms and slow the progression of these pathological conditions.

MDA, 4-HNE and other toxic aldehydes are generated by a myriad of metabolic mechanisms involving fatty alcohols, sphingolipids, glycolipids, phytol, fatty acids, arachidonic acid metabolism (Rizzo, Mol Genet Metab., 2007; 90(1):1-9), polyamine metabolism (Wood et al., Brain Res., 2006; 1122:134-190), lipid peroxidation, oxidative metabolism (Buddi et al., J Histochem Cytochem., 2002; 50(3):341-351; Zhou et al., J Biol Chem., 2005; 280(27):25377-25382), and glucose metabolism (Pozzi et al., J Am Soc Nephrol, 2009; 20(10):2119-2125). Aldehydes can cross-link with primary amino groups and other chemical moieties on proteins, phospholipids, carbohydrates, and DNA, leading in many cases to toxic consequences, such as mutagenesis and carcinogenesis (Marnett, Toxicology, 2002; 181-182:219-222). MDA is associated with diseased corneas in conditions such as keratoconus, bullous and other keratopathy, and Fuchs' endothelial dystrophy (Buddi et al., J Histochem Cytochem., 2002; 50(3):341-351). Also, a dysfunctional dermal water barrier in skin disorders such as Sjögren-Larsson Syndrome, are likely connected with the accumulation of fatty aldehydes, including octadecanal and hexadecanal (Rizzo et al., Arch Dermatol Res., 2010; 302:443-451). Further, increased lipid peroxidation and resultant aldehyde generation are associated with the toxic effects of blister agents (Sciuto et al., Inhalation Tech., 2004; 16:565-580) and Pal et al., Free Radic Biol Med., 2009; 47(11):1640-1651).

Accordingly, there remains a need for treating, preventing, and/or reducing a risk of a disease, disorder, or condition in which aldehyde toxicity is implicated in the pathogenesis. There also remains a need for more efficient synthetic routes such that the compounds disclosed herein can be produced on a commercial scale.

SUMMARY OF THE INVENTION

It has now been found that compounds of the present invention, and compositions thereof, are useful for treating, preventing, and/or reducing a risk of a disease, disorder, or condition in which aldehyde toxicity is implicated in the pathogenesis. Such compounds are useful for treating dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus), cardiovascular disorders (e.g., atherosclerosis), conditions associated with the injurious effects of blister agents, diabetic macular edema (DME), atopic keratoconjunctivitis (AKC), vernal keratoconjunctivitis (VKC), age-related macular degeneration (AMD), dry eye disease (DED), allergic conjunctivitis (AC), dry eye disease with allergic conjunctivitis, non-infectious anterior uveitis, posterior uveitis, pan-uveitis, post-surgical ocular pain and inflammation, corneal fibrosis after radial keratotomy, corneal fibrosis after trauma or exposure to vesicants, corneal fibrosis after infection, non-clinically significant macular edema (Non-CSME), clinically significant macular edema (CSME), uveitis, anterior uveitis, non-infectious uveitis, Behçet's syndrome, ankylosing spondylitis, Lyme disease, sarcoidosis, and psoriasis.

In general, compounds of the present disclosure, and compositions thereof, are useful for treating or lessening the severity of a variety of diseases, disorders or conditions as described herein. In some embodiments, such compounds are represented by the chemical formula below, denoted as Formula II:

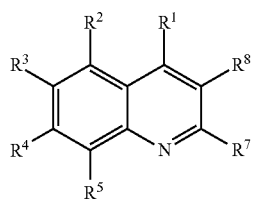

or a pharmaceutically acceptable salt thereof, wherein $R^1$, $R^2$, $R^3$, $R^4$, $R^5$, $R^7$ and $R^8$ are as described below, and wherein compounds of Formula II may be synthesized according to methods described below.

In some embodiments, such compounds are represented by the chemical formula below, denoted as Formula IV:

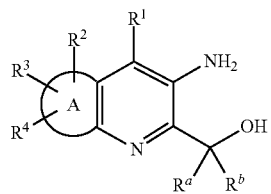

or a pharmaceutically acceptable salt thereof, wherein Ring A, $R^1$, $R^2$, $R^3$, $R^4$, $R^a$ and $R^b$ are as described below, and wherein compounds of Formula IV may be synthesized according to methods described below.

Compounds of the present disclosure, and pharmaceutically acceptable compositions thereof, are useful for treating a variety of diseases, disorders, or conditions associated with toxic aldehydes. Such diseases, disorders, or conditions include those described herein. Compounds provided by this present disclosure are also useful for the study of certain aldehydes in biology and pathological phenomena.

The present invention provides efficient synthetic routes such that the compounds disclosed herein can be produced on a commercial scale. The present invention also provides synthetic intermediates useful for preparing such compounds.

DETAILED DESCRIPTION OF THE INVENTION

Definitions

Compounds of the present disclosure include those described generally above, and are further illustrated by the classes, subclasses, and species disclosed herein. As used herein, the following definitions shall apply unless otherwise indicated. For purposes of the present disclosure, the chemical elements are identified in accordance with the Periodic Table of the Elements, CAS version, *Handbook of Chemistry and Physics*, 75$^{th}$ Ed. Additionally, general principles of organic chemistry are described in *Organic Chemistry*, Thomas Sorrell, University Science Books, Sausalito: 1999, and *March's Advanced Organic Chemistry*, 5$^{th}$ Ed., Ed.: Smith, M. B. and March, J., John Wiley & Sons, New York: 2001, the entire contents of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a Cia straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$(or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In some embodiments, the term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. In certain embodiments of the compounds, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned for the compounds herein are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen, —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —OC(O)$(CH_2)_{0-4}SR$—, SC(S)SR$^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —SC(S)SR$^\circ$, —$(CH_2)_{0-4}OC(O)NR^\circ_2$; —C(O)

N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, and a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, and an unsubstituted 5- to 6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*2)$_{2-3}$O—, wherein each independent occurrence of R* is selected from hydrogen, C$_{1-6}$ aliphatic which may be substituted as defined below, and an unsubstituted 5 to 6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, and sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3- to 12-membered saturated, partially unsaturated, or aryl mono- or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, and sulfur.

General Description of Certain Aspects of the Invention

1. General Synthetic Processes and Synthesis of Compound A

In some embodiments, compounds that may be synthesized by methods described herein include those of Formula II, or pharmaceutically acceptable salts thereof. Such compounds are represented by the chemical formula below, denoted as Formula II:

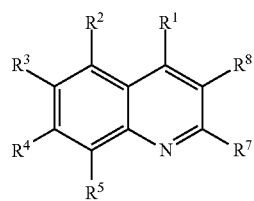

II or a pharmaceutically acceptable salt thereof, wherein:
R$^1$ is H, D, halogen, —NH$_2$, —CN, —OR, —SR, or optionally substituted C$_{1-6}$ aliphatic;
R$^7$ and R$^8$ is —NH$_2$ or

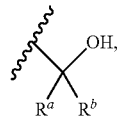

wherein one of R$^7$ and R$^8$ is —NH$_2$ and other one of R$^7$ and R$^8$ is

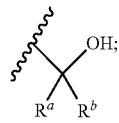

R$^2$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, or —S(O)$_2$R;

R$^3$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, or —S(O)$_2$R;

R$^4$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, or —S(O)$_2$R;

R$^5$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, or —S(O)$_2$R;

R$^a$ is C$_{1-4}$ aliphatic optionally substituted with 1, 2, or 3 deuterium or halogen atoms;

R$^b$ is C$_{1-4}$ aliphatic optionally substituted with 1, 2, or 3 deuterium or halogen atoms; or R$^a$ and R$^b$, taken together with the carbon atom to which they are attached, form a 3- to 8-membered cycloalkyl or heterocyclyl ring containing 1-2 heteroatoms selected from nitrogen, oxygen, and sulfur; and each R is independently selected from hydrogen, deuterium, or an optionally substituted group selected from C$_{1-6}$ aliphatic; a 3- to 8-membered saturated or partially unsaturated monocyclic carbocyclic ring; phenyl; an 8- to 10-membered bicyclic aryl ring; a 3- to 8-membered saturated or partially unsaturated monocyclic heterocyclic ring having 1-4 heteroatoms independently selected from nitrogen, oxygen, or sulfur; a 5- to 6-membered monocyclic heteroaryl ring having 1-4 heteroatoms independently selected from nitrogen, oxygen, or sulfur; a 6- to 10-membered bicyclic saturated or partially unsaturated heterocyclic ring having 1-5 heteroatoms independently selected from nitrogen, oxygen, or sulfur; or a 7- to 10-membered bicyclic heteroaryl ring having 1-5 heteroatoms independently selected from nitrogen, oxygen, or sulfur.

In some embodiments, R$^7$ is

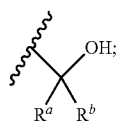

and R$^8$ is —NH$_2$.

In some embodiments, a compound according to Formula II, or pharmaceutically acceptable salts thereof, may be prepared according to general Scheme 1 below.

Scheme 1: Synthesis of Compound of Formula II

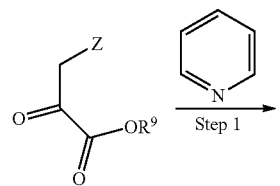

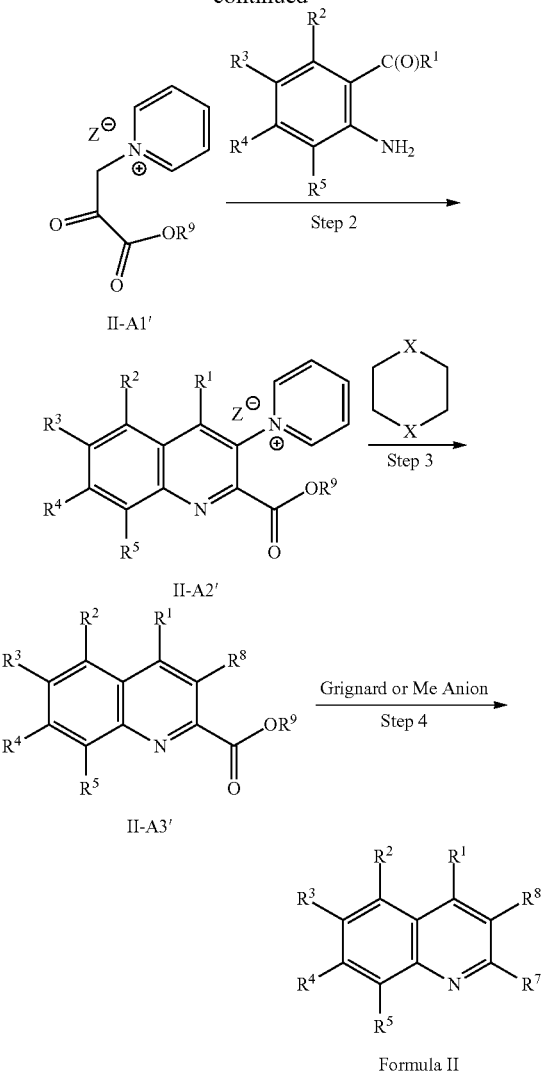

wherein, Z is a halogen, each X is independently —NH, O or S; and each of R$^1$, R$^2$, R$^3$, R$^4$, R$^5$, R$^7$ and R$^8$ are as defined above for Formula II, and R$^9$ is an aliphatic group, preferably a C$_{1-6}$aliphatic, more preferably a C$_{1-6}$alkyl. In some embodiments, R$^9$ is methyl, ethyl, or propyl. In some embodiments, Z is fluoro (F), chloro (Cl), or bromo (Br), preferably Br.

In some embodiments, the Grignard reagent is an alkyl, vinyl or aryl Grignard reagent. In some embodiments, the Grignard reagent is an alkyl Grignard reagent. In some embodiments, the Grignard reagent is a methyl Grignard reagent. In some embodiments, the Grignard reagent is an ethyl Grignard reagent. In some embodiments, the Grignard reagent is a propyl Grignard reagent. In some embodiments, the Grignard reagent is an aryl Grignard reagent. In some embodiments, the Grignard reagent is MeMgY, where Y is Cl, Br or Cl. In some embodiments, the Me-Anion is, for example, MeM, where M is Li, Sr, Ce, or Co; Me$_2$CuLi or mixed cuprates with I, Br, or Cl; or AlMe$_3$ (trimethylaluminum). In some embodiments, an exemplary Grignard reagent is MeMgCl.

In some embodiments, a compound according to Formula II, or pharmaceutically acceptable salts thereof, may be prepared according to Scheme 1a using alkyl bromopyruvate (EBP) below.

Scheme 1a: Synthesis of Compound of Formula II

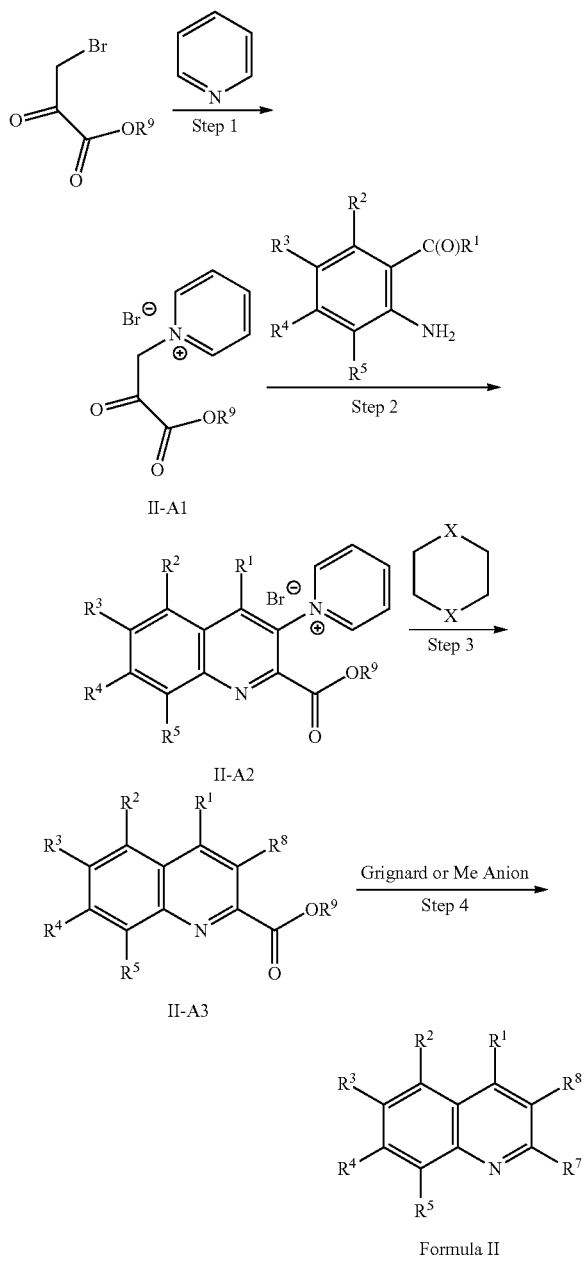

wherein each X is independently —NH, O or S; and each of R, $R^2$, $R^3$, $R^4$, $R^5$, $R^7$ and $R^8$ are as defined above for Formula II, and $R^9$ is an aliphatic group, preferably a $C_{1-6}$ aliphatic, more preferably a $C_{1-6}$ alkyl. In some embodiments, $R^9$ is methyl, ethyl, or propyl.

As defined generally above, $R^1$ is H, D, halogen, —CN, —OR, —SR, or optionally substituted $C_{1-6}$ aliphatic.

In some embodiments, $R^1$ is H. In some embodiments, $R^1$ is D. In some embodiments, $R^1$ is halogen. In some embodiments, $R^1$ is —CN. In some embodiments, $R^1$ is —OR. In some embodiments, $R^1$ is —SR. In some embodiments, $R^1$ is optionally substituted $C_{1-6}$ aliphatic.

As defined generally above, $R^2$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, or —S(O)$_2$R;

In some embodiments, $R^2$ is absent. In some embodiments, $R^2$ is —R. In some embodiments, $R^2$ is halogen. In some embodiments, $R^2$ is —CN. In some embodiments, $R^2$ is —OR. In some embodiments, $R^2$ is —SR. In some embodiments, $R^2$ is —N(R)$_2$. In some embodiments, $R^2$ is —N(R)C(O)R. In some embodiments, $R^2$ is —C(O)N(R)$_2$. In some embodiments, $R^2$ is —N(R)C(O)N(R)$_2$. In some embodiments, $R^2$ is —N(R)C(O)OR. In some embodiments, $R^2$ is —OC(O)N(R)$_2$. In some embodiments, $R^2$ is —N(R)S(O)$_2$R. In some embodiments, $R^2$ is —SO$_2$N(R)$_2$. In some embodiments, $R^2$ is —C(O)R. In some embodiments, $R^2$ is —C(O)OR. In some embodiments, $R^2$ is —OC(O)R. In some embodiments, $R^2$ is —S(O)R. In some embodiments, $R^2$ is —S(O)$_2$R.

In some embodiments, $R^2$ is hydrogen. In some embodiments, $R^2$ is deuterium. In some embodiments, $R^2$ is an optionally substituted $C_{1-6}$ aliphatic. In some embodiments, $R^2$ is an optionally substituted 3- to 8-membered saturated or partially unsaturated monocyclic carbocyclic ring. In some embodiments, $R^2$ is an optionally substituted phenyl. In some embodiments, $R^2$ is an optionally substituted 8- to 10-membered bicyclic aryl ring. In some embodiments, $R^2$ is an optionally substituted 3- to 8-membered saturated or partially unsaturated monocyclic heterocyclic ring having 1-4 heteroatoms independently selected from nitrogen, oxygen, or sulfur. In some embodiments, $R^2$ is an optionally substituted 5- to 6-membered monocyclic heteroaryl ring having 1-4 heteroatoms independently selected from nitrogen, oxygen, or sulfur. In some embodiments, $R^2$ is an optionally substituted 6- to 10-membered bicyclic saturated or partially unsaturated heterocyclic ring having 1-5 heteroatoms independently selected from nitrogen, oxygen, or sulfur. In some embodiments, $R^2$ is an optionally substituted 7- to 10-membered bicyclic heteroaryl ring having 1-5 heteroatoms independently selected from nitrogen, oxygen, or sulfur.

In some embodiments, $R^2$ is Cl or Br. In some embodiments, $R^2$ is Cl.

As defined generally above, $R^3$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, or —S(O)$_2$R.

In some embodiments, $R^3$ is absent. In some embodiments, $R^3$ is —R. In some embodiments, $R^3$ is halogen. In some embodiments, $R^3$ is —CN. In some embodiments, $R^3$ is —OR. In some embodiments, $R^3$ is —SR. In some embodiments, $R^3$ is —N(R)$_2$. In some embodiments, $R^3$ is —N(R)C(O)R. In some embodiments, $R^3$ is —C(O)N(R)$_2$. In some embodiments, $R^3$ is —N(R)C(O)N(R)$_2$. In some embodiments, $R^3$ is —N(R)C(O)OR. In some embodiments, $R^3$ is —OC(O)N(R)$_2$. In some embodiments, $R^3$ is —N(R)S(O)$_2$R. In some embodiments, $R^3$ is —SO$_2$N(R)$_2$. In some embodiments, $R^3$ is —C(O)R. In some embodiments, $R^3$ is —C(O)OR. In some embodiments, $R^3$ is —OC(O)R. In some embodiments, $R^3$ is —S(O)R. In some embodiments, $R^3$ is —S(O)$_2$R.

In some embodiments, $R^3$ is hydrogen. In some embodiments, $R^3$ is deuterium. In some embodiments, $R^3$ is an optionally substituted $C_{1-6}$ aliphatic. In some embodiments, $R^3$ is an optionally substituted 3- to 8-membered saturated or partially unsaturated monocyclic carbocyclic ring. In some embodiments, $R^3$ is an optionally substituted phenyl. In some embodiments, $R^3$ is an optionally substituted 8- to 10-membered bicyclic aryl ring. In some embodiments, $R^3$ is an optionally substituted 3- to 8-membered saturated or partially unsaturated monocyclic heterocyclic ring having 1-4 heteroatoms independently selected from nitrogen, oxygen, or sulfur. In some embodiments, $R^3$ is an optionally substituted 5- to 6-membered monocyclic heteroaryl ring having 1-4 heteroatoms independently selected from nitrogen, oxygen, or sulfur. In some embodiments, $R^3$ is an optionally substituted 6- to 10-membered bicyclic saturated or partially unsaturated heterocyclic ring having 1-5 heteroatoms independently selected from nitrogen, oxygen, or sulfur. In some embodiments, $R^3$ is an optionally substituted 7- to 10-membered bicyclic heteroaryl ring having 1-5 heteroatoms independently selected from nitrogen, oxygen, or sulfur.

In some embodiments, $R^3$ is Cl or Br. In some embodiments, $R^3$ is Cl.

As defined generally above, $R^4$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, or —S(O)$_2$R.

In some embodiments, $R^4$ is absent. In some embodiments, $R^4$ is —R. In some embodiments, $R^4$ is halogen. In some embodiments, $R^4$ is —CN. In some embodiments, $R^4$ is —OR. In some embodiments, $R^4$ is —SR. In some embodiments, $R^4$ is —N(R)$_2$. In some embodiments, $R^4$ is —N(R)C(O)R. In some embodiments, $R^4$ is —C(O)N(R)$_2$. In some embodiments, $R^4$ is —N(R)C(O)N(R)$_2$. In some embodiments, $R^4$ is —N(R)C(O)OR. In some embodiments, $R^4$ is —OC(O)N(R)$_2$. In some embodiments, $R^4$ is —N(R)S(O)$_2$R. In some embodiments, $R^4$ is —SO$_2$N(R)$_2$. In some embodiments, $R^4$ is —C(O)R. In some embodiments, $R^4$ is —C(O)OR. In some embodiments, $R^4$ is —OC(O)R. In some embodiments, $R^4$ is —S(O)R. In some embodiments, $R^4$ is —S(O)$_2$R.

In some embodiments, $R^4$ is hydrogen. In some embodiments, $R^4$ is deuterium. In some embodiments, $R^4$ is an optionally substituted $C_{1-6}$ aliphatic. In some embodiments, $R^4$ is an optionally substituted 3- to 8-membered saturated or partially unsaturated monocyclic carbocyclic ring. In some embodiments, $R^4$ is an optionally substituted phenyl. In some embodiments, $R^4$ is an optionally substituted 8- to 10-membered bicyclic aryl ring. In some embodiments, $R^4$ is an optionally substituted 3- to 8-membered saturated or partially unsaturated monocyclic heterocyclic ring having 1-4 heteroatoms independently selected from nitrogen, oxygen, or sulfur. In some embodiments, $R^4$ is an optionally substituted 5- to 6-membered monocyclic heteroaryl ring having 1-4 heteroatoms independently selected from nitrogen, oxygen, or sulfur. In some embodiments, $R^4$ is an optionally substituted 6- to 10-membered bicyclic saturated or partially unsaturated heterocyclic ring having 1-5 heteroatoms independently selected from nitrogen, oxygen, or sulfur. In some embodiments, $R^4$ is an optionally substituted 7- to 10-membered bicyclic heteroaryl ring having 1-5 heteroatoms independently selected from nitrogen, oxygen, or sulfur.

In some embodiments, $R^4$ is Cl or Br. In some embodiments, $R^4$ is Cl.

As defined generally above, $R^5$ is absent or is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, or —S(O)$_2$R;

In some embodiments, $R^5$ is absent. In some embodiments, $R^5$ is —R. In some embodiments, $R^5$ is halogen. In some embodiments, $R^5$ is —CN. In some embodiments, $R^5$ is —OR. In some embodiments, $R^5$ is —SR. In some embodiments, $R^5$ is —N(R)$_2$. In some embodiments, $R^5$ is —N(R)C(O)R. In some embodiments, $R^5$ is —C(O)N(R)$_2$. In some embodiments, $R^5$ is —N(R)C(O)N(R)$_2$. In some embodiments, $R^5$ is —N(R)C(O)OR. In some embodiments, $R^5$ is —OC(O)N(R)$_2$. In some embodiments, $R^5$ is —N(R)S(O)$_2$R. In some embodiments, $R^5$ is —SO$_2$N(R)$_2$. In some embodiments, $R^5$ is —C(O)R. In some embodiments, $R^5$ is —C(O)OR. In some embodiments, $R^5$ is —OC(O)R. In some embodiments, $R^5$ is —S(O)R. In some embodiments, $R^5$ is —S(O)$_2$R.

In some embodiments, $R^5$ is hydrogen. In some embodiments, $R^5$ is deuterium. In some embodiments, $R^5$ is an optionally substituted $C_{1-6}$ aliphatic. In some embodiments, $R^1$ is an optionally substituted 3- to 8-membered saturated or partially unsaturated monocyclic carbocyclic ring. In some embodiments, $R^5$ is an optionally substituted phenyl. In some embodiments, $R^5$ is an optionally substituted 8- to 10-membered bicyclic aryl ring. In some embodiments, $R^5$ is an optionally substituted 3- to 8-membered saturated or partially unsaturated monocyclic heterocyclic ring having 1-4 heteroatoms independently selected from nitrogen, oxygen, or sulfur. In some embodiments, $R^5$ is an optionally substituted 5- to 6-membered monocyclic heteroaryl ring having 1-4 heteroatoms independently selected from nitrogen, oxygen, or sulfur. In some embodiments, $R^5$ is an optionally substituted 6- to 10-membered bicyclic saturated or partially unsaturated heterocyclic ring having 1-5 heteroatoms independently selected from nitrogen, oxygen, or sulfur. In some embodiments, $R^5$ is an optionally substituted 7- to 10-membered bicyclic heteroaryl ring having 1-5 heteroatoms independently selected from nitrogen, oxygen, or sulfur.

In some embodiments, $R^5$ is Cl or Br. In some embodiments, $R^5$ is Cl.

As defined above, $R^7$ and $R^8$ is NH$_2$ or

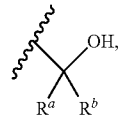

wherein one of $R^7$ and $R^8$ is —NH$_2$ and other one of $R^7$ and $R^8$ is

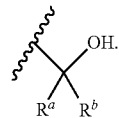

In some embodiments, $R^7$ is

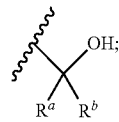

and $R^8$ is —NH$_2$.

As defined generally above, $R^a$ is $C_{1-4}$ aliphatic optionally substituted with 1, 2, or 3 deuterium or halogen atoms.

In some embodiments, $R^a$ is $C_{1-4}$ aliphatic. In some embodiments, $R^a$ is $C_{1-4}$ aliphatic optionally substituted with 1, 2, or 3 deuterium atoms. In some embodiments, $R^a$ is $C_{1-4}$ aliphatic optionally substituted with 1, 2, or 3 halogen atoms.

In some embodiments, $R^a$ is $C_{1-4}$ alkyl. In some embodiments, $R^a$ is $C_{1-4}$ alkyl optionally substituted with 1, 2, or 3 deuterium or halogen atoms. In some embodiments, $R^a$ is $C_{1-4}$ alkyl optionally substituted with 1, 2, or 3 halogen atoms. In some embodiments, $R^a$ is methyl or ethyl optionally substituted with 1, 2, or 3 halogen atoms. In some embodiments, $R^a$ is methyl.

As defined generally above, $R^b$ is $C_{1-4}$ aliphatic optionally substituted with 1, 2, or 3 deuterium or halogen atoms.

In some embodiments, $R^b$ is $C_{1-4}$ aliphatic. In some embodiments, $R^b$ is $C_{1-4}$ aliphatic optionally substituted with 1, 2, or 3 deuterium atoms. In some embodiments, $R^b$ is $C_{1-4}$ aliphatic optionally substituted with 1, 2, or 3 halogen atoms.

In some embodiments, $R^b$ is $C_{1-4}$ alkyl. In some embodiments, $R^b$ is $C_{1-4}$ alkyl optionally substituted with 1, 2, or 3 deuterium or halogen atoms. In some embodiments, $R^b$ is $C_{1-4}$ alkyl optionally substituted with 1, 2, or 3 halogen atoms. In some embodiments, $R^b$ is methyl or ethyl optionally substituted with 1, 2, or 3 halogen atoms. In some embodiments, $R^b$ is methyl.

As defined generally above, $R^a$ and $R^b$ may be taken together with the carbon atom to which they are attached, form a 3- to 8-membered cycloalkyl or heterocyclyl ring containing 1-2 heteroatoms selected from nitrogen, oxygen, and sulfur.

In some embodiments, $R^a$ and $R^b$ may be taken together with the carbon atom to which they are attached, form a 3- to 8-membered cycloalkyl. In some embodiments, $R^a$ and $R^b$ may be together with the carbon atom to which they are attached, form a 3- to 8-membered heterocyclyl ring containing 1-2 heteroatoms selected from nitrogen, oxygen, and sulfur.

In some embodiments, $R^a$ and $R^b$ may be together with the carbon atom to which they are attached, form a cyclopropyl, cyclobutyl, or cyclopentyl ring. In some embodiments, $R^a$ and $R^b$ may be together with the carbon atom to which they are attached, form an oxirane, oxetane, tetrahydrofuran, or aziridine.

In some embodiments, compounds that may be synthesized by methods described herein include those of Formula IV, or pharmaceutically acceptable salts thereof. Such compounds are represented by the chemical formula below, denoted as Formula IV:

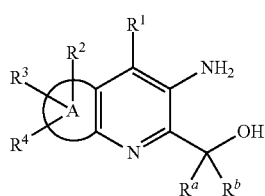

IV or a pharmaceutically acceptable salt thereof, wherein:
Ring A is phenyl, a 5-membered partially unsaturated heterocyclic or heteroaromatic ring containing 1-3 nitrogen atoms, 1 or 2 oxygen atoms, 1 sulfur atom, or 1 nitrogen and 1 sulfur atom; or a 6-membered partially unsaturated heterocyclic or heteroaromatic ring containing 1-3 heteroatoms independently selected from nitrogen, oxygen, or sulfur; or a 7-membered partially unsaturated heterocyclic or heteroaromatic ring containing 1-3 heteroatoms independently selected from nitrogen, oxygen, or sulfur;

and each of R, $R^1$, $R^2$, $R^3$, $R^4$, $R^a$ and $R^b$ are as defined above for Formula II, and apply to the compounds of Formula IV, either alone or in combination.

In some embodiments, a compound according to Formula IV, or pharmaceutically acceptable salts thereof, may be prepared according to the Scheme 2 below.

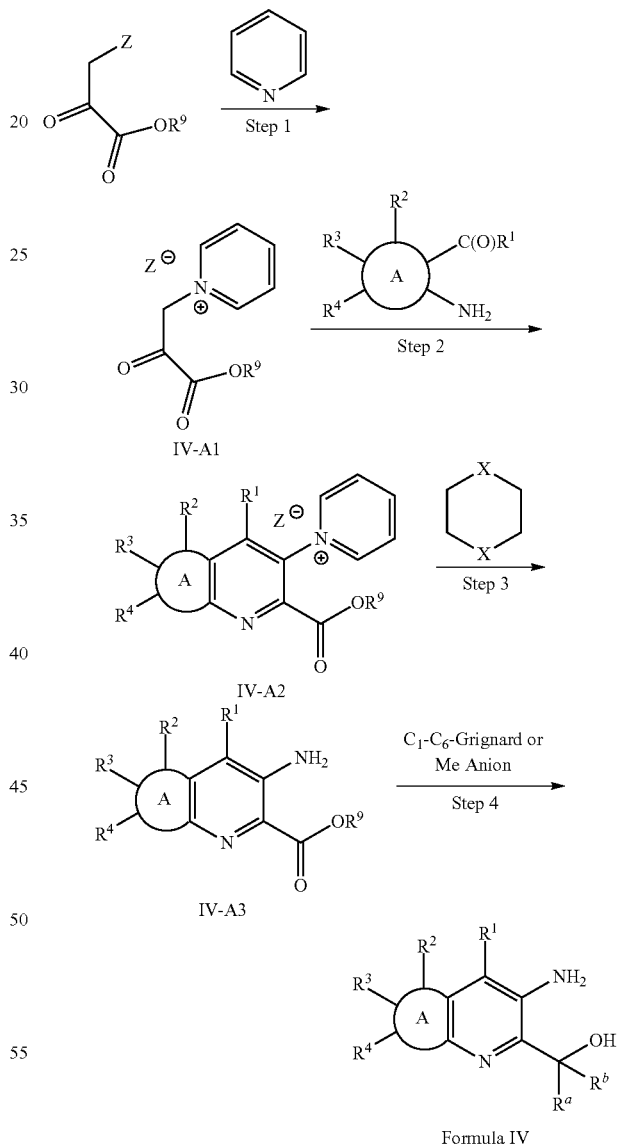

As defined generally above, Ring A is phenyl, a 5-membered partially unsaturated heterocyclic or heteroaromatic ring containing 1-3 nitrogen atoms, 1 or 2 oxygen atoms, 1 sulfur atom, or 1 nitrogen and 1 sulfur atom; or a 6-membered partially unsaturated heterocyclic or heteroaromatic ring containing 1-3 heteroatoms independently selected from nitrogen, oxygen, or sulfur; or a 7-membered partially unsaturated heterocyclic or heteroaromatic ring containing 1-3 heteroatoms independently selected from nitrogen, oxygen, or sulfur.

In some embodiments, Ring A is phenyl. In some embodiments, Ring A is a 5-membered partially unsaturated heterocyclic or heteroaromatic ring containing 1-3 nitrogen atoms, 1 or 2 oxygen atoms, 1 sulfur atom, or 1 nitrogen and 1 sulfur atom. In some embodiments, Ring A is a 6-membered partially unsaturated heterocyclic or heteroaromatic ring containing 1-3 heteroatoms independently selected from nitrogen, oxygen, or sulfur. In some embodiments, Ring A is a 7-membered partially unsaturated heterocyclic or heteroaromatic ring containing 1-3 heteroatoms independently selected from nitrogen, oxygen, or sulfur.

In some embodiments, Ring A is imidazole or triazole. In some embodiments, Ring A is thiazole. In some embodiments, Ring A is thiophene or furan. In some embodiments, Ring A is pyridine, pyrimidine, pyrazine, pyridazine, or 1,2,4-triazine. In some embodiments, Ring A is pyridine.

The definitions and embodiments set forth above with respect to the compounds of Formula II regarding each of R, $R^1$, $R^2$, $R^3$, $R^4$, $R^a$ and $R^b$ in Scheme 1 are as defined above for Formula II, and apply to the compounds of Formula IV in Scheme 2, either alone or in combination; $R^9$ is an aliphatic group, in particular a $C_{1-6}$aliphatic, preferably a $C_{1-6}$alkyl (e.g., methyl, ethyl, or propyl); Z is a halogen, preferably fluoro (F), chloro (Cl), or bromo (Br), more preferably Br; and each X is independently —NH, O or S.

In some embodiments, the Grignard reagent is an alkyl, vinyl or aryl Grignard reagent. In some embodiments, the Grignard reagent is an alkyl Grignard reagent. In some embodiments, the Grignard reagent is a methyl Grignard reagent. In some embodiments, the Grignard reagent is an ethyl Grignard reagent. In some embodiments, the Grignard reagent is a propyl Grignard reagent. In some embodiments, the Grignard reagent is an aryl Grignard reagent. In some embodiments, the Grignard reagent is MeMgY, where Y is Cl, Br or Cl. In some embodiments, the Me-Anion is, for example, MeM, where M is Li, Sr, Ce, or Co; Me$_2$CuLi or mixed cuprates with I, Br, or Cl; or AlMe$_3$ (trimethylaluminum). In some embodiments, an exemplary Grignard reagent is MeMgCl.

In some embodiments, the pyridine in step 1) is replaced with a suitable heterocycle, particularly an N-containing heterocycle, such as described for synthesis of a compound of Formula II.

In some embodiments, the suitable heterocycle in step 3) is morpholine, or other such heterocycles, such as described for synthesis of a compound of Formula II.

In some embodiments, a compound according to Formula IV, or pharmaceutically acceptable salts thereof, may be prepared according to the Scheme 2a below using a bromopyruvate starting material and Grignard reagent.

Scheme 2a: Synthesis of Compound of Formula IV.

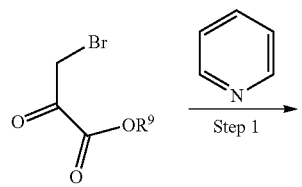

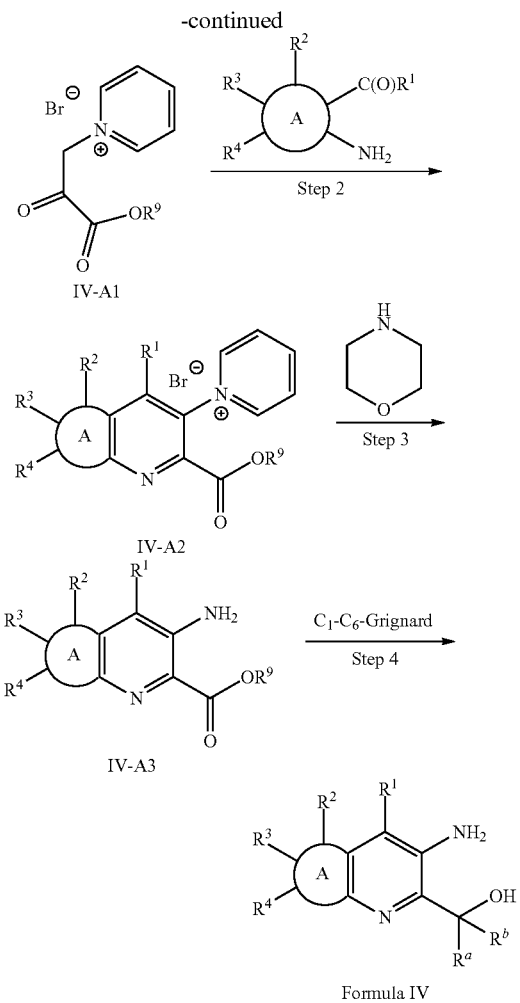

Formula IV

As defined above for Scheme 2, in Scheme 2a Ring A is phenyl, a 5-membered partially unsaturated heterocyclic or heteroaromatic ring containing 1-3 nitrogen atoms, 1 or 2 oxygen atoms, 1 sulfur atom, or 1 nitrogen and 1 sulfur atom; or a 6-membered partially unsaturated heterocyclic or heteroaromatic ring containing 1-3 heteroatoms independently selected from nitrogen, oxygen, or sulfur; or a 7-membered partially unsaturated heterocyclic or heteroaromatic ring containing 1-3 heteroatoms independently selected from nitrogen, oxygen, or sulfur.

In some embodiments, Ring A is phenyl. In some embodiments, Ring A is a 5-membered partially unsaturated heterocyclic or heteroaromatic ring containing 1-3 nitrogen atoms, 1 or 2 oxygen atoms, 1 sulfur atom, or 1 nitrogen and 1 sulfur atom. In some embodiments, Ring A is a 6-membered partially unsaturated heterocyclic or heteroaromatic ring containing 1-3 heteroatoms independently selected from nitrogen, oxygen, or sulfur. In some embodiments, Ring A is a 7-membered partially unsaturated heterocyclic or heteroaromatic ring containing 1-3 heteroatoms independently selected from nitrogen, oxygen, or sulfur.

In some embodiments, Ring A is imidazole or triazole. In some embodiments, Ring A is thiazole. In some embodiments, Ring A is thiophene or furan. In some embodiments, Ring A is pyridine, pyrimidine, pyrazine, pyridazine, or 1,2,4-triazine. In some embodiments, Ring A is pyridine.

The definitions and embodiments set forth above with respect the compounds of Formula II regarding each of R, $R^1$, $R^2$, $R^3$, $R^4$, $R^a$ and $R^b$ are as defined above for Formula II, and apply to the compounds of Formula IV in Scheme 2a, either alone or in combination; and $R^9$ is an aliphatic group, preferably a $C_{1-6}$aliphatic, more preferably a $C_{1-6}$alkyl. In some embodiments, $R^9$ is methyl, ethyl, or propyl.

In any of Schemes 1, 1a, 2, and 2a shown above, there are generally 4 steps in the synthetic methods described therein.

Step 1

Step 1 of the synthetic methods described herein is directed to coupling of a pyruvate starting material (e.g., an alkylhalopyruvate) with a suitable heterocycle in an alcoholic solvent, optionally at elevated temperature, to produce Compound II-A1'/II-A1 or IV-A1'/IV-A1.

In some embodiments, the pyruvate is halogenated. In some embodiments, the pyruvate is fluorinated. In some embodiments, the pyruvate is chlorinated. In some embodiments, the pyruvate is brominated.

In some embodiments, the pyruvate includes an aliphatic group. In some embodiments, the pyruvate includes a methyl group. In some embodiments, the pyruvate includes an ethyl group. In some embodiments, the pyruvate includes a propyl group.

In some embodiments, the pyruvate is methyl bromopyruvate (MBP). In some embodiments, the pyruvate is ethyl bromopyruvate (EBP). In some embodiments, the pyruvate is propyl bromopyruvate (PBP).

In some embodiments, the suitable heterocycle is a 5-membered ring containing at least one heteroatom selected from N, O and S. In some embodiments, the heterocycle is a 7-membered ring containing at least one heteroatom selected from N, O and S. In some embodiments, the heterocycle is a 6-membered ring containing at least one heteroatom selected from N, O and S. In some embodiments, the heterocycle is a 5-membered ring or 6-membered ring containing at least one N atom. In some embodiments, the N-containing heterocycle is pyridine.

In some embodiments, the alcoholic solvent is methanol. In some embodiments, the alcoholic solvent is ethanol. In some embodiments, the alcoholic solvent is propanol. In some embodiments, the alcoholic solvent is phenol.

In some embodiments, step 1 takes place at ambient temperature. In some embodiments, step 1 takes place at an elevated temperature. In some embodiments, the elevated temperature is between about 40° C. to about 50° C. In some embodiments, the elevated temperature is between about 50° C. to about 60° C. In some embodiments, the elevated temperature is between about 60° C. to about 70° C. In some embodiments, the elevated temperature is between about 70° C. to about 80° C. In some embodiments, the elevated temperature is between about 90° C. to about 100° C. In some embodiments, the elevated temperature is about 65° C.

Step 2

Step 2 of the synthetic methods described herein is directed to coupling of Compound II-A1'/II-A1 or II-A4'/II-A4 with Ring A or an optionally substituted phenyl ring below,

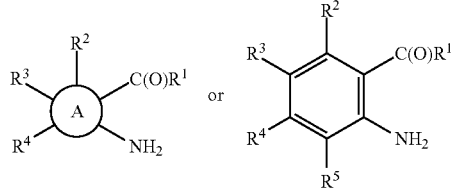

in an alcoholic solvent, optionally at elevated temperature, and in the presence of a heterocycle, to form Compound II-A2'/II-A2 or IV-A2'/IV-A2.

In some embodiments, the heterocycle is a 5-membered ring containing at least one heteroatom selected from N, O and S. In some embodiments, the heterocycle is a 7-membered ring containing at least one heteroatom selected from N, O and S. In some embodiments, the heterocycle is a 6-membered ring containing at least one heteroatom selected from N, O and S. In some embodiments, the heterocycle is a 5-membered ring or 6-membered ring containing at least one N atom. In some embodiments, the heterocycle is pyridine.

In some embodiments, the alcoholic solvent is methanol. In some embodiments, the alcoholic solvent is ethanol. In some embodiments, the alcoholic solvent is propanol. In some embodiments, the alcoholic solvent is phenol.

In some embodiments, step 2 takes place at ambient temperature. In some embodiments, step 2 takes place at an elevated temperature. In some embodiments, the elevated temperature is between about 40° C. to about 50° C. In some embodiments, the elevated temperature is between about 50° C. to about 60° C. In some embodiments, the elevated temperature is between about 60° C. to about 70° C. In some embodiments, the elevated temperature is between about 70° C. to about 80° C. In some embodiments, the elevated temperature is between about 90° C. to about 100° C. In some embodiments, the elevated temperature is about 80° C.

Step 3

Step 3 of the synthetic methods described herein is directed to coupling of Compound II-A2'/II-A2 or IV-A2'/IV-A2 with a suitable heterocycle in an alcoholic solvent, optionally at elevated temperature, to form Compound II-A3'/II-A3 or IV-A3'/IV-A3.

In some embodiments, the heterocycle is a 5-membered ring containing at least one heteroatom selected from N, O and S. In some embodiments, the heterocycle is a 7-membered ring containing at least one heteroatom selected from N, O and S. In some embodiments, the heterocycle is a 6-membered ring containing at least one heteroatom selected from N, O and S. In some embodiments, the heterocycle is a 5-membered ring or 6-membered ring containing at least one N atom and at least one O atom. In some embodiments, the heterocycle is morpholine.

In some embodiments, the alcoholic solvent is methanol. In some embodiments, the alcoholic solvent is ethanol. In some embodiments, the alcoholic solvent is propanol. In some embodiments, the alcoholic solvent is phenol.

In some embodiments, step 3 takes place at ambient temperature. In some embodiments, step 1 takes place at an elevated temperature. In some embodiments, the elevated temperature is between about 40° C. to about 50° C. In some embodiments, the elevated temperature is between about 50° C. to about 60° C. In some embodiments, the elevated temperature is between about 60° C. to about 70° C. In some embodiments, the elevated temperature is between about 70° C. to about 80° C. In some embodiments, the elevated temperature is between about 90° C. to about 100° C. In some embodiments, the elevated temperature is about 80° C.

Step 4

Step 4 of the synthetic methods described herein is directed to coupling of Compound II-A3'/II-A3 or IV-A3'/IV-A3 with a Grignard reagent or methyl anion (denoted Me-Anion) in a heterocyclic solvent, to produce the compound of Formula II or IV.

In some embodiments, the Grignard reagent is an alkyl, vinyl or aryl Grignard reagent. In some embodiments, the Grignard reagent is an alkyl Grignard reagent. In some embodiments, the Grignard reagent is a methyl Grignard reagent. In some embodiments, the Grignard reagent is an ethyl Grignard reagent. In some embodiments, the Grignard reagent is a propyl Grignard reagent. In some embodiments, the Grignard reagent is an aryl Grignard reagent. In some embodiments, the Grignard reagent is MeMgY, where Y is Cl, Br or Cl. In some embodiments, the Me-Anion is, for example, MeM, where M is Li, Sr, Ce, or Co; Me$_2$CuLi or mixed cuprates with I, Br, or Cl; or AlMe$_3$ (trimethylaluminum). In some embodiments, an exemplary Grignard reagent is MeMgCl.

In some embodiments, the heterocyclic solvent is a 5-membered ring containing at least one heteroatom selected from N, O and S. In some embodiments, the heterocyclic solvent is a 6-membered ring containing at least one heteroatom selected from N, O and S. In some embodiments, the heterocyclic solvent is a 5-membered ring containing at least one 0 atoms. In some embodiments, the heterocyclic solvent is tetrahydrofuran (THF).

Thus, in some embodiments, the invention provides a process for the preparation of a compound of Formula II comprising:
  step 1) treating a pyruvate starting material with a heterocycle to produce Compound II-A1'/II-A;
  step 2) treating Compound II-A1'/II-A1 with an optionally substituted phenyl ring above to form Compound II-A2'/II-A2;
  step 3) treating Compound II-A2'/II-A2 with a suitable heterocycle to form Compound II-A3'/II-A3; and
  step 4) treating Compound II-A3'/II-A3 with a Grignard reagent or methyl anion to produce the compound of Formula II.

In some embodiments, the invention provides a process for the preparation of a compound of Formula II comprising:
  step 1) treating pyruvate starting material with a heterocycle in an alcoholic solvent, optionally at elevated temperature, to produce Compound II-A1'/II-A1;
  step 2) treating Compound II-A1'/II-A1 with an optionally substituted phenyl ring in an alcoholic solvent, optionally at elevated temperature, and in the presence of a heterocycle, to form Compound II-A2'/II-A2;
  step 3) treating Compound II-A2'/II-A2 with a heterocycle in an alcoholic solvent, optionally at elevated temperature, to form Compound II-A3'/II-A3; and
  step 4) treating Compound II-A3'/II-A3 with a Grignard reagent or methyl anion in a heterocyclic solvent, to produce the compound of Formula II.

In some embodiments, the present invention provides a process for the preparation of a compound of Formula II, whereby crude compound of Formula II is slurried with a mixture comprising ethanol acetate, SiO$_2$ and charcoal, followed by solvent exchange and crystallization. In some embodiments, the invention provides a process for the preparation of a compound of Formula II, whereby the crude compound of Formula II is slurried with ethyl acetate, SiO$_2$ and charcoal and then solvent exchanged with a mixture of n-heptane/ethyl acetate and crystallized. In some embodiments, the crystallization upon solvent exchange results in the desired compound of Formula II. In some embodiments, the crude compound of Formula II is not purified by chromatography.

In some embodiments, Compound II-A1'/II-A1 is isolated and purified prior to its treatment with the optionally substituted phenyl ring to yield Compound II-A2'/II-A2. In some embodiments, Compound II-A2'/II-A2 is isolated and purified prior to its treatment with a heterocycle to yield Compound II-A3'/II-A3.

In some embodiments, one or more of the following conditions are satisfied with respect to steps 1-4 above for compound of Formula II:
  a) the compound of Formula II produced in step 4) is crude and are not purified by chromatography;
  b) the compound of Formula II produced in step 4) is slurried with a mixture comprising ethanol acetate, SiO$_2$ and charcoal, followed by solvent exchange and crystallization;
  c) Compound II-A1'/II-A1 is isolated and purified prior to treatment with an optionally substituted phenyl ring; and
  d) Compound II-A2'/II-A2 is isolated and purified prior to its treatment with a heterocycle.

In some embodiments, in the process for preparing the compound of Formula II, at least one of conditions b), c) and d) is satisfied. In some embodiments, at two of conditions b), c) and d) are satisfied. In some embodiments, all of conditions a) to d) are satisfied.

In some embodiments, the present invention provides a process for the preparation of a compound of Formula IV, comprising:
  step 1) treating pyruvate starting material with a heterocycle to produce Compound IV-A1'/IV-A1;
  step 2) treating Compound IV-A1'/IV-A1 with Ring A above to form Compound IV-A2'/IV-A2;
  step 3) treating Compound IV-A2'/IV-A2 with a heterocycle to form Compound IV-A3'/IV-A3; and
  step 4) treating Compound V-A3'/IV-A3 with a Grignard reagent or methyl anion to produce the compound of Formula IV.

In some embodiments, the present invention provides a process for the preparation of a compound of Formula IV comprising:
  step 1) treating pyruvate starting material with a heterocycle in an alcoholic solvent, optionally at elevated temperature, to produce Compound IV-A1'/IV-A1;
  step 2) treating Compound IV-A1'/IV-A1 with Ring A in an alcoholic solvent, optionally at elevated temperature, and in the presence of a heterocycle, to form Compound IV-A2'/V-A2;
  step 3) treating Compound IV-A2'/IV-A2 with a heterocycle in an alcoholic solvent, optionally at elevated temperature, to form Compound IV-A3'/IV-A3; and
  step 4) treating Compound IV-A3'/IV-A3 with a Grignard reagent or methyl anion in a heterocyclic solvent, to produce the compound of Formula IV.

In some embodiments, the invention provides a process for the preparation of a compound of Formula IV, whereby a crude compound of Formula IV are slurried with a mixture comprising ethanol acetate, SiO$_2$ and charcoal, followed by solvent exchange and crystallization. In some embodiments, the invention provides a process for the preparation of a compound of Formula IV, whereby a crude compound of Formula IV is slurried with ethyl acetate, SiO$_2$ and charcoal and then solvent exchanged with a mixture of n-heptane/ethyl acetate and crystallized. In some embodiments, the crystallization upon solvent exchange results in the desired compound of Formula IV. In some embodiments, the crude compound of Formula IV is not purified by chromatography. In some embodiments, the crude compound of Formula IV is not purified by column chromatography.

In some embodiments, Compound IV-A1'/IV-A1 is isolated and purified prior to its treatment with Ring A to yield Compound IV-A2'/IV-A2. In some embodiments, Compound IV-A2'/IV-A2 is isolated and purified prior to its treatment with a heterocycle to yield Compound IV-A3'/IV-A3.

In some embodiments, one or more of the following conditions are satisfied with respect to steps 1-4 above for compound of Formula IV:

a) the compound of Formula IV produced in step 4) are crude and are not purified by chromatography;

b) the compound of Formula IV produced in step 4) are slurried with a mixture comprising ethanol acetate, SiO$_2$ and charcoal, followed by solvent exchange and crystallization;

c) Compound IV-A1'/IV-A1 is isolated and purified prior to treatment with Ring A; and d) Compound IV-A2'/IV-A2 is isolated and purified prior to its treatment with a heterocycle.

In some embodiments, in the process for preparing a compound of Formula IV, at least one of conditions b), c) and d) are satisfied. In some embodiments, at two of conditions b), c) and d) are satisfied. In some embodiments, all of conditions a) to d) are satisfied.

U.S. patent application Ser. No. 13/709,802, filed Dec. 10, 2012 and published as US 2013/0190500 on Jul. 25, 2013 ("the '500 publication," the entirety of which is hereby incorporated herein by reference), describes certain aldehyde scavenging compounds. Such compounds include Compound A:

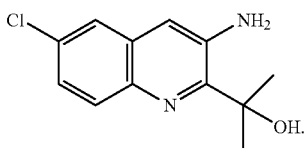

Compound A, (6-chloro-3-amino-2-(2-hydroxypropyl)-1-azanaphthalene), is designated as Compound A in the '500 publication and the synthesis of Compound A is described in detail at Example 5 of the '500 publication and is reproduced for ease of reference as Scheme 3a, below.

Scheme 3a: Synthesis of Compound A.

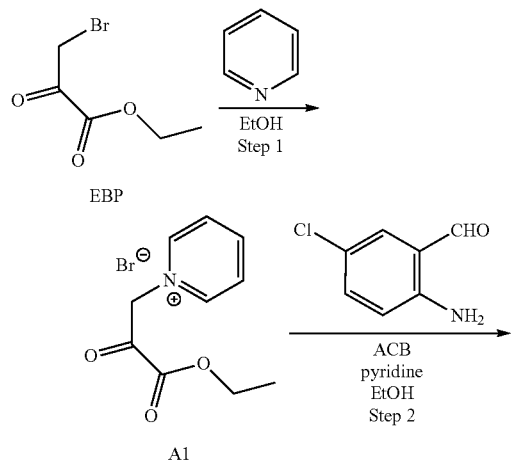

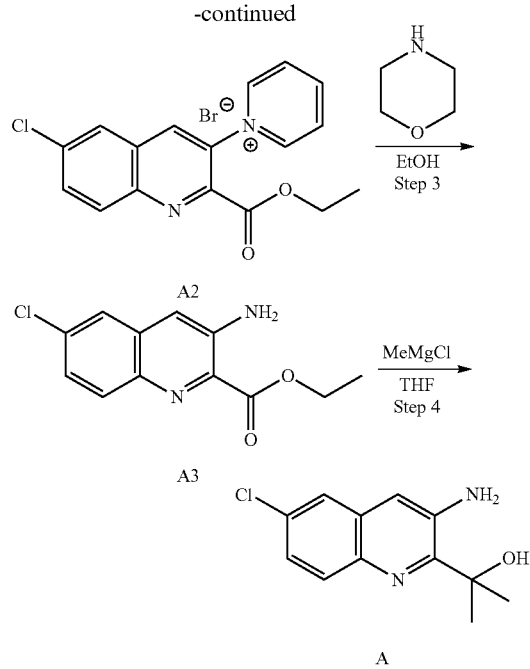

The details of the above synthetic Scheme 3a, from the '500 publication, are found therein.

In the present disclosure, novel processes for synthesis of Compound A have been developed with commercial scalability advantages. The resulting Compound A from these novel processes has been characterized against resulting Compound A made by the process set forth in the '500 publication summarized above. These comparisons are discussed in more detail below.

The process of the '500 publication has four intermediates: A1, A2, A3 and crude Compound A. Two of the intermediates, A3 and crude Compound A, are isolated before final purification to Compound A according to the '500 publication. The novel process for synthesis of Compound A in the present disclosure includes: 1) replacement of ethyl bromopyruvate (EBP) with Compound A2 due to reliability and quality of commercially sourced EBP; and 2) the removal of the crude Compound A chromatographic purification in the '500 publication and replacement with silicon-oxide treatment, precipitation and filtration from a charcoal slurry. Differences between the synthetic processes of the '500 publication and the novel processes described herein are summarized below.

In the '500 publication, the process is telescoped though to the first isolated intermediate, which is Compound A3. In the novel process described herein, these steps are not telescoped, and points of purity control have been introduced. Isolation of Compound A1 and/or A2 and the impurity analysis introduces a point of significant impurity control. For instance, the varying purity from the EBP starting material may be controlled during the isolation.

In the '500 publication, the aminochlorobenzaldehyde (ACB) and EBP are the starting raw materials and the synthesis is telescoped with no isolations until Compound A3. In the novel process described herein, synthesis and isolation of Compound A1 and/or A2 is a discrete step with a yield and purity obtained at the end of reaction.

In the '500 publication, the crude Compound A is purified by column chromatography followed by charcoal treatment and crystallisation to obtain material of sufficient purity. In the novel processes described herein, column chromatography may be eliminated, and crude Compound A may be slurried with a mixture comprising ethanol acetate, $SiO_2$ and charcoal, followed by solvent exchange in n-heptane/EtOAc before crystallization. It has been found that removing column chromatography improves the operability of the process at scale, while the $SiO_2$ treatment has been observed to remove baseline impurities and the charcoal treatment has been demonstrated to aid color control.

Thus, in some embodiments, the present invention provides a process for preparation of Compound A according to Scheme 3 below:

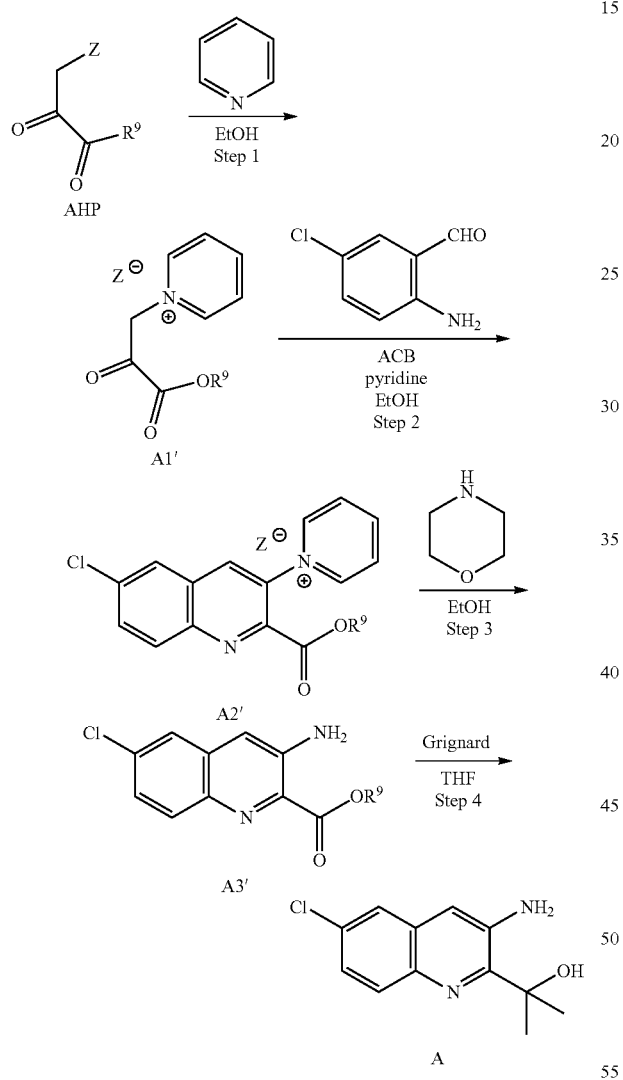

wherein $R^9$ is an aliphatic group, in particular a $C_{1-6}$aliphatic, preferably a $C_{1-6}$alkyl, more preferably methyl, ethyl, or propyl, preferably ethyl; and Z is fluoro (F), chloro (Cl), or bromo (Br), preferably Br. In some embodiments, the Grignard reagent is MeMgY, where Y is Cl, Br or Cl, preferably MeMgCl.

Thus, in some embodiments, the present invention provides a process for the preparation of Compound A (6-chloro-3-amino-2-(2-hydroxypropyl)-1-azanapthalene) based on Scheme 3, comprising:

step 1) treating an alkylhalopyruvate (AHP)

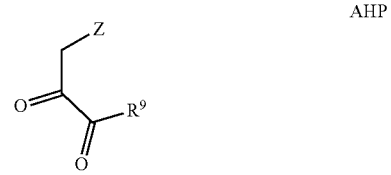

wherein Z is halogen and $R^9$ is a $C_{1-6}$aliphatic with pyridine to form Compound A1, alkyl pyridyliumpyruvate halide:

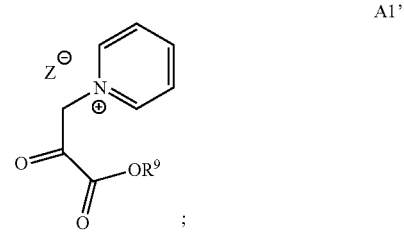

step 2) treating Compound A1' with 2-amino-5-chlorobenzaldehyde (ACB) and pyridine to form Compound A2', 6-chloro-3-pyridylium-2-alkoxycarbonyl-1-azanapthalene halide:

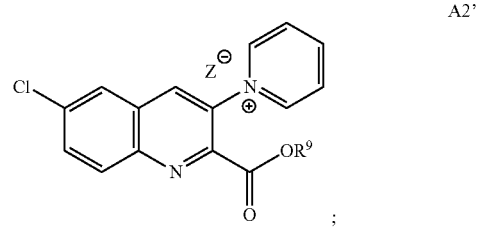

step 3) treating Compound A2' with a suitable heterocycle (e.g., morpholine) to form Compound A3', 6-chloro-3-amino-2-alkoxycarbonyl-1-azanaphthalene:

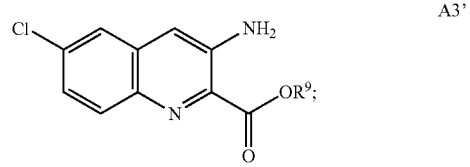

step 4) treating Compound A3' with a Grignard reagent (e.g., methylmagnesium chloride) to form Compound A;

wherein one or more of the following conditions are satisfied:
  a) Compound A formed in step 4) is crude and is not purified by chromatography;
  b) Compound A formed in step 4) is slurried with a mixture comprising ethanol acetate, $SiO_2$ and charcoal, followed by solvent exchange and crystallization;
  c) Compound A1' is isolated and purified prior to treatment with an optionally substituted phenyl ring; and d) Compound A2' is isolated and purified prior to its treatment with a heterocycle.

In some embodiments, the process for preparation of Compound A includes at least one of conditions b), c) and d). In some embodiments, the process includes at least two of conditions b), c) and d). In some embodiments, all of conditions a) to d) are satisfied.

In some embodiments, the pyridine in step 1) is replaced with a suitable heterocycle, particularly an N-containing heterocycle, such as described for synthesis of a compound of Formula II.

In some embodiments, the suitable heterocycle in step 3) is morpholine, or other such heterocycles, such as described for synthesis of a compound of Formula II.

In some embodiments, the present invention provides a process for the preparation of Compound A (e.g., 6-chloro-3-amino-2-(2-hydroxypropyl)-1-azanapthalene) based on Scheme 3 above, comprising:
step 1) treating alkyl halopyruvate (AHP) with pyridine in ethanol at elevated temperature to form Compound A1' (e.g., alkyl pyridyliumpyruvate halide);
step 2) treating Compound A1' with ACB (e.g., 2-amino-5-chloro-benzaldehyde) and pyridine at elevated temperature to form Compound A2' (e.g., 6-chloro-3-pyridylium-2-alkoxycarbonyl-1-azanapthalene halide);
step 3) treating Compound A2' with a suitable heterocycle at elevated temperature to form Compound A3' (e.g., 6-chloro-3-amino-2-alkoxycarbonyl-1-azanaphthalene); and
step 4) treating Compound A3' with a Grignard reagent (e.g., methylmagnesium chloride) to form Compound A.

In some embodiments, the present invention provides a process for the preparation of Compound A (6-chloro-3-amino-2-(2-hydroxypropyl)-1-azanapthalene) based on Scheme 3a above, comprising:
step 1) treating ethyl bromopyruvate (EBP)

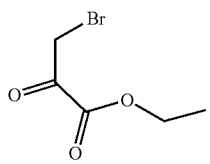

EBP with pyridine to form Compound A1, ethyl pyridyliumpyruvate halide:

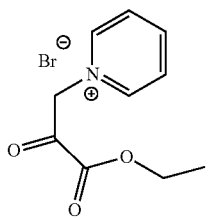

A1 step 2) treating Compound A1 with 2-amino-5-chloro-benzaldehyde (ACB) and pyridine to form Compound A2, 6-chloro-3-pyridylium-2-ethoxycarbonyl-1-azanapthalene halide:

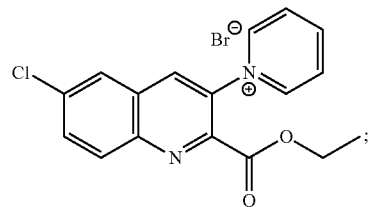

A2 step 3) treating Compound A2 with morpholine to form Compound A3, 6-chloro-3-amino-2-ethoxycarbonyl-1-azanaphthalene:

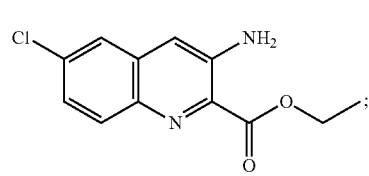

A3 step 4) treating Compound A3 with methylmagnesium chloride to form Compound A;
wherein one or more of the following conditions are satisfied:
a) Compound A formed in step 4) is crude and is not purified by chromatography;
b) Compound A formed in step 4) is slurried with a mixture comprising ethanol acetate, SiO$_2$ and charcoal, followed by solvent exchange and crystallization;
c) Compound A1 is isolated and purified prior to treatment with ACB; and
d) Compound A2 is isolated and purified prior to its treatment with a heterocycle.

In some embodiments, the process for preparation of Compound A based on Scheme 3 satisfies at least one of conditions b), c) and d). In some embodiments, the process satisfies at least two of conditions b), c) and d). In some embodiments, all of conditions a) to d) are satisfied.

In some embodiments, the present invention provides a process for the preparation of Compound A (e.g., 6-chloro-3-amino-2-(2-hydroxypropyl)-1-azanapthalene) based on Scheme 3 above, comprising:
step 1) treating ethyl bromopyruvate (AHP) with pyridine in ethanol at elevated temperature to form Compound A1 (e.g., ethyl pyridyliumpyruvate halide);
step 2) treating Compound A1 with ACB (e.g., 2-amino-5-chloro-benzaldehyde) and pyridine at elevated temperature to form Compound A2 (e.g., 6-chloro-3-pyridylium-2-ethoxycarbonyl-1-azanapthalene halide);
step 3) treating Compound A2 with morpholine at elevated temperature to form Compound A3 (e.g., 6-chloro-3-amino-2-ethoxycarbonyl-1-azanaphthalene); and
step 4) treating Compound A3 with methylmagnesium chloride to form Compound A.

In some embodiments, whether based on Scheme 3 or 3a, Compound A is purified and isolated by slurrying with a mixture comprising ethanol acetate, SiO$_2$ and charcoal, followed by solvent exchange with a mixture of n-heptane/ethyl acetate and crystallization.

In some embodiments, the invention provides a process for the preparation of Compound A comprising treating Compound A2' or A2 with morpholine at elevated temperature followed by treating the product thereof with a Grignard reagent, e.g., methyl-magnesium chloride. In some embodiments, the invention provides a process for the preparation of Compound A3' or A3 comprising treating Compound A2' or A2 with morpholine at elevated temperature.

In some embodiments, the invention provides a process for the preparation of Compound A comprising treating Compound A3' or A3 with a Grignard reagent, e.g., methylmagnesium chloride. In some embodiments, the resulting product is crude Compound A, and crude Compound A is purified by slurrying with ethanol acetate, $SiO_2$ and charcoal and then solvent exchanged with a mixture of n-heptane/ethyl acetate and crystallized. In some embodiments, the crystallization upon solvent exchange results in the desired Compound A. In some embodiments, crude Compound A is not purified by chromatography. In some embodiments, crude Compound A is not purified by column chromatography.

In some embodiments, the invention provides a process for the preparation of Compound A2' or A2 comprising treating Compound A1' or A1 with ACB (e.g., 2-amino-5-chloro-benzaldehyde) and pyridine at elevated temperature. In some embodiments, the invention provides a process for the preparation of Compound A1' or A1 comprising treating alkyl halopyruvate (AHP), e.g., ethyl bromopyruvate (EBP), with pyridine in ethanol at elevated temperature. In some embodiments, the invention provides a process for the preparation of ACB (e.g., 2-amino-5-chloro-benzaldehyde) comprising treating 5-chloro-2-nitrobenzaldehyde with hydrogen and platinum, 3% on activated carbon, sulfided.

In some embodiments, Compound A1' or A1 is isolated and purified prior to its treatment with ACB and pyridine to yield Compound A2' or A2. In some embodiments, Compound A2' or A2 is isolated and purified prior to its treatment with morpholine at elevated temperature to yield Compound A3' or A3.

In some embodiments, the elevated temperature may be about 50° C. to about 150° C. In some embodiments, the elevated temperature may be about 50° C. to about 100° C. In some embodiments, the elevated temperature may be about 60° C. to about 90° C. In some embodiments, the elevated temperature may be about 70° C. to about 80° C. In some embodiments, the elevated temperature may be about 65° C. to about 75° C.

In some embodiments, the invention provides a process for the preparation of Compound A (e.g., 6-chloro-3-amino-2-(2-hydroxypropyl)-1-azanapthalene) comprising treating Compound A2' or A2 with morpholine at about 80° C. followed by treating the product thereof with methylmagnesium chloride. In some embodiments, the invention provides a process for the preparation of Compound A3' or A3 comprising treating Compound A2' or A2 with morpholine at about 80° C.

In some embodiments, one or more of the following conditions are satisfied with respect to steps 1-4 above:
 a) Compound A formed in step 4) is crude and is not purified by chromatography;
 b) Compound A formed in step 4) is slurried with a mixture comprising ethanol acetate, $SiO_2$ and charcoal, followed by solvent exchange and crystallization;
 c) Compound A1' or A1 is isolated and purified prior to treatment with ACB; and
 d) Compound A2' or A2 is isolated and purified prior to its treatment with a heterocycle.

In some embodiments, the steps 1-4 above includes at least one of conditions b), c) and d). In some embodiments, at least two of conditions b), c) and d) are satisfied. In some embodiments, all of conditions a) to d) are satisfied.

In some embodiments, the present disclosure provides novel synthetic processes for production of Compound A on a commercial scale, whereby points of purity control are introduced. In some embodiments, the invention provides isolation of intermediate Compounds A1' or A1, and/or A2' or A2 for purity control purposes. In some embodiments, Compound A1' or A1 is isolated for purity control purposes. In some embodiments, intermediate Compound A2' or A2 is isolated for purity control purposes. In some embodiments, intermediate Compounds A1 and A2, or A1' and A2' are isolated for purity control purposes.

In some embodiments, impurities associated with step 1 are controlled. In some embodiments, there is no telescoping associated with steps 1 and 2 of the Synthetic Schemes for Compound A described herein. In some embodiments, intermediate Compound A2 or A2' is isolated and yield and purity is determined.

In some embodiments, Compound A is purified by slurrying with ethyl acetate, $SiO_2$ and charcoal. In some embodiments, the slurry is then solvent exchanged in an n-heptane/EtOAc mixture. In some embodiments, Compound A is crystallized after the solvent exchange. In some embodiments, the $SiO_2$ treatment removes baseline impurities. In some embodiments, the charcoal treatment aids color control.

2. Synthesis of Compound B

In some embodiments, the process for making Compound A can also be adapted to making Compound B, having the structure below:

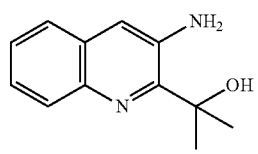

B

In some embodiments, an exemplary process for preparing Compound B is shown in Scheme 4, below:

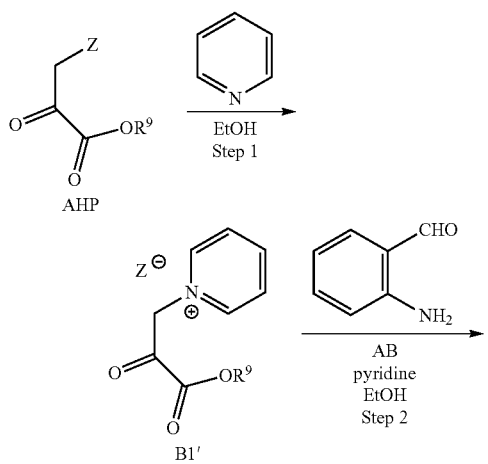

-continued

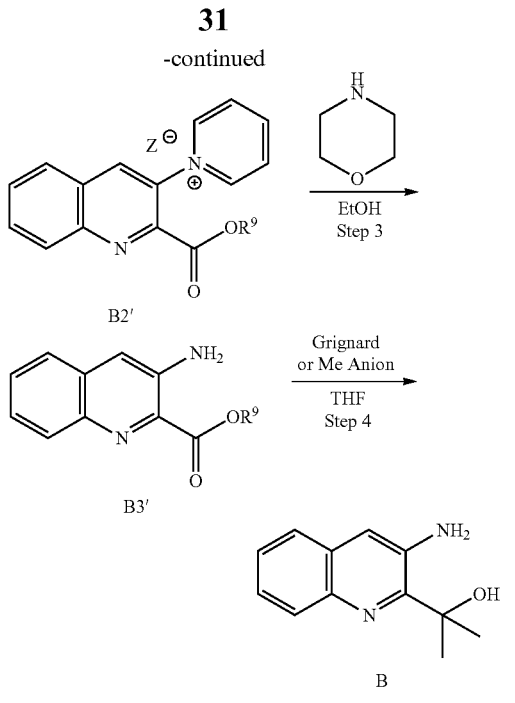

B2'

B3'

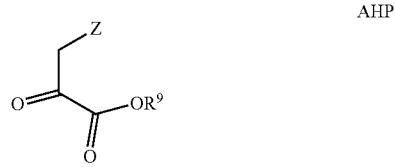

B wherein $R^9$ is an aliphatic, in particular a $C_{1-6}$aliphatic, preferably a $C_{1-6}$alkyl, more preferably methyl, ethyl, or propyl; and Z is a halogen, preferably fluoro (Fl), bromo (Br), or chloro (Cl), preferably Br. In some embodiments, the Grignard reagent is MeMgY, where Y is Cl, Br or Cl, e.g., MeMgCl. In some embodiments, the Me-Anion is, for example, MeM, where M is Li, Sr, Ce, or Co; $Me_2CuLi$ or mixed cuprates with I, Br, or Cl; or $AlMe_3$ (trimethylaluminum).

In some embodiments, the present invention provides a process for the preparation of Compound B (3-amino-2-(2-hydroxypropyl)-1-azanapthalene) based on Scheme 4, comprising:

step 1) treating an alkyl halopyruvate (AHP)

AHP

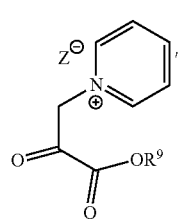

wherein Z is halogen and $R^9$ is a $C_{1-6}$aliphatic with pyridine to form Compound B1', alkyl pyridyliumpyruvate halide:

B1

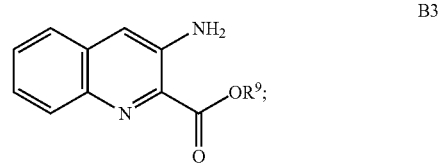

step 2) treating Compound B1' with 2-amino-benzaldehyde (AB) and pyridine to form Compound B2', 3-pyridylium-2-alkoxycarbonyl-1-azanapthalene halide:

B2

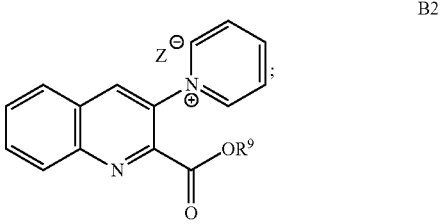

step 3) treating Compound B2' with a suitable heterocycle (e.g., morpholine) to form Compound B3', 3-amino-2-alkoxycarbonyl-1-azanaphthalene:

B3 step 4) treating Compound B3' with a Grignard reagent or Methyl Anion to form Compound B.

In some embodiments, an exemplary Grignard reagent is MeMgY, where Y is Cl, Br or Cl. In some embodiments, the Me-Anion is, for example, MeM, where M is Li, Sr, Ce, or Co; $Me_2CuLi$ or mixed cuprates with I, Br, or Cl; or $AlMe_3$ (trimethylaluminum).

In some embodiments, Compound B produced by the foregoing process can be further purified, for example by chromatography.

In some embodiments, Compound B1' produced by the foregoing process is isolated and purified.

In some embodiments, Compound B2' produced by the foregoing process is isolated and purified.

In some embodiments, Compound B3' is isolated and purified prior to reaction with a Grignard or methyl anion.

In some embodiments, the pyridine in step 1) is replaced with a suitable heterocycle, particularly an N-containing heterocycle, such as described for synthesis of a compound of Formula II.

In some embodiments, the suitable heterocycle in step 3) is morpholine, or other such heterocycles, such as described for synthesis of a compound of Formula II.

In some embodiments, one or more of the following conditions are satisfied in the process based on Scheme 4 for preparing Compound B:
a) Compound B formed in step 4) is crude and is not purified by chromatography; or
b) Compound B formed in step 4) is slurried with a mixture comprising ethanol acetate, $SiO_2$ and charcoal, followed by solvent exchange and crystallization; or
c) Compound B1' is isolated and purified prior to treatment with AB; and
d) Compound B2' is isolated and purified prior to its treatment with a heterocycle.

In some embodiments, the process for preparing Compound B includes at least one of conditions b), c) and d). In some embodiments, the process includes at least two of conditions b), c) and d). In some embodiments, all of conditions a) to d) are satisfied.

In some embodiments, the invention provides a process for the preparation of Compound B (3-amino-2-(2-hydroxy-propyl)-1-azanapthalene) comprising:

step 1) treating alkylhalopyruvate (AHP) with pyridine in ethanol at elevated temperature to form Compound B1' (e.g., alkyl pyridyliumpyruvate halide);

step 2) treating Compound B1' with AB (e.g., 2-amino-benzaldehyde) and pyridine at elevated temperature to form Compound B2' (e.g., 3-pyridylium-2-alkoxycar-bonyl-1-azanapthalene halide);

step 3) treating Compound B2' with a suitable heterocycle (e.g., morpholine) at elevated temperature to form Compound B3' (e.g., 3-amino-2-alkoxycarbonyl-1-azanaphthalene); and step 4) treating Compound B3' with a Grignard reagent or Me-Anion to form Compound B.

In some embodiments, the present invention provides a process for the preparation of Compound B (3-amino-2-(2-hydroxypropyl)-1-azanapthalene) based on Scheme 4a, below.

Scheme 4a: Synthesis of Compound B

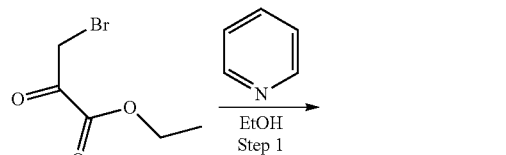

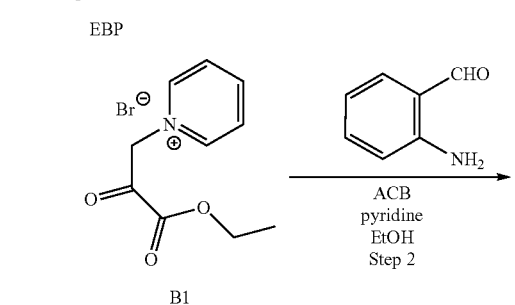

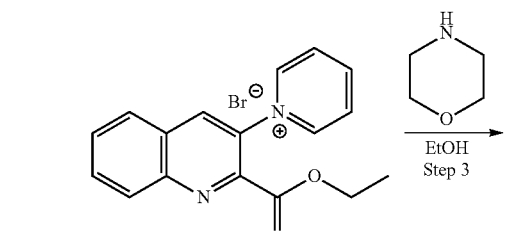

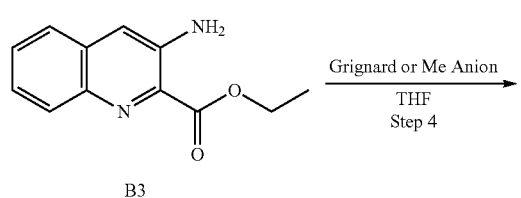

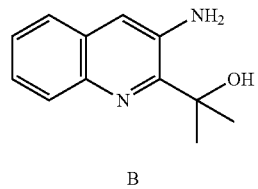

B

In some embodiments of Scheme 4a, the Grignard reagent is MeMgY, where Y is Cl, Br or Cl, e.g., MeMgCl. In some embodiments, the Me-Anion is, for example, MeM, where M is Li, Sr, Ce, or Co; Me$_2$CuLi or mixed cuprates with I, Br, or Cl; or AlMe$_3$ (trimethylaluminum).

In some embodiments, the present invention provides a process for the preparation of Compound B (3-amino-2-(2-hydroxypropyl)-1-azanapthalene) based on Scheme 4a, comprising:

step 1) treating ethyl bromopyruvate (EBP)

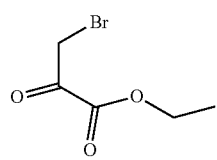

EBP with pyridine to form Compound B1, ethyl pyridyliumpy-ruvate halide:

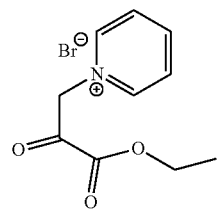

B1 step 2) treating Compound B1 with 2-amino-benzalde-hyde (AB) and pyridine to form Compound B2, 3-pyridylium-2-ethoxycarbonyl-1-azanapthalene halide:

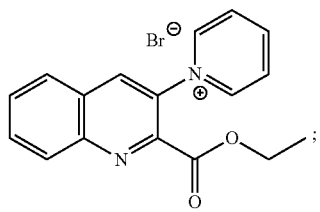

B2 step 3) treating Compound B2 with morpholine to form Compound B3, 3-amino-2-ethoxycarbonyl-1-azanaph-thalene:

step 4) treating Compound B3 with a Grignard reagent or methyl-anion to form Compound B.

In some embodiments, an exemplary Grignard reagent is MeMgY, where Y is Cl, Br or Cl. In some embodiments, the Me-Anion is, for example, MeM, where M is Li, Sr, Ce, or Co; Me$_2$CuLi or mixed cuprates with I, Br, or Cl; or AlMe$_3$ (trimethylaluminum).

In some embodiments, Compound B produced by the foregoing process can be further purified, for example by chromatography.

In some embodiments, Compound B1 produced by the foregoing process is isolated and purified.

In some embodiments, Compound B2 produced by the foregoing process is isolated and purified.

In some embodiments, Compound B3 is isolated and purified prior to reaction with a Grignard or methyl anion.

In some embodiments, one or more of the following conditions are satisfied in the process based on Scheme 4a for preparing Compound B:
  a) Compound B formed in step 4) is crude and is not purified by chromatography; or
  b) Compound B formed in step 4) is slurried with a mixture comprising ethanol acetate, SiO$_2$ and charcoal, followed by solvent exchange and crystallization; or
  c) Compound B1 is isolated and purified prior to treatment with AB; and
  d) Compound B2 is isolated and purified prior to its treatment with a heterocycle.

In some embodiments, the process for preparing Compound B includes at least one of conditions b), c) and d). In some embodiments, the process includes at least two of conditions b), c) and d). In some embodiments, all of conditions a) to d) are satisfied.

In some embodiments, the invention provides a process for the preparation of Compound B (3-amino-2-(2-hydroxypropyl)-1-azanapthalene) comprising:
  step 1) treating ethyl bromopyruvate (EBP) with pyridine in ethanol at elevated temperature to form Compound B1 (e.g., ethyl pyridyliumpyruvate halide);
  step 2) treating Compound B1 with AB (e.g., 2-aminobenzaldehyde) and pyridine at elevated temperature to form Compound B2 (e.g., 3-pyridylium-2-ethoxycarbonyl-1-azanapthalene halide);
  step 3) treating Compound B2 with morpholine at elevated temperature to form Compound B3 (e.g., 3-amino-2-ethoxycarbonyl-1-azanaphthalene); and
  step 4) treating Compound B3 with a Grignard reagent or Me-Anion to form Compound B.

In some embodiments, whether based on Scheme 4 or 4a, Compound B is purified and isolated by slurrying with a mixture comprising ethanol acetate, SiO$_2$ and charcoal, followed by solvent exchange with a mixture of n-heptane/ethyl acetate and crystallization.

In some embodiments, the present invention provides a process for the preparation of Compound B comprising treating Compound B2' or B2 with morpholine at elevated temperature followed by treating the product thereof with a Grignard reagent or methyl anion. In some embodiments, the invention provides a process for the preparation of Compound B3' or B3 comprising treating Compound B2' or B2 with morpholine at elevated temperature.

In some embodiments, the present invention provides a process for the preparation of Compound B comprising treating Compound B3' or B3 with a Grignard reagent or methyl anion. In some embodiments, the resulting product is crude Compound B, and crude Compound B is purified by slurrying with ethanol acetate, SiO$_2$ and charcoal and then solvent exchanged with a mixture of n-heptane/ethyl acetate and crystallized. In some embodiments, the crystallization upon solvent exchange results in the desired Compound B. In some embodiments, crude Compound B is not purified by chromatography. In some embodiments, crude Compound B is not purified by column chromatography.

In some embodiments, the invention provides a process for the preparation of Compound B2' or B2 comprising treating Compound B1' or B1 with AB (e.g., 2-aminobenzaldehyde) and pyridine at elevated temperature. In some embodiments, the invention provides a process for the preparation of Compound B1' or B1 comprising treating ethyl bromopyruvate (EBP) with pyridine in ethanol at elevated temperature.

In some embodiments, Compound B1' or B1 is isolated and purified prior to its treatment with AB and pyridine to yield Compound B2' or B2. In some embodiments, Compound B2' or B2 is isolated and purified prior to its treatment with morpholine at elevated temperature to yield Compound B3' or B3.

In some embodiments, the elevated temperature may be about 50° C. to about 150° C. In some embodiments, the elevated temperature may be about 50° C. to about 100° C. In some embodiments, the elevated temperature may be about 60° C. to about 90° C. In some embodiments, the elevated temperature may be about 70° C. to about 80° C. In some embodiments, the elevated temperature may be about 65° C. to about 75° C.

In some embodiments, the invention provides a process for the preparation of Compound B comprising treating Compound B2' or B2 with morpholine at about 80° C. followed by treating the product thereof with a Grignard reagent or methyl anion. In some embodiments, the invention provides a process for the preparation of Compound B3' or B3 comprising treating Compound B2' or B2 with morpholine at about 80° C.

In some embodiments, one or more of the following conditions are satisfied with respect to steps 1-4 for preparation of Compound B above:
  a) Compound B formed in step 4) is crude and is not purified by chromatography;
  b) Compound B formed in step 4) is slurried with a mixture comprising ethanol acetate, SiO$_2$ and charcoal, followed by solvent exchange and crystallization;
  c) Compound B1' or B1 is isolated and purified prior to treatment with AB; and
  d) Compound B2' or B2 is isolated and purified prior to its treatment with a heterocycle.

In some embodiments, the steps 1-4 includes at least one of conditions b), c) and d). In some embodiments, the steps 1-4 includes at least two of conditions b), c) and d). In some embodiments, all of conditions a) to d) are satisfied.

In some embodiments, the present disclosure provides novel synthetic processes for production of Compound B on a commercial scale, whereby points of purity control are introduced. In some embodiments, the invention provides isolation of Compounds B1' or B1, and/or B2' or B2 for purity control purposes. In some embodiments, intermediate Compound B1' or B1 is isolated for purity control purposes. In some embodiments, intermediate Compound B2' or B2 is isolated for purity control purposes. In some embodiments, intermediate Compounds B1' and B2', or B1 and B2 are isolated for purity control purposes.

In some embodiments, impurities associated with step 1 are controlled. In some embodiments, there is no telescoping associated with steps 1 and 2 of the Synthetic Schemes for Compound B described herein. In some embodiments, intermediate Compound B2' or B2 is isolated and yield and purity is determined.

In some embodiments, Compound B is purified by slurrying with ethyl acetate, $SiO_2$ and charcoal. In some embodiments, the slurry is then solvent exchanged in an n-heptane/EtOAc mixture. In some embodiments, Compound B is crystallized after the solvent exchange. In some embodiments, the $SiO_2$ treatment removes baseline impurities. In some embodiments, the charcoal treatment aids color control.

3. Alternative Process for Synthesis of Compound B and Related Compounds

In some embodiments, the present invention provides a process for preparing a compound of Formula IIa:

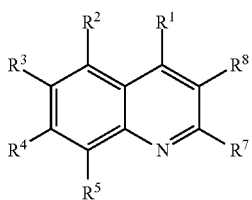

IIa or a pharmaceutically acceptable salt thereof, wherein:
each of $R^1$, $R^2$, $R^3$, $R^4$, and $R^5$ is independently H or D;
one of $R^7$ and $R^8$ is —$NH_2$ and other one of $R^7$ and $R^8$ is

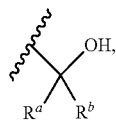

wherein
$R^a$ is $C_{1-4}$ aliphatic optionally substituted with 1, 2, or 3 deuterium or halogen atoms;
$R^1$ is $C_{1-4}$ aliphatic optionally substituted with 1, 2, or 3 deuterium or halogen atoms; or
$R^a$ and $R^b$, taken together with the carbon atom to which they are attached, form a 3- to 8-membered cycloalkyl or heterocyclyl ring containing 1-2 heteroatoms selected from nitrogen, oxygen, and sulfur.

In some embodiments, $R^7$ is

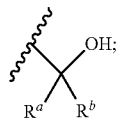

and
and $R^8$ is —$NH_2$.

In some embodiments, a process for preparing a compound of Formula IIa comprises hydrogenation of a compound of Formula IIb:

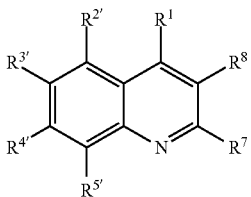

IIb wherein $R^1$ is H or D, and each of $R^{2'}$, $R^{3'}$, $R^{4'}$, and $R^{5'}$ is H, D, or halogen, wherein at least one of $R^{2'}$, $R^{3'}$, $R^{4'}$, and $R^{5'}$ is halogen; and $R^7$ and $R^8$ is as defined for Formula IIa;

wherein the hydrogenation is in presence of a suitable metal catalyst and hydrogen ($H_2$) in a suitable solvent under suitable conditions to form the compound of Formula IIa

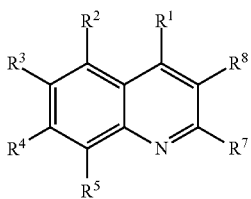

IIa

In some embodiments, the suitable metal catalyst for hydrogenation is palladium (Pd), platinum (Pt), or rhodium (Rb). In some embodiments, the suitable metal catalyst for hydrogenation is palladium on carbon. In some embodiments, the suitable solvent is an alcohol (e.g., methanol, ethanol, isopropanol, etc.), trimethylamine, tetrahydrofuran, ethyl acetate, toluene, water, or mixtures thereof. In some embodiments, the suitable solvent is a mixture of trimethylamine and ethyl acetate.

In some embodiments, the suitable conditions is hydrogen ($H_2$) at a pressure of about 5-30 psi, for example at 15 psi, and a temperature of about 30-35° C.

In some embodiments, the compound of Formula IIb is prepared using the synthetic Scheme 1 or 1a describe above except step 2) uses an optionally substituted amino benzaldehyde compound below:

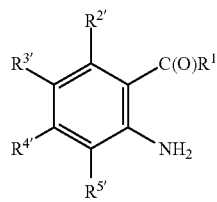

wherein $R^1$ is H or D, and each of $R^{2'}$, $R^{3'}$, $R^{4'}$, and $R^{5'}$ is H, D, or halogen, wherein at least one of $R^{2'}$, $R^{3'}$, $R^{4'}$, and $R^{5'}$ is halogen, to form compound of Formula IIb:

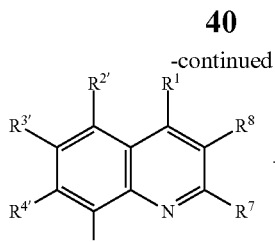

IIb

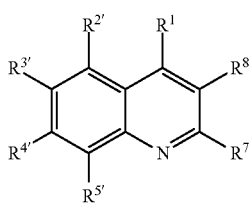

wherein R¹ is H or D, and each of R²', R³', R⁴', and R⁵' is H, D, or halogen, wherein at least one of R²', R³', R⁴', and R⁵' is halogen; and R⁷ and R⁸ is as defined for Formula IIa;

In some embodiments, an exemplary process for preparing a compound of Formula IIa is shown in Scheme 5:

Scheme 5: Synthesis of Compound of Formula IIa.

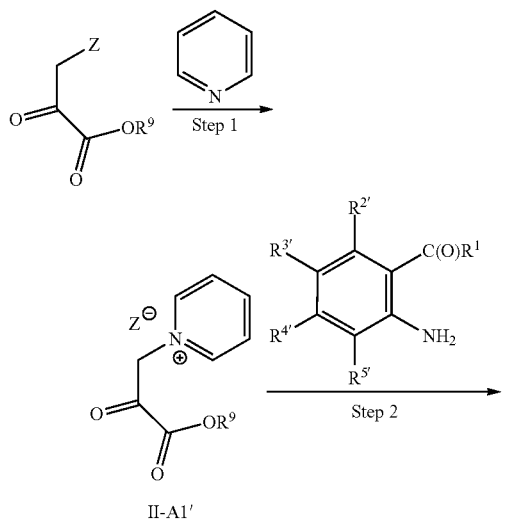

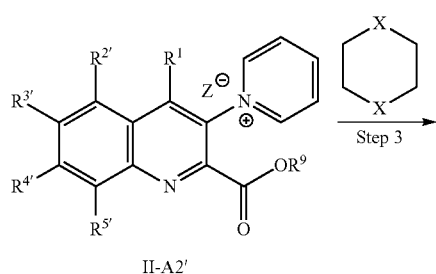

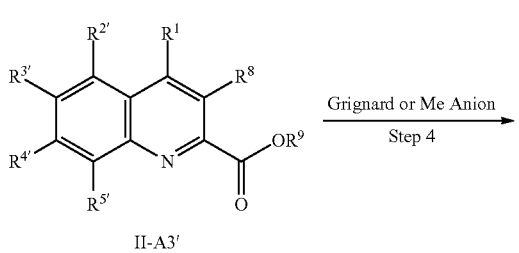

Formula IIb

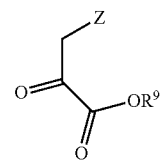

Formula IIa wherein, Z is a halogen, each X is independently —NH, O or S; each of R¹, R²', R³', R⁴', R⁵', R⁷ and R⁸ are as defined above for Formula IIb, and R⁹ is an aliphatic group, in particular a $C_{1-6}$aliphatic, preferably a $C_{1-6}$alkyl, more preferably methyl, ethyl, or propyl. In some embodiments, Z is fluoro (F), chloro (Cl), or bromo (Br), preferably Br.

In some embodiments, the Grignard reagent is an alkyl, vinyl or aryl Grignard reagent. In some embodiments, the Grignard reagent is an alkyl Grignard reagent. In some embodiments, the Grignard reagent is a methyl Grignard reagent. In some embodiments, the Grignard reagent is an ethyl Grignard reagent. In some embodiments, the Grignard reagent is a propyl Grignard reagent. In some embodiments, the Grignard reagent is an aryl Grignard reagent. In some embodiments, the Grignard reagent is MeMgY, where Y is Cl, Br or Cl. In some embodiments, the Me-Anion is, for example, MeM, where M is Li, Sr, Ce, or Co; Me₂CuLi or mixed cuprates with I, Br, or Cl; or AlMe₃ (trimethylaluminum). In some embodiments, an exemplary Grignard reagent is MeMgCl.

In some embodiments, the compound of Formula IIb is synthesized according to the process described in US 2013/0190500.

In some embodiments, the present invention provides a process for the preparation of a compound of Formula IIa, comprising:

step 1) treating an alkyl halopyruvate (AHP)

AHP wherein Z is halogen and R⁹ is a $C_{1-6}$aliphatic with pyridine to form Compound B1, alkyl pyridyliumpyruvate halide:

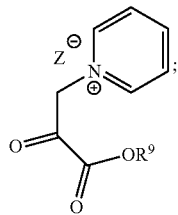

step 2) treating Compound II-A1' with an optionally substituted amino benzaldehyde

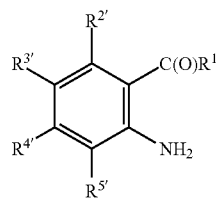

and pyridine to form Compound II-A2':

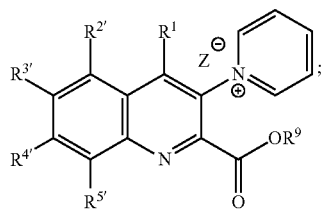

step 3) treating Compound II-A2' with a suitable heterocycle (e.g., morpholine) to form Compound II-A3':

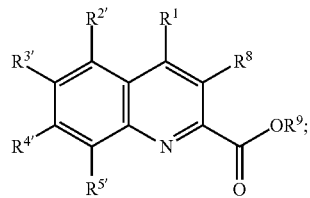

step 4) treating Compound II-A3' with a Grignard reagent or methyl anion to form the compound of Formula IIb; and step 5) hydrogenating Compound II-A3' in presence of a suitable metal catalyst, hydrogen ($H_2$) in a suitable solvent under suitable conditions to form a compound of Formula IIa.

In some embodiments, the compound of Formula IIa is further purified, for example by chromatography.

In some embodiments, the pyridine in step 1) is replaced with a suitable heterocycle, particularly an N-containing heterocycle, such as described for synthesis of a compound of Formula II.

In some embodiments, the suitable heterocycle in step 3) is morpholine, or other such heterocycles, such as described for synthesis of a compound of Formula II.

In some embodiments, in the process for preparing the compound of Formula IIa according to Scheme 5 describe above, one or more of the following conditions are satisfied:
  a) the compound of Formula IIb produced in step 4) is crude and is not purified by chromatography;
  b) the compound of Formula IIb produced in step 4) is slurried with a mixture comprising ethanol acetate, $SiO_2$ and charcoal, followed by solvent exchange and crystallization;
  c) Compound II-A1' is isolated and purified prior to treatment with an optionally substituted amino benzaldehyde; and
  d) Compound II-A2' is isolated and purified prior to its treatment with a heterocycle.

In some embodiments, the process based on Scheme 5 includes at least one of conditions b), c) and d). In some embodiments, at least two of conditions b), c) and d) are satisfied. In some embodiments, all of conditions a) to d) are satisfied.

In some embodiments, the compound of Formula IIb is not purified prior to hydrogenation. In some embodiments, the compound of Formula IIa formed in step 5) is slurried with a mixture comprising ethanol acetate, $SiO_2$ and charcoal, followed by solvent exchange and crystallization. In some embodiments, the process includes conditions c) and/or d).

In some embodiments, the present invention provides a process for the preparation of a compound of Formula IIa based on Scheme 5 above, comprising:
  step 1) treating an alkyl halopyruvate (AHP) with pyridine in ethanol at elevated temperature to form Compound II-A1';
  step 2) treating Compound II-A1' with the optionally substituted amino benzaldehyde and pyridine at elevated temperature to form Compound II-A2';
  step 3) treating Compound II-A2' with morpholine at elevated temperature to form Compound II-A3'; and
  step 4) treating Compound II-A3' with a Grignard reagent or methyl anion to form a compound of Formula IIb.

In some embodiments, prior to hydrogenation step, the compound of Formula IIb is purified and isolated by slurrying with a mixture comprising ethanol acetate, $SiO_2$ and charcoal, followed by solvent exchange with a mixture of n-heptane/ethyl acetate and crystallization.

In some embodiments, the present invention provides a process for the preparation of a compound of Formula IIb comprising treating Compound II-A2' with morpholine at elevated temperature followed by treating the product thereof with a Grignard reagent or methyl anion. In some embodiments, the present invention provides a process for the preparation of Compound II-A3' comprising treating Compound II-A2' with morpholine at elevated temperature.

In some embodiments, the present invention provides a process for the preparation of a compound of Formula IIb comprising treating Compound II-A3' with a Grignard reagent or methyl anion. In some embodiments, the resulting product is crude compound of Formula IIb, and crude compound of Formula IIb is purified by slurrying with ethanol acetate, $SiO_2$ and charcoal and then solvent exchanged with a mixture of n-heptane/ethyl acetate and crystallized. In some embodiments, the crystallization upon solvent exchange results in the desired compound of Formula IIb. In some embodiments, crude compound of Formula IIb is not purified by chromatography. In some embodiments, crude compound of Formula IIb is not purified by column chromatography.

In some embodiments, the invention provides a process for the preparation of Compound A2' comprising treating Compound II-A1' with the optionally substituted amino benzaldehyde and pyridine at elevated temperature. In some embodiments, the invention provides a process for the preparation of Compound II-A1' comprising treating alkyl halopyruvate (AHP) with pyridine in ethanol at elevated temperature.

In some embodiments, Compound II-A1' is isolated and purified prior to its treatment with the optionally substituted amino benzaldehyde and pyridine to yield Compound II-A2'. In some embodiments, Compound II-A2' is isolated and purified prior to its treatment with morpholine at elevated temperature to yield Compound II-A3'.

In some embodiments, the elevated temperature may be about 50° C. to about 150° C. In some embodiments, the elevated temperature may be about 50° C. to about 100° C. In some embodiments, the elevated temperature may be about 60° C. to about 90° C. In some embodiments, the elevated temperature may be about 70° C. to about 80° C. In some embodiments, the elevated temperature may be about 65° C. to about 75° C.

In some embodiments, the invention provides a process for the preparation of a compound of Formula IIb comprising treating Compound II-A2' with morpholine at about 80° C. followed by treating the product thereof with a Grignard reagent or methyl anion. In some embodiments, the invention provides a process for the preparation of Compound II-A3' comprising treating Compound II-A2' with morpholine at about 80° C.

In some embodiments, one or more of the following conditions are satisfied with respect to steps 1-4 above:
a) a compound of Formula IIb formed in step 4) is crude and is not purified by chromatography;
b) a compound of Formula IIb formed in step 4) is slurried with a mixture comprising ethanol acetate, SiO$_2$ and charcoal, followed by solvent exchange and crystallization;
c) Compound II-A1' is isolated and purified prior to treatment with an optionally substituted amino benzaldehyde; and
d) Compound II-A2' is isolated and purified prior to its treatment with a heterocycle.

In some embodiments, the steps 1-4 includes at least one of conditions b), c) and d). In some embodiments, at least two of conditions b), c) and d) are satisfied. In some embodiments, all of conditions a) to d) are satisfied.

In some embodiments in the process for preparing a compound of Formula IIa above, the alkyl halopyruvate (AHP) is ethyl bromopyruvate and the optionally substituted amino benzaldehyde is amino benzaldehyde. In some embodiments, a Grignard reagent is used, preferably MeMgCl.

Thus, in some embodiments, the present disclosure provides a processes for making Compound B:

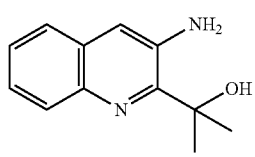

B comprising hydrogenating Compound A

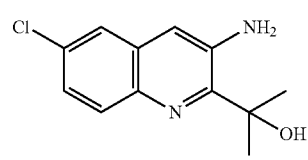

A in presence of a suitable metal catalyst and hydrogen (H$_2$) in a suitable solvent under suitable conditions to form Compound B.

In some embodiments, the suitable metal catalyst is palladium (Pd), platinum (Pt), or rhodium (Rb). In some embodiments, the suitable metal catalyst is palladium on carbon.

In some embodiments, the suitable solvent is an alcohol (e.g., methanol, ethanol, isopropanol, etc.), trimethylamine, tetrahydrofuran, ethyl acetate, toluene, water, or mixtures thereof.

In some embodiments, the suitable conditions for hydrogenation is hydrogen at a pressure of about 5-30 psi, for example at 15 psi, and a temperature of about 30-35° C.

In some embodiments, Compound B is synthesized based on Scheme 6, below, using Compound A, which can be synthesized according to the methods described herein for preparing Compound A.

Scheme 6: Preparation of Compound B

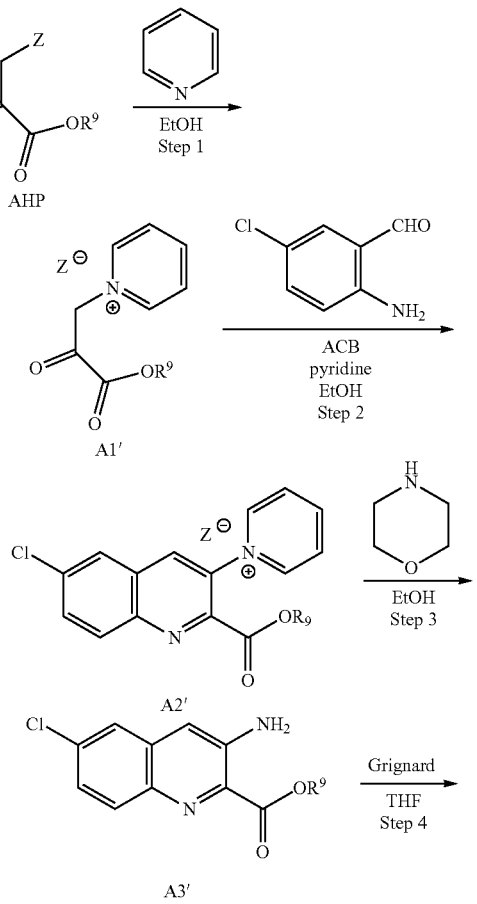

-continued

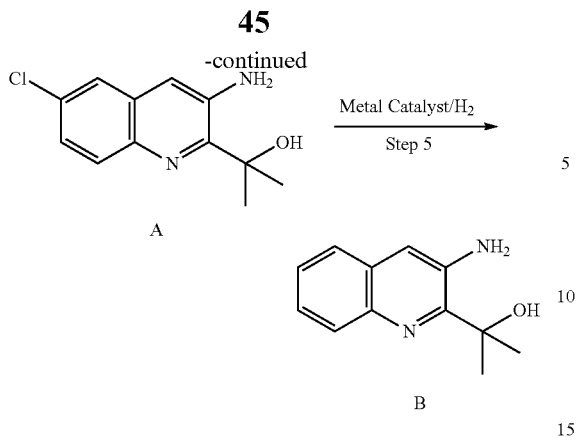

wherein, Z is a halogen; and $R^9$ is an aliphatic group, in particular a $C_{1-6}$aliphatic, preferably a $C_{1-6}$alkyl, more preferably methyl, ethyl, or propyl. In some embodiments, Z is fluoro (F), chloro (Cl), or bromo (Br), preferably Br. In some embodiments, the Grignard reagent is MeMgY, where Y is Cl, Br or Cl. In some embodiments, an exemplary Grignard reagent is MeMgCl.

In some embodiments, the present disclosure provides a process for the preparation of Compound B (3-amino-2-(2-hydroxypropyl)-1-azanapthalene) based on Scheme 6, comprising:

step 1) treating an alkyl halopyruvate (AHP)

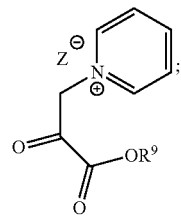

with pyridine to form Compound A1':

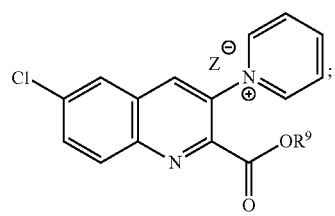

step 2) treating Compound A1' with 2-amino-5-chloro-benzaldehyde (ACB) and pyridine to form Compound A2':

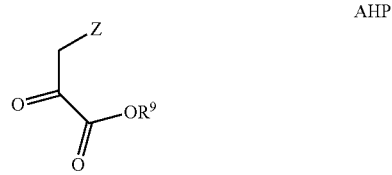

step 3) treating Compound A2' with a suitable heterocycle to form Compound A3':

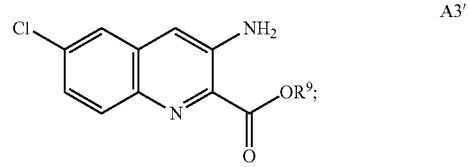

step 4) treating Compound A3' with a Grignard reagent (e.g., methylmagnesium chloride) to form Compound A:

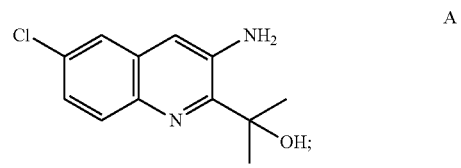 [SMILES: CC(C)(O)c1nc2ccc(Cl)cc2cc1N]

step 5) hydrogenating Compound A in presence of a suitable metal catalyst, hydrogen ($H_2$) in a suitable solvent under suitable conditions to form Compound B.

In some embodiments, the suitable metal catalyst is palladium (Pd), platinum (Pt), or rhodium (Rb). In some embodiments, the suitable metal catalyst is palladium on carbon.

In some embodiments, the suitable solvent for hydrogenation is an alcohol (e.g., methanol, ethanol, isopropanol, etc.), trimethylamine, tetrahydrofuran, ethyl acetate, toluene, water, or mixtures thereof.

In some embodiments, the suitable conditions for hydrogenation is hydrogen at a pressure of about 5-30 psi, for example at 15 psi, and a temperature of about 30-35° C.

In some embodiments, the pyridine in step 1) is replaced with a suitable heterocycle, particularly an N-containing heterocycle, such as described for synthesis of a compound of Formula II.

In some embodiments, the suitable heterocycle in step 3) is morpholine, or other such heterocycles, such as described for synthesis of a compound of Formula II.

In some embodiments, in the process for preparing Compound B based on Scheme 6 above, one or more of the following conditions are satisfied:

a) Compound A formed in step 4) is crude and is not purified by chromatography;
b) Compound A formed in step 4) is slurried with a mixture comprising ethanol acetate, $SiO_2$ and charcoal, followed by solvent exchange and crystallization;
c) Compound A1' is isolated and purified prior to treatment with an optionally substituted amino benzaldehyde; and
d) Compound A2' is isolated and purified prior to its treatment with a heterocycle.

In some embodiments, the process for preparation of Compound B includes at least one of conditions b), c) and d). In some embodiments, the process includes at least two of conditions b), c) and d). In some embodiments, all of conditions a) to d) are satisfied.

In some embodiments, Compound A is not purified prior to hydrogenation. In some embodiments, Compound B formed in step 5) is slurried with a mixture comprising ethanol acetate, SiO$_2$ and charcoal, followed by solvent exchange and crystallization. In some embodiments, the process includes conditions c) and/or d).

In some embodiments, the present invention provides a process for the preparation of Compound B based on Scheme 6 above, comprising:
step 1) treating alkyl halopyruvate (AHP) with pyridine in ethanol at elevated temperature to form Compound A1' (e.g., alkyl pyridyliumpyruvate halide);
step 2) treating Compound A1' with ACB (e.g., 2-amino-5-chloro-benzaldehyde) and pyridine at elevated temperature to form Compound A2' (e.g., 6-chloro-3-pyridylium-2-alkoxycarbonyl-1-azanapthalene halide);
step 3) treating Compound A2' with morpholine at elevated temperature to form Compound A3' (e.g., 6-chloro-3-amino-2-alkoxycarbonyl-1-azanaphthalene); and
step 4) treating Compound A3' with a Grignard reagent (e.g., methylmagnesium chloride) to form Compound A.

In some embodiments, Compound B is synthesized based on Scheme 6a below, using Compound A prepared by Scheme 3a describe above.

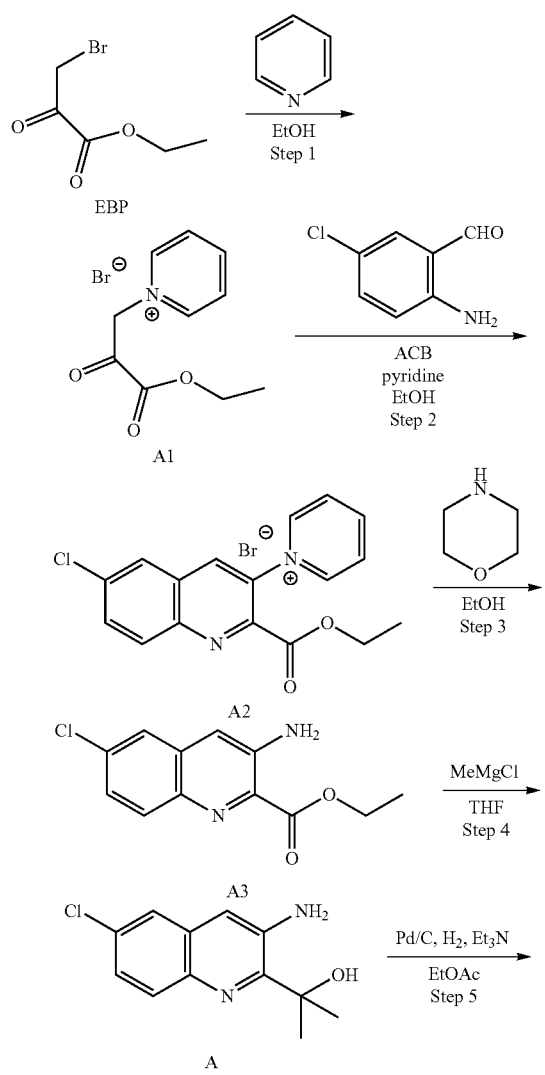

Scheme 6a: Synthesis of Compound B

-continued

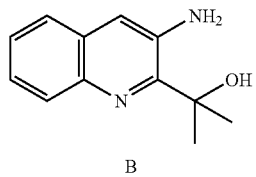

B

In some embodiments, Compound A is synthesized using Scheme 3 or 3a described herein. In some embodiments, Compound A is synthesized according to the method described in US 2013/0190500.

In some embodiments, the present disclosure provides a process for the preparation of Compound B (3-amino-2-(2-hydroxypropyl)-1-azanapthalene), comprising:
step 1) treating an ethyl bromopyruvate (EBP)

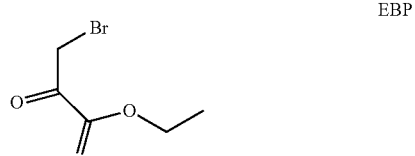

EBP with pyridine to form Compound A1, ethyl pyridyliumpyruvate halide:

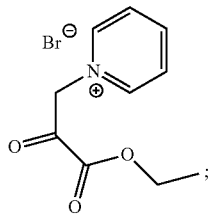

A1 step 2) treating Compound A1 with 2-amino-5-chlorobenzaldehyde (ACB) and pyridine to form Compound A2, 6-chloro-3-pyridylium-2-ethoxycarbonyl-1-azanapthalene halide:

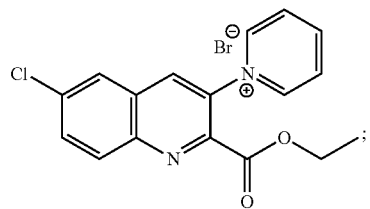

A2 step 3) treating Compound A2 with morpholine to form Compound A3, 6-chloro-3-amino-2-alkoxycarbonyl-1-azanaphthalene:

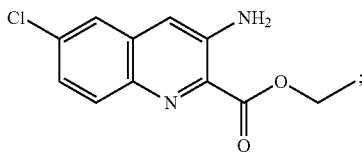

step 4) treating Compound A3 with a Grignard reagent (e.g., methylmagnesium chloride) to form Compound A:

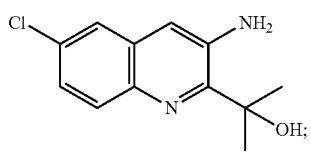

step 5) hydrogenating Compound A in presence of a suitable metal catalyst, hydrogen ($H_2$) in a suitable solvent under suitable conditions to form Compound B.

In some embodiments, the suitable metal catalyst is palladium (Pd), platinum (Pt), or rhodium (Rb). In some embodiments, the suitable metal catalyst is palladium on carbon.

In some embodiments, the suitable solvent is an alcohol (e.g., methanol, ethanol, isopropanol, etc.), trimethylamine, tetrahydrofuran, ethyl acetate, toluene, water, or mixtures thereof.

In some embodiments, the suitable conditions for hydrogenation is hydrogen at a pressure of about 5-30 psi, for example at 15 psi, and a temperature of about 30-35° C.

In some embodiments for preparing Compound B, prior to the hydrogenation step Compound A is purified. In some embodiments, Compound A is purified by chromatography. In some embodiments, Compound A is purified by slurrying with a mixture comprising ethanol acetate, $SiO_2$ and charcoal, followed by solvent exchange and crystallization.

In some embodiments, in the process for preparing Compound B based on Scheme 6a, one or more of the following conditions are satisfied with respect to steps 1-5 above:

a) Compound A formed in step 4) is crude and is not purified by chromatography; or b) Compound A formed in step 4) is slurried with a mixture comprising ethanol acetate, $SiO_2$ and charcoal, followed by solvent exchange and crystallization; or c) Compound A1 is isolated and purified prior to treatment with ACB; or d) Compound A2 is isolated and purified prior to its treatment with a heterocycle.

In some embodiments, at least one of conditions b), c) and d) is satisfied. In some embodiments, at least two of conditions b), c) and d) are satisfied. In some embodiments, all of conditions a) to d) are satisfied.

In some embodiments, Compound A is not purified prior to hydrogenation. In some embodiments, Compound B formed in step 5) is slurried with a mixture comprising ethanol acetate, $SiO_2$ and charcoal, followed by solvent exchange and crystallization. In some embodiments, the process includes conditions c) and/or d).

In some embodiments, the present invention provides a process for the preparation of Compound B based on Scheme 6a above, comprising:

step 1) treating alkyl halopyruvate (AHP) with pyridine in ethanol at elevated temperature to form Compound A1 (e.g., alkyl pyridyliumpyruvate halide);

step 2) treating Compound A1 with ACB (e.g., 2-amino-5-chloro-benzaldehyde) and pyridine at elevated temperature to form Compound A2 (e.g., 6-chloro-3-pyridylium-2-alkoxycarbonyl-1-azanapthalene halide);

step 3) treating Compound A2 with morpholine at elevated temperature to form Compound A3 (e.g., 6-chloro-3-amino-2-alkoxycarbonyl-1-azanaphthalene); and step 4) treating Compound A3 with a Grignard reagent (e.g., methylmagnesium chloride) to form Compound A.

In some embodiments, prior to hydrogenation step, the Compound A is purified and isolated by slurrying with a mixture comprising ethanol acetate, $SiO_2$ and charcoal, followed by solvent exchange with a mixture of n-heptane/ ethyl acetate and crystallization.

In some embodiments, Compound A is not purified or isolated prior to the hydrogenation step. In some embodiments, Compound B formed in step 5) is slurried with a mixture comprising ethanol acetate, $SiO_2$ and charcoal, followed by solvent exchange and crystallization.

In some embodiments, in the process for preparing Compound B, the process for the preparation of Compound A comprises treating Compound A2' or A2 with morpholine at elevated temperature followed by treating the product thereof with a Grignard reagent. In some embodiments, the process for the preparation of Compound A3' or A3 comprises treating Compound A2' or A2 with morpholine at elevated temperature.

In some embodiments, in the process for preparing Compound B, the process for the preparation of Compound A comprises treating Compound A3' or A3 with a Grignard reagent. In some embodiments, the resulting product is crude Compound A, and crude Compound A is purified by slurrying with ethanol acetate, $SiO_2$ and charcoal and then solvent exchanged with a mixture of n-heptane/ethyl acetate and crystallized.

In some embodiments, in the process for preparing Compound B, the process for the preparation of Compound A2' or A2 comprises treating Compound A1' or A1 with the optionally substituted amino benzaldehyde and pyridine at elevated temperature. In some embodiments, a process for the preparation of Compound A1' or A1 comprises treating alkyl halopyruvate (AHP), e.g., EBP, with pyridine in ethanol at elevated temperature.

In some embodiments, Compound A1' or A1 is isolated and purified prior to its treatment with the optionally substituted amino benzaldehyde and pyridine to yield Compound A2' or A2. In some embodiments, Compound A2 or A2' is isolated and purified prior to its treatment with morpholine to yield Compound A3 or A3'. In some embodiments, Compounds A1' and A2', or Compounds A1 and A2 are isolated prior to forming Compound A3' or A3.

In some embodiments, the elevated temperature may be about 50° C. to about 150° C. In some embodiments, the elevated temperature may be about 50° C. to about 100° C. In some embodiments, the elevated temperature may be about 60° C. to about 90° C. In some embodiments, the elevated temperature may be about 70° C. to about 80° C. In some embodiments, the elevated temperature may be about 65° C. to about 75° C.

In some embodiments, in the process for preparing Compound B, a process for the preparation of Compound A comprises treating Compound A2 or A2' with morpholine at about 80° C. followed by treating the product thereof with a Grignard reagent. In some embodiments, the process for the preparation of Compound A3 or A3' comprises treating Compound A2 or A2' with morpholine at about 80° C.

In some embodiments, one or more of the following conditions are satisfied with respect to steps 1-5 above:
a) Compound A formed in step 4) is crude and is not purified by chromatography;
b) Compound A formed in step 4) is slurried with a mixture comprising ethanol acetate, $SiO_2$ and charcoal, followed by solvent exchange and crystallization;
c) Compound A1 or A1' is isolated and purified prior to treatment with an optionally substituted amino benzaldehyde; and
d) Compound A2 or A2' is isolated and purified prior to its treatment with a heterocycle.

In some embodiments, the steps 1-5 includes at least one of conditions b), c) and d). In some embodiments, at least two of conditions b), c) and d) are satisfied. In some embodiments, all of conditions a) to d) are satisfied.

In some embodiments, Compound A is not purified prior to hydrogenation. In some embodiments, Compound B formed in step 5) is slurried with a mixture comprising ethanol acetate, $SiO_2$ and charcoal, followed by solvent exchange and crystallization. In some embodiments, the process includes conditions c) and/or d).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention

EXAMPLES

The invention now being generally described, will be more readily understood by reference to the following examples, which are included merely for purposes of illustration of certain aspects and embodiments of the present invention, and are not intended to limit the invention.

Example 1: Synthesis of Compound A

The synthesis of Compound A is described and shown below in Scheme 7.

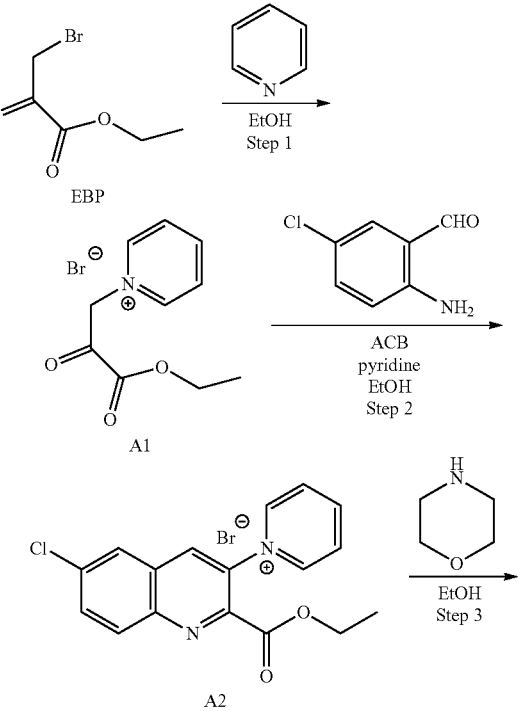

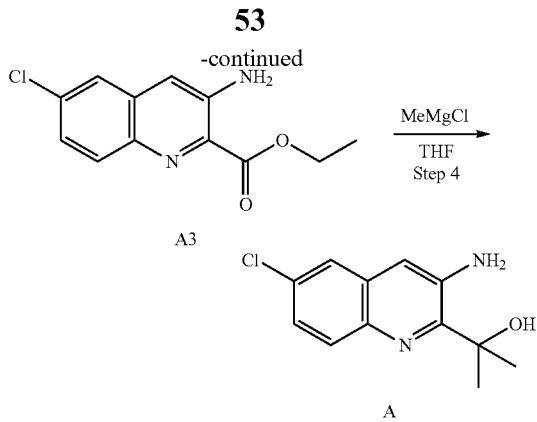

Step 1, preparation of Compound A1: Pyridine (0.49 wt, 0.5 vol, 1.20 eq.) is added to a mixture of ethanol (3.2 wt, 4.0 vol) and ethylbromopyruvate (EBP) (1.0 wt., 1.0 eq.) while maintaining an internal temperature below 40° C. The contents of the reactor are then heated at 65±5° C. for at least 6 hours and then cooled to 18-25° C. The material is used without further purification in the next step.

Step 2, preparation of Compound A2: Following degassing, 2-amino-5-chlorobenzaldehyde (ACB) (0.56 wt., 1.0 eq.) and additional pyridine (0.4 wt., 1.0 eq.) are charged maintaining an internal temperature between 18 and 25° C. The resulting mixture is heated to 80±5° C. until the in-process control (IPC) HPLC confirms not more than (NMT) 0.3% of ACB remaining (reaction complete). The reaction mixture is cooled to 18-25° C. and tert-butylmethyl ether (TBME) (8.14 wt., 11.0 vol.) is charged over 4-5 hours. The resulting mixture is further cooled to 0-5° C. and aged for 3-6 hours. The resulting solids are collected by filtration and the solid is slurry washed on the filter with acetonitrile (3.9 wt., 5.0 vol.). The acetonitrile slurry wash is repeated until an 1H NMR w/w assay indicates an assay >90% w/w. The solids are dried at 55° C. under vacuum with a vigorous nitrogen purge until solvent content is reduced to ≤0.5% w/w ethanol, ≤0.5% w/w TBME, ≤0.5% w/w acetonitrile. Compound A2 (65-75% yield) is stored in double low-density polyethylene (LDPE) bags housed in a high-density polyethylene (HDPE) container at ambient temperature.

Step 3, preparation of Compound A3: A mixture of Compound A2 (1.0 wt, 1.0 eq.) and ethanol (3.5 wt., 4.5 vol.) at 18-25° C. is treated with morpholine (0.6 wt., 0.6 vol., 2.8 eq.) maintaining the internal temperature in the range 18-25° C. The reactor contents are then warmed to 75-85° C. and stirred at this temperature until complete (≤0.5% area 102-2 remaining) by HPLC analysis (typically 4-6 hours). The reaction mixture is then cooled to 0-5° C. over at least 6 hours. Water (15 wt., 15 vol.) is then added over 30-90 minutes maintaining the internal temperature in the range of 0-5° C. throughout. The mixture is aged for 1-2 hours and the solid product is collected by filtration and slurry washed with water until $^1$H NMR analysis confirms a residual morpholine content of 0.1% w/w. The product is then dried at 50° C. under vacuum with a vigorous nitrogen purge until residual water content is ≤0.4% w/w and residual ethanol content is ≤0.2% w/w. Compound A3 (85-93% yield) is stored in double low-density polyethylene (LDPE) bags housed in a high-density polyethylene (HDPE) container at ambient temperature.

Step 4, preparation of Compound A: A solution of Compound A3 (1.0 wt, 1 eq.) in tetrahydrofuran (THF) (12.91 wt., 14.5 vol.) is added to a cooled solution of methylmagnesium chloride (MeMgCl; Grignard reagent) (8.9 vol., 6.7 eq.) while maintaining a temperature of 0±5° C. The resulting mixture is stirred at 0±5° C., warmed to 20±5° C. and stirred at 20±5° C. until IPC LC confirms NMT 0.5% of 102-3 remaining (reaction complete). The reaction mixture is cooled and quenched by the slow addition of ethanol (1.71 wt., 2.19 vol.) followed by a 20% w/w ammonium chloride solution (18.0 vol.). The pH of the reaction mixture is adjusted to 6.5-8.0 by addition of 50% w/w sulfuric acid. The layers are separated, and the aqueous layer is extracted 3 times with toluene (4.35 wt., 5 vol.). The combined organic layers are concentrated to via vacuum distillation and solvent swapping to toluene until residual THF levels are ≤5% w/w. The product is extracted into sulfuric acid (10.0 Vol.) and decolorized with activated carbon (0.1 wt.). The aqueous is washed with toluene (3×4.35 wt., 5.0 vol), TBME (1×3.7 wt., 5.0 vol) and n-heptane (3.4 wt., 5.0 vol.). The pH of the aqueous solution is adjusted with 20% w/w aqueous sodium hydroxide to 8-9, the solution is aged for 3-4 hours and the product is collected by filtration and dried till the water content is ≤0.5% w/w. The crude Compound A is dissolved in ethyl acetate (13.5 wt., 15 vol) and treated with activated carbon and silica gel for 3-4 hours. The mixture is filtered and the ethyl acetate solution of Compound A is concentrated to approximately 5 volumes and solvent swapped to n-heptane until residual ethyl acetate is ≤1.0% wt/wt. The heptane (5.0 vol.) slurry of Compound A is re-treated with ethyl acetate (0.45 wt., 0.5 vol.) and the mixture is heated to obtain a solution from which Compound A crystallizes on controlled cooling to 18-25° C. then to 0-5° C. The crystallized product is collected by filtration and dried at 45° C. under vacuum with a vigorous nitrogen purge until residual solvents pass the desired specifications (40-65% yield).

Example 2: Synthesis of Compound B

The synthesis of Compound B is described and shown below in Scheme 8.

Scheme 8: Synthesis of Compound B

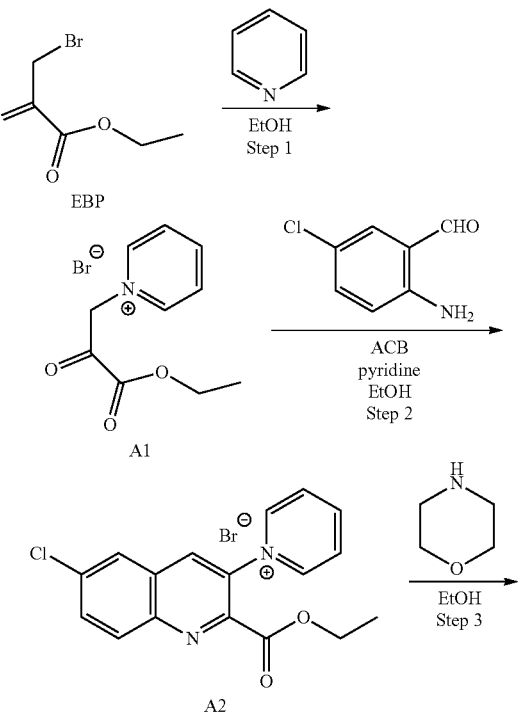

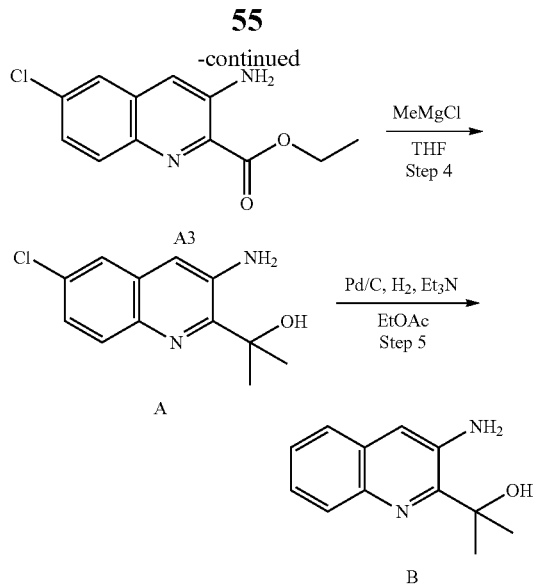

Step 1: Preparation of Compound A1: A solution of ethyl bromopyruvate (EBP) (1.0 kg, 5.13 mol) in EtOH (4.0 L) was treated with pyridine (486 g, 6.15 mol) at 18-25° C. The reaction mixture was then heated to 60-68° C. over 1-3 hours and stirred at this temperature for 7-8 hours. The reaction mixture was cooled to 18-25° C. and taken on as a solution to the next stage without further manipulation. NMR potency determination provided a solution assay of Compound A1 (702 g, 50%).

Step 2: Preparation of Compound A2: To the solution of Compound A1 (702 g, 2.56 mol) in ethanol (4.0 L) at 18-25° C. was charged 2-amino-5-chlorobenzaldehyde (ACB) (525 g, 3.33 mol). Pyridine was then charged to the mixture while maintaining an internal temperature of 18-35° C. during addition. The resulting reaction mixture was then heated to 78-88° C. over 1-3 hours. The reaction mixture was stirred at this temperature until complete by HPLC analysis (<1.0% ACB remaining).

The reaction mixture was then cooled to 18-25° C. over 1-3 hours and MTBE (11.0 L) was added over 1-2 hours maintaining an internal temperature of 18-25° C. The mixture was then cooled to 0-5° C. and aged at this temperature for 5-12 hours. The solids were removed by filtration and the filter cake was washed with MTBE (2×5.0 L) and acetonitrile (5.0 L). This provided the product Compound A2, after vacuum drying at 40° C., as a yellow solid (1.52 kg, 76%).

Step 3: Preparation of Compound A3: A solution of Compound A2 (1.52 kg, 3.86 mol) in ethanol (6.84 L) at 18-25° C. was treated with morpholine (942 g, 10.81 mol) over 15-45 mins. The resulting mixture was heated to 75-85° C. and held at this temperature until complete by HPLC analysis (<0.5% Compound A2 remaining). The reaction mixture was cooled to 0-5° C. over 6 hours and then water (7.5 L) was added over 30-180 minutes, maintaining the internal temperature at 0-5° C.

The resulting mixture was then aged for 1-2 hours and the solid was removed by filtration. The filter cake was washed with water (2×2.5 L) and dried at 50° C. in a vacuum oven. This provided the desired product Compound A3 (871 g, 90%) as a yellow solid.

Step 4: Preparation of Compound A: A solution of Compound A3 (871 g, 3.47 mol) in THF (12.0 L) was cooled to 0-5° C. In a separate vessel, methylmagnesium chloride (3M in THF, 7.75 L, 23.25 mol) was cooled to −5-5° C. and treated with the solution of Compound A3 over 4-6 hours. Once the addition was complete, the reaction mixture was stirred at −5-5° C. until complete by HPLC analysis (<0.5% Compound A3 remaining).

Absolute ethanol (1.9 L) was slowly charged to the reaction mixture over 2-4 hours, maintaining the internal temperature at 0-10° C. 20% w/w ammonium chloride (16.0 L) was then added over 2-4 hours maintaining the internal temperature at 0-10° C. The reaction mixture was then warmed to 18-25° C. and the biphasic mixture was agitated for 30 min to 1 hour. The mixture was treated with 50% w/w sulfuric acid, maintaining the internal temperature at 18-25° C. throughout the addition, until the pH of the mixture was in the range of 6.5-8.0. The phases were separated and the aqueous phase was extracted with toluene (2×5.0 L). The combined organics were concentrated by distillation to approximately 5 volumes. The solution was treated with toluene (5.0 L) and concentrated again to approximately 5 volumes.

The organics were then treated with 10% v/v sulfuric acid (10.0 L). The biphasic mixture was decolorized with activated charcoal and the organic phase was re-extracted with 10% v/v sulfuric acid (10.0 L). The combined aqueous phases were washed with toluene (3×5.0 L), MTBE (1×5.0 L) and n-heptane (1×5.0 L). The aqueous phase was then pH adjusted to 8.0-9.0 using 20% w/w sodium hydroxide, while maintaining an internal temperature of 18-25° C. The mixture was aged for 3-4 hours and the resulting solid was collected by filtration and washed water (3×5.0 L). The solid was dried at 55° C. in a vacuum oven until the water content was <0.5% wt/wt by KF titration.

The solids were then recrystallized from ethyl acetate/heptane (3:2) (25.0 L) to provide the desired product Compound A as a white solid (534 g, 65%).

Step 5: Preparation of Compound B: A mixture of Compound A (534 g, 2.26 mol), Pd/C (53.4 g), ethyl acetate (5.34 L) and triethylamine (686 g, 6.78 mol) at 30-35° C. were subjected to hydrogenation (15 psi, hydrogen) and stirred at 30-35° C. until completion of reaction (<0.5% ADX-102 remaining). The reaction mixture was filtered over a pad of Celite® and the filtercake was washed with ethyl acetate (3×2.5 L). The solution of Compound B in ethyl acetate was treated with an aqueous solution of N-acetyl-L-cysteine (1.0 kg) in water (10.0 L) in 2 equal portions to scavenge residual palladium metal. The rich organic solution was then washed sequentially with water (5.0 L) and brine (5.0 L). The rich organics were distilled to approximately 3 volumes and treated with n-heptane (15 volumes) at 20-25° C. The resulting solids were collected by filtration to provide the desired product Compound B (411 g, 90%) as a white solid.

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

We claim:

1. A method of preparing Compound A, 6-chloro-3-amino-2-(2-hydroxypropyl)-1-azanapthalene:

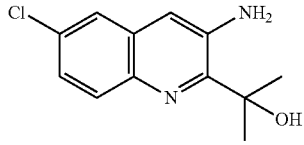

or a pharmaceutically acceptable salt thereof, comprising:
step 1) treating ethyl bromopyruvate (EBP)

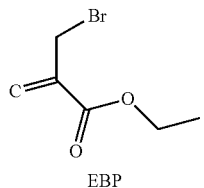

with pyridine to form Compound A1:

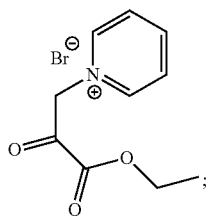

step 2) treating Compound A1 with 2-amino-5-chloro-benzaldehyde (ACB)

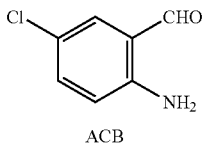

and pyridine to form Compound A2:

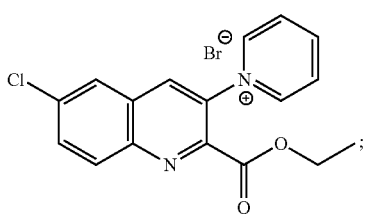

step 3) treating Compound A2 with morpholine and ethanol form Compound A3:

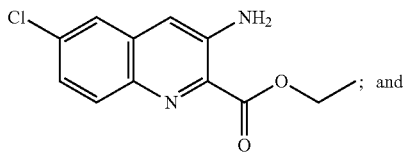

step 4) treating Compound A3 with methyl Grignard reagent to form Compound A; wherein crude Compound A formed in step 4) is dissolved in ethyl acetate and treated with activated carbon and silica gel to form a mixture,
(i) the mixture is filtered;
(ii) the filtrate obtained after filtration from (i) is concentrated and mixed with heptane to make a slurry;
(iii) the slurry is heated with ethyl acetate to obtain a solution; and
(iv) the solution is cooled to obtain crystalline Compound A; wherein one or both of the following conditions are satisfied:
a) Compound A1 is isolated and purified prior to treatment with ACB; and
b) Compound A2 is isolated and purified prior to its treatment with morpholine.

2. The method of claim 1, wherein in step 1), the treating takes place in ethanol as solvent at 65±5° C.

3. The method of claim 1, wherein in step 3), the treating takes place in ethanol at an elevated temperature of 75° C. to 85° C.

4. The method of claim 1, wherein in step 4), the treating with methyl Grignard reagent takes place in tetrahydrofuran as the solvent.

5. The method of claim 1, wherein the filtrate of step 4) part (ii) is concentrated and mixed with heptane to make a slurry until the residual ethyl acetate is <1.0% wt./wt.

6. The method of claim 1, wherein Compound A1 is isolated and purified prior to treatment with 2-amino-5-chloro-benzaldehyde (ACB).

7. The method of claim 6, wherein Compound A2 is isolated and purified prior to its treatment with the morpholine.

8. The method of claim 7, wherein the Compound A formed in step 4) is crystallized in part (iv) by controlled cooling to 18-25° C. following by cooling at 0-5° C.

9. The method of claim 8, wherein the crystallized compound A is collected by filtration and dried at 45° C. under vacuum.

* * * * *